(12) United States Patent
Taylor et al.

(10) Patent No.: US 7,972,601 B2
(45) Date of Patent: Jul. 5, 2011

(54) METHOD OF PROMOTING DELIVERY OF AN ANTIOXIDANT AGENT TO A CELL EXPRESSION NEUROLIGIN

(75) Inventors: Palmer Taylor, Del Mar, CA (US); Davide Comoletti, San Diego, CA (US); Lori Jennings, San Diego, CA (US); Robyn Flynn, Calgary (CA)

(73) Assignee: The Regents of the University of California, Oakland, CA (US)

( * ) Notice: Subject to any disclaimer, the term of this patent is extended or adjusted under 35 U.S.C. 154(b) by 359 days.

(21) Appl. No.: 11/596,160

(22) PCT Filed: May 10, 2005

(86) PCT No.: PCT/US2005/017522
§ 371 (c)(1),
(2), (4) Date: Nov. 8, 2006

(87) PCT Pub. No.: WO2005/115478
PCT Pub. Date: Dec. 8, 2005

(65) Prior Publication Data
US 2007/0180544 A1    Aug. 2, 2007

Related U.S. Application Data

(60) Provisional application No. 60/570,324, filed on May 11, 2004.

(51) Int. Cl.
*A61K 39/00* (2006.01)
*A61K 39/385* (2006.01)
*A01N 37/18* (2006.01)
*A01N 38/00* (2006.01)

(52) U.S. Cl. ............... 424/185.1; 424/192.1; 424/194.1; 514/2; 514/18

(58) Field of Classification Search .................. None
See application file for complete search history.

(56) References Cited

OTHER PUBLICATIONS

Jamain, Stephane et al., Mutations of the X-linked genes encoding neuroligins NLGN3 and NLGN4 are associated with autism; Nature Genetics, May 2003, pp. 27-29, vol. 34.
Jamain, Stephane, et al., Mutations of the X-linked neuroligins NLGN3 and NLGN4 are associated with autism, Am. J. Med. Genetics, 2003, 122B, 1, p. 20.
Ylisaukko-Oja, Tero et al., Sequence and haplotype analysis of neuroligins NLGN1, NLGN3 and NLGN4 in Finnish autism families, Am. J. Med. Genetics, 2003, 122B, 1 pp. 75-76.

*Primary Examiner* — Olga N Chernyshev
(74) *Attorney, Agent, or Firm* — Joseph R. Baker, Jr.; Gavrilovich Dodd & Lindsey LLP

(57) ABSTRACT

Provided are methods and compositions for treating autism spectrum disorders by administering an antioxidant or agent that stabilize or enhance expression of altered neuroligins. An aspect of the disclosure includes site-specific delivery of the antioxidant to the endoplasmic reticulum (ER) to reverse incorrect disulfide binding of the protein neuroligin. Also disclosed is a method of targeting the antioxidant to neuroligin by using the calcium binding or other recognition site of neuroligin to bind the antioxidant. The antioxidant can be cysteamine linked to a molecule which binds to a binding site.

9 Claims, 16 Drawing Sheets

DYKDDDDKLAAANSSIDLQKLDDVDPLVTTNFGKIRGIKKELNNEILGPVIQFLGVPYAAPPTGEH 93

RFQPPEPPSPWSDIRNATQFAPVCPQNIIDGRLPEVMLPVWFTNNLDVVSSYVQDQSEDCLYLNIY 159

VPTEIVKRISKECARKPGKKICRKGDIRDSGGPKPVMVYIHGGSYMEGTGNLYDGSVLASYGNVIV 225

ITVNYRLGVLGFLSTGDQAAKGNYGLLDLIQALRWTSENIGFFGGDPLRITVFGSGAGGSCVNLLT 291

LSHYSEGNRWSNSTKGLFQRAIAQSGTALSSWAVSFQPAKYARILATKVGCNVSDTVELVECLQKK 357

PYKELVDQDVQPARYHIAFGPVIDGDVIPDDPQILMEQGEFLNYDIMLGVNQGEGLKFVENIVDSD 423

DGVSASDFDFAVSNFVDNLYGYPEGKDVLRETIKFMYTDWADRHNPETRRKTLLALFTDHQWVAPA 489

VATADLHSNFGSPTYFYAFYHHCQTDQVPAWADAAHGDEVPYVLGIPMIGPTELFPCNFSKNDVML 555

SAVVMTYWTNFAKTGDPNQPVPQDTKFIHTKPNRFEEVAWTRYSQKDQLYLHIGLKPRVKEHYRAN 621

KVNLWLELVPHLHNLNDISQYTSTTTKVPSTDTTLRPTRKNSTPVTSAPPTAKQDDPKQQPSPFSV 687

DQRD 691

FIGURE 1

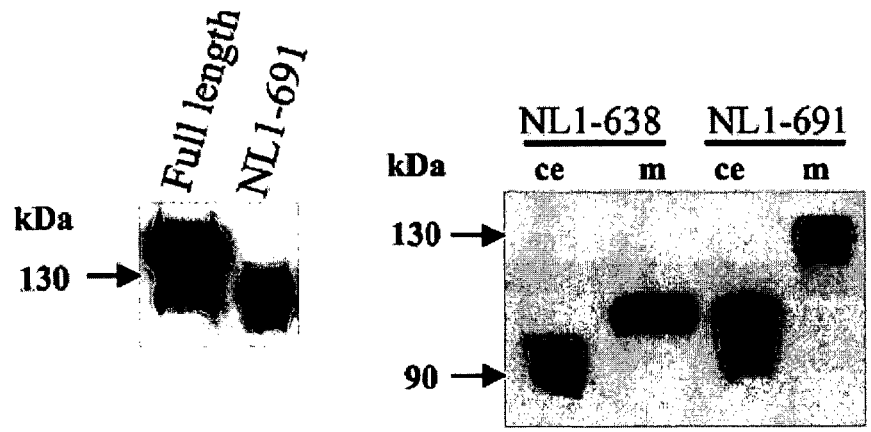

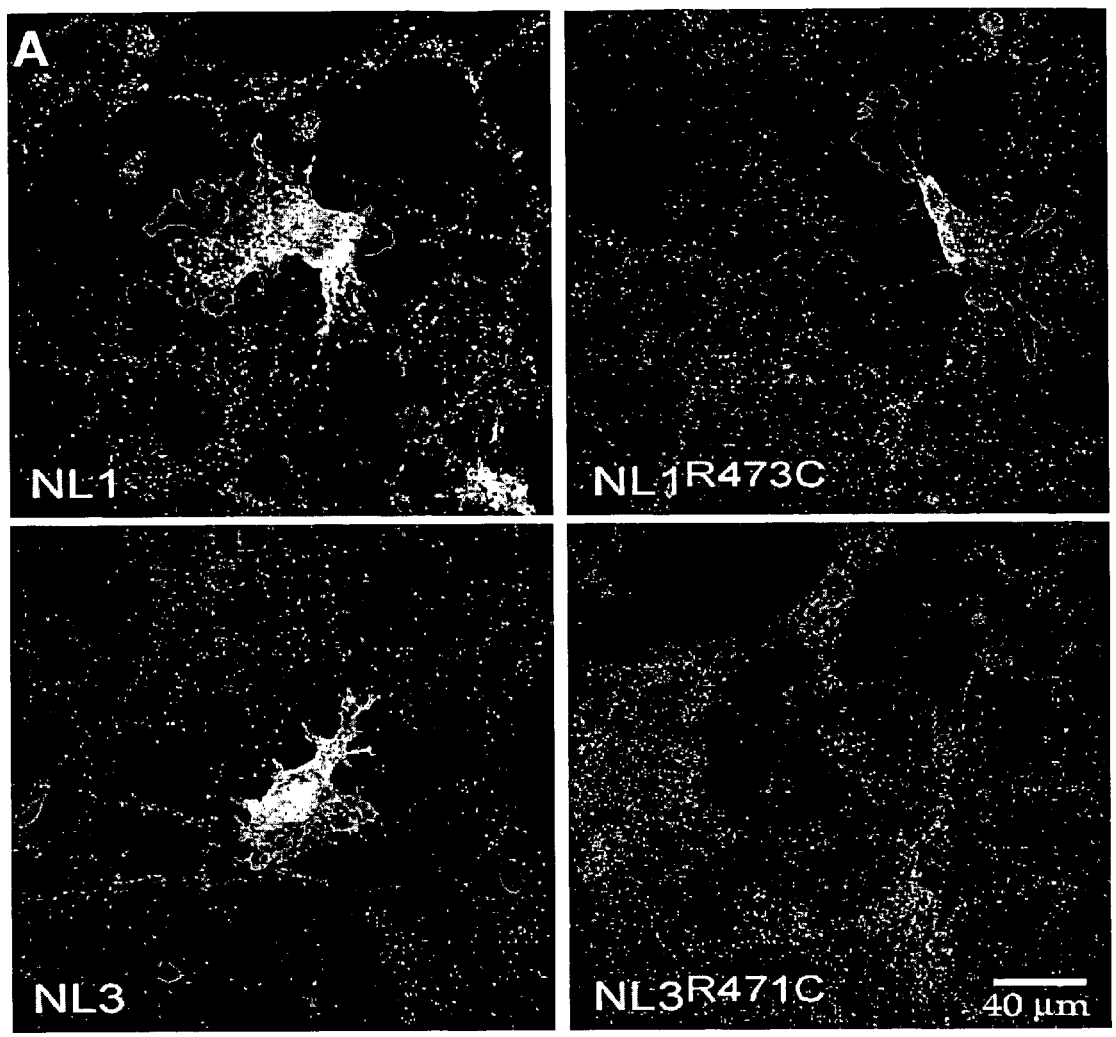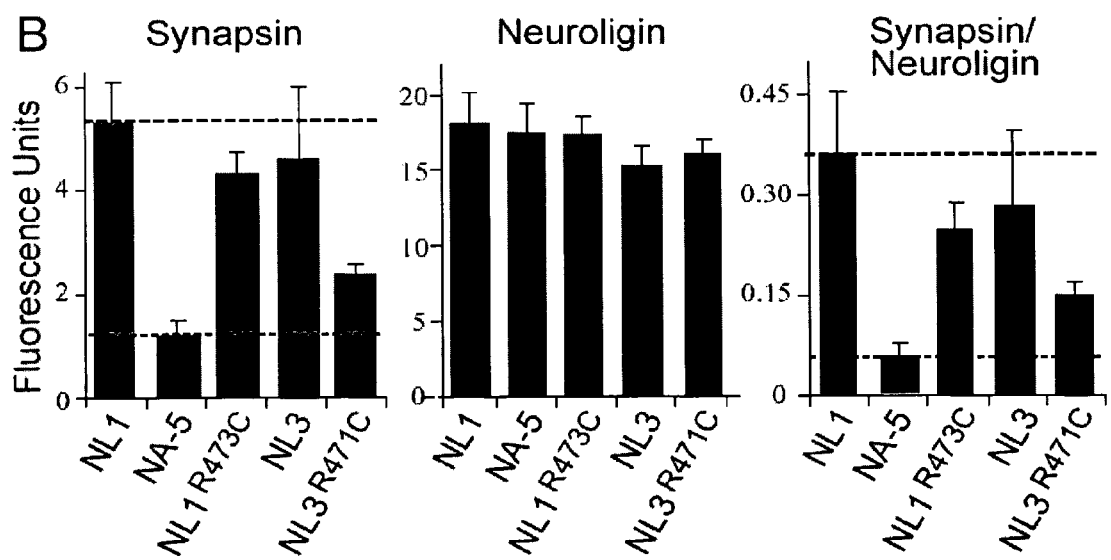
FIGURE 22

SEQUENCE LISTING

<160> NUMBER OF SEQ ID NOS: 9

<210> SEQ ID NO 1
<211> LENGTH: 2487
<212> TYPE: DNA
<213> ORGANISM: homo sapiens
<220> FEATURE:
<221> NAME/KEY: CDS
<222> LOCATION: (1)..(2487)

<400> SEQUENCE: 1

```
atg tgg ctg cgg ctt ggc ccg ccc tcg ctg tcc ctg agc ccc aag ccc      48
Met Trp Leu Arg Leu Gly Pro Pro Ser Leu Ser Leu Ser Pro Lys Pro
1               5                   10                  15 acg gtt ggc agg agc ctg tgc ctc acc ctg tgg ttc ctc agt ttg gcg      96
Thr Val Gly Arg Ser Leu Cys Leu Thr Leu Trp Phe Leu Ser Leu Ala
            20                  25                  30 ctg agg gcc agt acc cag gcc cca gca ccc aca gtc aac act cac ttt     144
Leu Arg Ala Ser Thr Gln Ala Pro Ala Pro Thr Val Asn Thr His Phe
        35                  40                  45 ggg aag cta agg ggt gcc cga gta cca ctg ccc agt gag atc ctg ggg     192
Gly Lys Leu Arg Gly Ala Arg Val Pro Leu Pro Ser Glu Ile Leu Gly
    50                  55                  60 cct gtg gac caa tac ctg ggg gtg ccc tac gca gct ccc ccg atc ggc     240
Pro Val Asp Gln Tyr Leu Gly Val Pro Tyr Ala Ala Pro Pro Ile Gly
65                  70                  75                  80 gag aaa cgt ttc ctg ccc cct gaa cca ccc cca tcc tgg tcg ggc atc     288
Glu Lys Arg Phe Leu Pro Pro Glu Pro Pro Pro Ser Trp Ser Gly Ile
                85                  90                  95 cgg aac gcc aca cac ttt ccc cca gtg tgc ccc cag aac atc cac aca     336
Arg Asn Ala Thr His Phe Pro Pro Val Cys Pro Gln Asn Ile His Thr
            100                 105                 110 gct gtg ccc gaa gtc atg ctg ccg gtc tgg ttc act gcc aac ttg gat     384
Ala Val Pro Glu Val Met Leu Pro Val Trp Phe Thr Ala Asn Leu Asp
        115                 120                 125 atc gtc gct act tac atc cag gag ccc aac gaa gac tgt ctc tac ctg     432
Ile Val Ala Thr Tyr Ile Gln Glu Pro Asn Glu Asp Cys Leu Tyr Leu
    130                 135                 140 aac gtc tat gtg ccg acg gag gat gga tcc ggc gct aag aaa cag ggc     480
Asn Val Tyr Val Pro Thr Glu Asp Gly Ser Gly Ala Lys Lys Gln Gly
145                 150                 155                 160 gag gac tta gcg gat aat gac ggg gat gaa gat gaa gac atc cgg gac     528
Glu Asp Leu Ala Asp Asn Asp Gly Asp Glu Asp Glu Asp Ile Arg Asp
                165                 170                 175 agt ggt gct aaa ccc gtc atg gtc tac atc cac gga ggc tct tac atg     576
Ser Gly Ala Lys Pro Val Met Val Tyr Ile His Gly Gly Ser Tyr Met
            180                 185                 190 gaa ggg aca ggc aac atg att gat ggc agc atc ctc gcc agt tat ggc     624
Glu Gly Thr Gly Asn Met Ile Asp Gly Ser Ile Leu Ala Ser Tyr Gly
        195                 200                 205 aat gtc atc gtc atc acc ctc aac tat cgg gtt gga gtg cta ggt ttc     672
Asn Val Ile Val Ile Thr Leu Asn Tyr Arg Val Gly Val Leu Gly Phe
    210                 215                 220 ctg agt act gga gat cag gct gcc aag ggc aac tat ggg ctc ctt gac     720
Leu Ser Thr Gly Asp Gln Ala Ala Lys Gly Asn Tyr Gly Leu Leu Asp
225                 230                 235                 240 cag atc cag gcc ctc cgc tgg gtg agc gag aat att gcc ttc ttc ggg     768
Gln Ile Gln Ala Leu Arg Trp Val Ser Glu Asn Ile Ala Phe Phe Gly
                245                 250                 255 gga gac ccc cgc cgg atc act gtc ttt ggc tcg ggc att ggt gca tcc     816
```

-continued

| | |
|---|---|
| Gly Asp Pro Arg Arg Ile Thr Val Phe Gly Ser Gly Ile Gly Ala Ser<br>            260                    265                270 | |
| tgc gtc agc ctc ctc acg ttg tca cat cac tca gag gga ctt ttc cag<br>Cys Val Ser Leu Leu Thr Leu Ser His His Ser Glu Gly Leu Phe Gln<br>          275                    280                    285 | 864 |
| aga gcc atc atc caa agt ggc tct gct ctg tcc agc tgg gct gtg aac<br>Arg Ala Ile Ile Gln Ser Gly Ser Ala Leu Ser Ser Trp Ala Val Asn<br>  290                    295                    300 | 912 |
| tac caa cca gtg aag tac acc agc ctg ctg gca gac aaa gtg ggc tgt<br>Tyr Gln Pro Val Lys Tyr Thr Ser Leu Leu Ala Asp Lys Val Gly Cys<br>305                  310                    315                    320 | 960 |
| aat gtg ctg gac acc gtg gat atg gtg gac tgt ctt cgg caa aag agt<br>Asn Val Leu Asp Thr Val Asp Met Val Asp Cys Leu Arg Gln Lys Ser<br>            325                    330                    335 | 1008 |
| gcc aag gag ctg gta gag cag gac atc cag cca gcc cgc tac cac gtg<br>Ala Lys Glu Leu Val Glu Gln Asp Ile Gln Pro Ala Arg Tyr His Val<br>                340                    345                    350 | 1056 |
| gcc ttt ggc cct gtg att gat ggt gat gtc att cct gat gac cct gag<br>Ala Phe Gly Pro Val Ile Asp Gly Asp Val Ile Pro Asp Asp Pro Glu<br>          355                    360                    365 | 1104 |
| atc ctc atg gag cag ggc gag ttc ctc aac tat gac atc atg cta ggt<br>Ile Leu Met Glu Gln Gly Glu Phe Leu Asn Tyr Asp Ile Met Leu Gly<br>370                375                    380 | 1152 |
| gtc aac cag ggc gag ggt ctc aag ttt gtg gaa ggg gtg gtg gac cct<br>Val Asn Gln Gly Glu Gly Leu Lys Phe Val Glu Gly Val Val Asp Pro<br>385                390                    395                    400 | 1200 |
| gag gat ggt gtc tct ggc act gac ttt gac tat tcc gtc tcc aat ttt<br>Glu Asp Gly Val Ser Gly Thr Asp Phe Asp Tyr Ser Val Ser Asn Phe<br>            405                    410                    415 | 1248 |
| gtg gac aat ctg tat ggc tat cct gag ggt aag gac acc ctg cga gag<br>Val Asp Asn Leu Tyr Gly Tyr Pro Glu Gly Lys Asp Thr Leu Arg Glu<br>                420                    425                    430 | 1296 |
| acc atc aag ttc atg tat aca gac tgg gca gac cgt gac aac cct gag<br>Thr Ile Lys Phe Met Tyr Thr Asp Trp Ala Asp Arg Asp Asn Pro Glu<br>          435                    440                    445 | 1344 |
| acc cgc gt aaa aca ctg gtg gca ctc ttc act gac cac cag tgg gtg<br>Thr Arg Arg Lys Thr Leu Val Ala Leu Phe Thr Asp His Gln Trp Val<br>450                455                    460 | 1392 |
| gag ccc tca gtg gtg aca gcc gat ctg cat gcc cgc tac ggc tcg cct<br>Glu Pro Ser Val Val Thr Ala Asp Leu His Ala Arg Tyr Gly Ser Pro<br>465                470                    475                    480 | 1440 |
| acc tac ttc tac gcc ttc tat cat cac tgc cag agc ctc atg aag cct<br>Thr Tyr Phe Tyr Ala Phe Tyr His His Cys Gln Ser Leu Met Lys Pro<br>                485                    490                    495 | 1488 |
| gct tgg tca gat gca gct cat ggg gat gaa gta ccc tat gtt ttt ggg<br>Ala Trp Ser Asp Ala Ala His Gly Asp Glu Val Pro Tyr Val Phe Gly<br>          500                    505                    510 | 1536 |
| gtt cct atg gta ggc ccc act gac ctt ttc ccc tgc aac ttc tcc aag<br>Val Pro Met Val Gly Pro Thr Asp Leu Phe Pro Cys Asn Phe Ser Lys<br>            515                    520                    525 | 1584 |
| aat gat gtt atg ctc agt gct gtc gtc atg acc tat tgg acc aac ttt<br>Asn Asp Val Met Leu Ser Ala Val Val Met Thr Tyr Trp Thr Asn Phe<br>530                535                    540 | 1632 |
| gcc aag act ggg gat ccc aac aag ccg gtc ccc cag gac acc aag ttc<br>Ala Lys Thr Gly Asp Pro Asn Lys Pro Val Pro Gln Asp Thr Lys Phe<br>545                550                    555                    560 | 1680 |
| att cac acc aag gcc aac cgc ttt gag gaa gtg gcc tgg tcc aaa tac<br>Ile His Thr Lys Ala Asn Arg Phe Glu Glu Val Ala Trp Ser Lys Tyr<br>                565                    570                    575 | 1728 |
| aat ccc cga gac cag ctc tac ctt cac atc ggg ctg aaa cca agg gtc | 1776 |

```
Asn Pro Arg Asp Gln Leu Tyr Leu His Ile Gly Leu Lys Pro Arg Val
            580                 585                 590 cga gat cat tac cgg gcc act aag gtg gcc ttt tgg aaa cat ctg gtg    1824
Arg Asp His Tyr Arg Ala Thr Lys Val Ala Phe Trp Lys His Leu Val
            595                 600                 605 ccc cac cta tac aac ctg cat gac atg ttc cac tat acg tcc acc acc    1872
Pro His Leu Tyr Asn Leu His Asp Met Phe His Tyr Thr Ser Thr Thr
            610                 615                 620 acc aaa gtg ccg cct ccg gat acc acc cac agc tcc cac atc acc cgc    1920
Thr Lys Val Pro Pro Pro Asp Thr Thr His Ser Ser His Ile Thr Arg
625                 630                 635                 640 agg ccc aat ggc aag acc tgg agc acc aag cgg cca gcc atc tca cct    1968
Arg Pro Asn Gly Lys Thr Trp Ser Thr Lys Arg Pro Ala Ile Ser Pro
                645                 650                 655 gcc tac agc aac gag aat gcc cag ggg tcc tgg aac ggg gac cag gat    2016
Ala Tyr Ser Asn Glu Asn Ala Gln Gly Ser Trp Asn Gly Asp Gln Asp
            660                 665                 670 gca ggg cca ctc ctg gtg gag aac cct cgt gac tac tcc act gaa tta    2064
Ala Gly Pro Leu Leu Val Glu Asn Pro Arg Asp Tyr Ser Thr Glu Leu
        675                 680                 685 agt gtc acc atc gcc gtg ggg gcc tcc ctc ctg ttc ctt aac gtt ctg    2112
Ser Val Thr Ile Ala Val Gly Ala Ser Leu Leu Phe Leu Asn Val Leu
690                 695                 700 gcc ttc gct gcc ctc tac tac cgt aag gac aaa cgg cgc cag gag ccc    2160
Ala Phe Ala Ala Leu Tyr Tyr Arg Lys Asp Lys Arg Arg Gln Glu Pro
705                 710                 715                 720 ctg cgg cag cct agc cct cag cgg gga gcc ggg gcc ccg gag ttg gga    2208
Leu Arg Gln Pro Ser Pro Gln Arg Gly Ala Gly Ala Pro Glu Leu Gly
                725                 730                 735 gct gct cca gag gag gag ctg gca gca tta caa ctg ggc ccc acc cac    2256
Ala Ala Pro Glu Glu Glu Leu Ala Ala Leu Gln Leu Gly Pro Thr His
            740                 745                 750 cac gag tgt gag gcc ggt ccc ccc cat gac acg ctg cgc ctc act gca    2304
His Glu Cys Glu Ala Gly Pro Pro His Asp Thr Leu Arg Leu Thr Ala
            755                 760                 765 ttg ccc gac tac acc ctg acc ctg cgg cgc tcc ccg gat gac atc cca    2352
Leu Pro Asp Tyr Thr Leu Thr Leu Arg Arg Ser Pro Asp Asp Ile Pro
        770                 775                 780 ctc atg acc ccc aac acc atc act atg atc ccc aac tcc ctg gta ggg    2400
Leu Met Thr Pro Asn Thr Ile Thr Met Ile Pro Asn Ser Leu Val Gly
785                 790                 795                 800 ctg cag aca ttg cac ccc tat aac acc ttt gcc gca ggg ttc aac agt    2448
Leu Gln Thr Leu His Pro Tyr Asn Thr Phe Ala Ala Gly Phe Asn Ser
                805                 810                 815 acc ggg ctg ccc cac tca cac tcc act acc cgg gta tag                2487
Thr Gly Leu Pro His Ser His Ser Thr Thr Arg Val
            820                 825

<210> SEQ ID NO 2
<211> LENGTH: 828
<212> TYPE: PRT
<213> ORGANISM: homo sapiens

<400> SEQUENCE: 2

Met Trp Leu Arg Leu Gly Pro Pro Ser Leu Ser Leu Ser Pro Lys Pro
1               5                   10                  15

Thr Val Gly Arg Ser Leu Cys Leu Thr Leu Trp Phe Leu Ser Leu Ala
            20                  25                  30

Leu Arg Ala Ser Thr Gln Ala Pro Ala Pro Thr Val Asn Thr His Phe
        35                  40                  45
```

-continued

Gly Lys Leu Arg Gly Ala Arg Val Pro Leu Pro Ser Glu Ile Leu Gly
    50                  55                  60

Pro Val Asp Gln Tyr Leu Gly Val Pro Tyr Ala Ala Pro Ile Gly
65                  70                  75                  80

Glu Lys Arg Phe Leu Pro Pro Glu Pro Pro Ser Trp Ser Gly Ile
                85                  90                  95

Arg Asn Ala Thr His Phe Pro Val Cys Pro Gln Asn Ile His Thr
                100                 105                 110

Ala Val Pro Glu Val Met Leu Pro Val Trp Phe Thr Ala Asn Leu Asp
            115                 120                 125

Ile Val Ala Thr Tyr Ile Gln Glu Pro Asn Glu Asp Cys Leu Tyr Leu
    130                 135                 140

Asn Val Tyr Val Pro Thr Glu Asp Gly Ser Gly Ala Lys Lys Gln Gly
145                 150                 155                 160

Glu Asp Leu Ala Asp Asn Asp Gly Asp Glu Asp Glu Asp Ile Arg Asp
                165                 170                 175

Ser Gly Ala Lys Pro Val Met Val Tyr Ile His Gly Gly Ser Tyr Met
                180                 185                 190

Glu Gly Thr Gly Asn Met Ile Asp Gly Ser Ile Leu Ala Ser Tyr Gly
                195                 200                 205

Asn Val Ile Val Ile Thr Leu Asn Tyr Arg Val Gly Val Leu Gly Phe
    210                 215                 220

Leu Ser Thr Gly Asp Gln Ala Ala Lys Gly Asn Tyr Gly Leu Leu Asp
225                 230                 235                 240

Gln Ile Gln Ala Leu Arg Trp Val Ser Glu Asn Ile Ala Phe Phe Gly
                245                 250                 255

Gly Asp Pro Arg Arg Ile Thr Val Phe Gly Ser Gly Ile Gly Ala Ser
                260                 265                 270

Cys Val Ser Leu Leu Thr Leu Ser His His Ser Glu Gly Leu Phe Gln
                275                 280                 285

Arg Ala Ile Ile Gln Ser Gly Ser Ala Leu Ser Ser Trp Ala Val Asn
    290                 295                 300

Tyr Gln Pro Val Lys Tyr Thr Ser Leu Leu Ala Asp Lys Val Gly Cys
305                 310                 315                 320

Asn Val Leu Asp Thr Val Asp Met Val Asp Cys Leu Arg Gln Lys Ser
                325                 330                 335

Ala Lys Glu Leu Val Glu Gln Asp Ile Gln Pro Ala Arg Tyr His Val
                340                 345                 350

Ala Phe Gly Pro Val Ile Asp Gly Asp Val Ile Pro Asp Asp Pro Glu
            355                 360                 365

Ile Leu Met Glu Gln Gly Glu Phe Leu Asn Tyr Asp Ile Met Leu Gly
    370                 375                 380

Val Asn Gln Gly Glu Gly Leu Lys Phe Val Glu Gly Val Val Asp Pro
385                 390                 395                 400

Glu Asp Gly Val Ser Gly Thr Asp Phe Asp Tyr Ser Val Ser Asn Phe
                405                 410                 415

Val Asp Asn Leu Tyr Gly Tyr Pro Glu Gly Lys Asp Thr Leu Arg Glu
            420                 425                 430

Thr Ile Lys Phe Met Tyr Thr Asp Trp Ala Asp Arg Asp Asn Pro Glu
    435                 440                 445

Thr Arg Arg Lys Thr Leu Val Ala Leu Phe Thr Asp His Gln Trp Val
    450                 455                 460

Glu Pro Ser Val Val Thr Ala Asp Leu His Ala Arg Tyr Gly Ser Pro
465                 470                 475                 480

```
Thr Tyr Phe Tyr Ala Phe Tyr His His Cys Gln Ser Leu Met Lys Pro
                485                 490                 495

Ala Trp Ser Asp Ala Ala His Gly Asp Glu Val Pro Tyr Val Phe Gly
            500                 505                 510

Val Pro Met Val Gly Pro Thr Asp Leu Phe Pro Cys Asn Phe Ser Lys
        515                 520                 525

Asn Asp Val Met Leu Ser Ala Val Val Met Thr Tyr Trp Thr Asn Phe
    530                 535                 540

Ala Lys Thr Gly Asp Pro Asn Lys Pro Val Pro Gln Asp Thr Lys Phe
545                 550                 555                 560

Ile His Thr Lys Ala Asn Arg Phe Glu Glu Val Ala Trp Ser Lys Tyr
                565                 570                 575

Asn Pro Arg Asp Gln Leu Tyr Leu His Ile Gly Leu Lys Pro Arg Val
            580                 585                 590

Arg Asp His Tyr Arg Ala Thr Lys Val Ala Phe Trp Lys His Leu Val
        595                 600                 605

Pro His Leu Tyr Asn Leu His Asp Met Phe His Tyr Thr Ser Thr Thr
    610                 615                 620

Thr Lys Val Pro Pro Asp Thr Thr His Ser Ser His Ile Thr Arg
625                 630                 635                 640

Arg Pro Asn Gly Lys Thr Trp Ser Thr Lys Arg Pro Ala Ile Ser Pro
                645                 650                 655

Ala Tyr Ser Asn Glu Asn Ala Gln Gly Ser Trp Asn Gly Asp Gln Asp
            660                 665                 670

Ala Gly Pro Leu Leu Val Glu Asn Pro Arg Asp Tyr Ser Thr Glu Leu
        675                 680                 685

Ser Val Thr Ile Ala Val Gly Ala Ser Leu Leu Phe Leu Asn Val Leu
    690                 695                 700

Ala Phe Ala Ala Leu Tyr Tyr Arg Lys Asp Lys Arg Arg Gln Glu Pro
705                 710                 715                 720

Leu Arg Gln Pro Ser Pro Gln Arg Gly Ala Gly Ala Pro Glu Leu Gly
                725                 730                 735

Ala Ala Pro Glu Glu Leu Ala Ala Leu Gln Leu Gly Pro Thr His
            740                 745                 750

His Glu Cys Glu Ala Gly Pro Pro His Asp Thr Leu Arg Leu Thr Ala
        755                 760                 765

Leu Pro Asp Tyr Thr Leu Thr Leu Arg Arg Ser Pro Asp Asp Ile Pro
    770                 775                 780

Leu Met Thr Pro Asn Thr Ile Thr Met Ile Pro Asn Ser Leu Val Gly
785                 790                 795                 800

Leu Gln Thr Leu His Pro Tyr Asn Thr Phe Ala Ala Gly Phe Asn Ser
                805                 810                 815

Thr Gly Leu Pro His Ser His Ser Thr Thr Arg Val
            820                 825

<210> SEQ ID NO 3
<211> LENGTH: 2547
<212> TYPE: DNA
<213> ORGANISM: Rattus norvegicus
<220> FEATURE:
<221> NAME/KEY: CDS
<222> LOCATION: (1)..(2547)

<400> SEQUENCE: 3 atg tgg ctg cag ctc ggc ctg ccc tcg ttg tcc ctg agc ccc acg ccc    48
Met Trp Leu Gln Leu Gly Leu Pro Ser Leu Ser Leu Ser Pro Thr Pro
```

```
                                    -continued
1               5               10              15 aca gtt ggc cgg agc ctg tgc ctc atc ctg tgg ttc ctc agt ttg gtg     96
Thr Val Gly Arg Ser Leu Cys Leu Ile Leu Trp Phe Leu Ser Leu Val
             20              25              30 ctg agg gcc agt acc cag gcc ccg gca ccc aca gtc aat act cac ttt    144
Leu Arg Ala Ser Thr Gln Ala Pro Ala Pro Thr Val Asn Thr His Phe
             35              40              45 ggg aaa cta agg ggt gcc aga gta cca ttg ccc agt gaa atc ctg ggt    192
Gly Lys Leu Arg Gly Ala Arg Val Pro Leu Pro Ser Glu Ile Leu Gly
50              55              60 cct gtg gac caa tac ctg ggg gta ccc tac gca gct ccc ccg atc ggc    240
Pro Val Asp Gln Tyr Leu Gly Val Pro Tyr Ala Ala Pro Pro Ile Gly
65              70              75              80 gag aaa cgt ttc ctg ccc cct gaa cca ccc cca tcc tgg tcg ggc atc    288
Glu Lys Arg Phe Leu Pro Pro Glu Pro Pro Pro Ser Trp Ser Gly Ile
             85              90              95 cgg aac gcc aca cac ttt ccc cca gtg tgc ccc cag aac atc cac aca    336
Arg Asn Ala Thr His Phe Pro Pro Val Cys Pro Gln Asn Ile His Thr
             100             105             110 gct gtg ccc gaa gtc atg ctg cca gtc tgg ttc act gcc aac ttg gat    384
Ala Val Pro Glu Val Met Leu Pro Val Trp Phe Thr Ala Asn Leu Asp
             115             120             125 atc gtc gcc act tat atc cag gag ccc aac gaa gat tgc ctc tat ctg    432
Ile Val Ala Thr Tyr Ile Gln Glu Pro Asn Glu Asp Cys Leu Tyr Leu
             130             135             140 aat gtg tat gtg ccc acg gaa gat gta aag cgg att tcc aag gaa tgc    480
Asn Val Tyr Val Pro Thr Glu Asp Val Lys Arg Ile Ser Lys Glu Cys
145             150             155             160 gcc cga aag ccc aac aag aaa att tgt agg aaa gga gga tcc ggc gct    528
Ala Arg Lys Pro Asn Lys Lys Ile Cys Arg Lys Gly Gly Ser Gly Ala
             165             170             175 aag aaa cag ggc gag gac tta gcg gat aat gac ggg gat gaa gat gaa    576
Lys Lys Gln Gly Glu Asp Leu Ala Asp Asn Asp Gly Asp Glu Asp Glu
             180             185             190 gac atc cga gac agt ggt gct aaa cct gtc atg gtc tac atc cac gga    624
Asp Ile Arg Asp Ser Gly Ala Lys Pro Val Met Val Tyr Ile His Gly
             195             200             205 ggc tct tac atg gaa gga aca ggc aac atg att gac ggc agc gtt ctt    672
Gly Ser Tyr Met Glu Gly Thr Gly Asn Met Ile Asp Gly Ser Val Leu
210             215             220 gca agt tat ggc aac gtc atc gtc atc aca ctc aac tac cgg gtc ggg    720
Ala Ser Tyr Gly Asn Val Ile Val Ile Thr Leu Asn Tyr Arg Val Gly
225             230             235             240 gtg cta ggt ttc ctg agc act ggg gat cag gct gcc aag ggc aac tat    768
Val Leu Gly Phe Leu Ser Thr Gly Asp Gln Ala Ala Lys Gly Asn Tyr
             245             250             255 ggg ctc ctt gat caa atc cag gcc ctt cgc tgg gtg agt gag aac att    816
Gly Leu Leu Asp Gln Ile Gln Ala Leu Arg Trp Val Ser Glu Asn Ile
             260             265             270 gcc ttc ttt gga gga gat ccc cgt aga att act gtc ttt ggc tct ggc    864
Ala Phe Phe Gly Gly Asp Pro Arg Arg Ile Thr Val Phe Gly Ser Gly
             275             280             285 att ggt gca tcc tgt gtc agt ctt ctc aca ctg tct cat cac tct gag    912
Ile Gly Ala Ser Cys Val Ser Leu Leu Thr Leu Ser His His Ser Glu
290             295             300 ggg ctt ttc cag agg gcc atc atc caa agt ggc tca gcg cta tct agc    960
Gly Leu Phe Gln Arg Ala Ile Ile Gln Ser Gly Ser Ala Leu Ser Ser
305             310             315             320 tgg gct gtg aac tac caa cca gtg aag tac acc agc ttg ctc gca gac   1008
Trp Ala Val Asn Tyr Gln Pro Val Lys Tyr Thr Ser Leu Leu Ala Asp
```

-continued

|  |  |  |  |  |  |  |  |  |  |  |  |  |
|---|---|---|---|---|---|---|---|---|---|---|---|---|
|  |  | 325 |  |  |  | 330 |  |  |  | 335 |  |  |
| aaa | gtg | ggc | tgt | aac | gtc | ctg | gac | act | gtg | gat | atg | gtg | gat | tgt | ctt | 1056 |
| Lys | Val | Gly | Cys | Asn | Val | Leu | Asp | Thr | Val | Asp | Met | Val | Asp | Cys | Leu |  |
|  |  | 340 |  |  |  | 345 |  |  |  | 350 |  |  |
| cga | caa | aag | agt | gcc | aag | gag | ctg | gta | gaa | cag | gac | att | cag | cca | gcc | 1104 |
| Arg | Gln | Lys | Ser | Ala | Lys | Glu | Leu | Val | Glu | Gln | Asp | Ile | Gln | Pro | Ala |  |
|  |  | 355 |  |  |  | 360 |  |  |  | 365 |  |  |
| cgc | tac | cat | gtg | gct | ttt | ggc | cct | gtg | att | gat | ggt | gat | gtc | att | cct | 1152 |
| Arg | Tyr | His | Val | Ala | Phe | Gly | Pro | Val | Ile | Asp | Gly | Asp | Val | Ile | Pro |  |
|  | 370 |  |  |  | 375 |  |  |  | 380 |  |  |  |
| gat | gac | cct | gag | atc | ctt | atg | gaa | cag | gga | gag | ttc | ctc | aac | tat | gat | 1200 |
| Asp | Asp | Pro | Glu | Ile | Leu | Met | Glu | Gln | Gly | Glu | Phe | Leu | Asn | Tyr | Asp |  |
| 385 |  |  |  | 390 |  |  |  | 395 |  |  |  | 400 |  |
| atc | atg | cta | ggc | gtc | aac | cag | ggt | gag | ggt | ctc | aag | ttt | gtg | gaa | ggg | 1248 |
| Ile | Met | Leu | Gly | Val | Asn | Gln | Gly | Glu | Gly | Leu | Lys | Phe | Val | Glu | Gly |  |
|  |  |  | 405 |  |  |  | 410 |  |  |  | 415 |  |
| gtg | gtg | gac | ccc | gag | gat | ggt | gtc | tct | ggc | act | gac | ttt | gac | tac | tct | 1296 |
| Val | Val | Asp | Pro | Glu | Asp | Gly | Val | Ser | Gly | Thr | Asp | Phe | Asp | Tyr | Ser |  |
|  |  | 420 |  |  |  | 425 |  |  |  | 430 |  |  |
| gtc | tcc | aat | ttt | gtg | gac | aat | cta | tat | ggc | tat | ccc | gag | ggt | aag | gac | 1344 |
| Val | Ser | Asn | Phe | Val | Asp | Asn | Leu | Tyr | Gly | Tyr | Pro | Glu | Gly | Lys | Asp |  |
|  |  | 435 |  |  |  | 440 |  |  |  | 445 |  |  |
| acc | ctg | cgg | gag | act | atc | aag | ttc | atg | tat | aca | gac | tgg | gca | gac | cga | 1392 |
| Thr | Leu | Arg | Glu | Thr | Ile | Lys | Phe | Met | Tyr | Thr | Asp | Trp | Ala | Asp | Arg |  |
| 450 |  |  |  | 455 |  |  |  | 460 |  |  |  |  |  |
| gac | aac | cct | gag | acc | cgc | cgt | aaa | aca | ctg | gtg | gca | ctc | ttc | act | gac | 1440 |
| Asp | Asn | Pro | Glu | Thr | Arg | Arg | Lys | Thr | Leu | Val | Ala | Leu | Phe | Thr | Asp |  |
| 465 |  |  |  | 470 |  |  |  | 475 |  |  |  | 480 |  |
| cac | cag | tgg | gtg | gag | cct | tcg | gtg | gtg | aca | gct | gat | ctg | cat | gcc | cgc | 1488 |
| His | Gln | Trp | Val | Glu | Pro | Ser | Val | Val | Thr | Ala | Asp | Leu | His | Ala | Arg |  |
|  |  |  | 485 |  |  |  | 490 |  |  |  | 495 |  |
| tat | ggc | tca | ccc | act | tac | ttc | tac | gcc | ttc | tac | cat | cac | tgc | cag | agc | 1536 |
| Tyr | Gly | Ser | Pro | Thr | Tyr | Phe | Tyr | Ala | Phe | Tyr | His | His | Cys | Gln | Ser |  |
|  |  | 500 |  |  |  | 505 |  |  |  | 510 |  |  |
| ctc | atg | aag | cct | gca | tgg | tca | gat | gca | gca | cac | ggg | gat | gaa | gta | ccc | 1584 |
| Leu | Met | Lys | Pro | Ala | Trp | Ser | Asp | Ala | Ala | His | Gly | Asp | Glu | Val | Pro |  |
|  |  | 515 |  |  |  | 520 |  |  |  | 525 |  |  |
| tat | gtt | ttt | ggt | gtc | cct | atg | gta | ggt | ccc | act | gac | ctt | ttc | ccc | tgc | 1632 |
| Tyr | Val | Phe | Gly | Val | Pro | Met | Val | Gly | Pro | Thr | Asp | Leu | Phe | Pro | Cys |  |
|  | 530 |  |  |  | 535 |  |  |  | 540 |  |  |  |
| aac | ttc | tcc | aag | aat | gat | gtt | atg | ctc | agt | gct | gtt | gtt | atg | acc | tat | 1680 |
| Asn | Phe | Ser | Lys | Asn | Asp | Val | Met | Leu | Ser | Ala | Val | Val | Met | Thr | Tyr |  |
| 545 |  |  |  | 550 |  |  |  | 555 |  |  |  | 560 |  |
| tgg | acc | aac | ttt | gcc | aag | acc | ggg | gat | ccc | aac | aag | ccg | gta | ccc | cag | 1728 |
| Trp | Thr | Asn | Phe | Ala | Lys | Thr | Gly | Asp | Pro | Asn | Lys | Pro | Val | Pro | Gln |  |
|  |  | 565 |  |  |  | 570 |  |  |  | 575 |  |  |
| gat | acc | aag | ttc | att | cac | acc | aag | gcc | aac | cgc | ttt | gag | gaa | gta | gcc | 1776 |
| Asp | Thr | Lys | Phe | Ile | His | Thr | Lys | Ala | Asn | Arg | Phe | Glu | Glu | Val | Ala |  |
|  |  | 580 |  |  |  | 585 |  |  |  | 590 |  |  |
| tgg | tcc | aaa | tac | aat | ccc | cgg | gac | cag | ctc | tac | ctt | cac | atc | ggg | ctg | 1824 |
| Trp | Ser | Lys | Tyr | Asn | Pro | Arg | Asp | Gln | Leu | Tyr | Leu | His | Ile | Gly | Leu |  |
|  | 595 |  |  |  | 600 |  |  |  | 605 |  |  |  |
| aaa | cca | agg | gtt | cgt | gat | cat | tac | cga | gcc | aca | aag | gta | gcc | ttt | tgg | 1872 |
| Lys | Pro | Arg | Val | Arg | Asp | His | Tyr | Arg | Ala | Thr | Lys | Val | Ala | Phe | Trp |  |
| 610 |  |  |  | 615 |  |  |  | 620 |  |  |  |  |  |
| aag | cac | ctg | gta | ccc | cat | ctg | tac | aac | ctg | cat | gac | atg | ttc | cac | tat | 1920 |
| Lys | His | Leu | Val | Pro | His | Leu | Tyr | Asn | Leu | His | Asp | Met | Phe | His | Tyr |  |
| 625 |  |  |  | 630 |  |  |  | 635 |  |  |  | 640 |  |
| aca | tcc | acg | acc | acg | aaa | gtg | ccg | ccg | ccg | gac | acc | acc | cat | agc | tcc | 1968 |
| Thr | Ser | Thr | Thr | Thr | Lys | Val | Pro | Pro | Pro | Asp | Thr | Thr | His | Ser | Ser |  |

-continued

```
                       645                 650                 655
cac atc acc cgt agg ccc aac ggc aag acc tgg agc acc aag agg cca       2016
His Ile Thr Arg Arg Pro Asn Gly Lys Thr Trp Ser Thr Lys Arg Pro
            660                 665                 670 gcc atc tca cct gcc tac agc aat gag aat gct cct ggg tcc tgg aat       2064
Ala Ile Ser Pro Ala Tyr Ser Asn Glu Asn Ala Pro Gly Ser Trp Asn
675                 680                 685 ggg gac cag gat gca ggg cca ctc ctg gtc gag aac cct cga gac tac       2112
Gly Asp Gln Asp Ala Gly Pro Leu Leu Val Glu Asn Pro Arg Asp Tyr
        690                 695                 700 tcc act gaa tta agt gtc acc atc gct gtt ggg gcc tct ctc ctg ttt       2160
Ser Thr Glu Leu Ser Val Thr Ile Ala Val Gly Ala Ser Leu Leu Phe
705                 710                 715                 720 ctc aat gtg ttg gcc ttt gct gct ctc tat tac cgt aag gac aaa cgg       2208
Leu Asn Val Leu Ala Phe Ala Ala Leu Tyr Tyr Arg Lys Asp Lys Arg
                725                 730                 735 cgc cag gag ccc ctg agg cag cct agc ccc caa agg gga act ggt gcc       2256
Arg Gln Glu Pro Leu Arg Gln Pro Ser Pro Gln Arg Gly Thr Gly Ala
            740                 745                 750 cca gaa ttg gga act gct cca gag gag gag ctg gca gca tta cag ttg       2304
Pro Glu Leu Gly Thr Ala Pro Glu Glu Glu Leu Ala Ala Leu Gln Leu
        755                 760                 765 ggt ccc act cac cat gag tgt gag gcc ggc ccc cac gac aca ctg            2352
Gly Pro Thr His His Glu Cys Glu Ala Gly Pro His Asp Thr Leu
770                 775                 780 cgc ctc aca gca ttg ccc gac tac acc ctg acc ctg cgg cgc tcc ccc       2400
Arg Leu Thr Ala Leu Pro Asp Tyr Thr Leu Thr Leu Arg Arg Ser Pro
785                 790                 795                 800 gat gac atc cca ctc atg act ccc aac acc atc act atg att ccc aat       2448
Asp Asp Ile Pro Leu Met Thr Pro Asn Thr Ile Thr Met Ile Pro Asn
                805                 810                 815 tcc ctg gtt ggg ttg cag acc ttg cac ccc tat aac acc ttt gcc gcc       2496
Ser Leu Val Gly Leu Gln Thr Leu His Pro Tyr Asn Thr Phe Ala Ala
            820                 825                 830 gga ttc aac agc acc ggg ctg ccc aac tca cac tcc act acc cgt gta       2544
Gly Phe Asn Ser Thr Gly Leu Pro Asn Ser His Ser Thr Thr Arg Val
        835                 840                 845 tag                                                                    2547

<210> SEQ ID NO 4
<211> LENGTH: 848
<212> TYPE: PRT
<213> ORGANISM: Rattus norvegicus

<400> SEQUENCE: 4

Met Trp Leu Gln Leu Gly Leu Pro Ser Leu Ser Leu Ser Pro Thr Pro
1               5                   10                  15

Thr Val Gly Arg Ser Leu Cys Leu Ile Leu Trp Phe Leu Ser Leu Val
            20                  25                  30

Leu Arg Ala Ser Thr Gln Ala Pro Ala Pro Thr Val Asn Thr His Phe
        35                  40                  45

Gly Lys Leu Arg Gly Ala Arg Val Pro Leu Pro Ser Glu Ile Leu Gly
    50                  55                  60

Pro Val Asp Gln Tyr Leu Gly Val Pro Tyr Ala Ala Pro Pro Ile Gly
65                  70                  75                  80

Glu Lys Arg Phe Leu Pro Pro Glu Pro Pro Ser Trp Ser Gly Ile
                85                  90                  95

Arg Asn Ala Thr His Phe Pro Pro Val Cys Pro Gln Asn Ile His Thr
            100                 105                 110
```

```
Ala Val Pro Glu Val Met Leu Pro Val Trp Phe Thr Ala Asn Leu Asp
        115                 120                 125

Ile Val Ala Thr Tyr Ile Gln Glu Pro Asn Glu Asp Cys Leu Tyr Leu
130                 135                 140

Asn Val Tyr Val Pro Thr Glu Asp Val Lys Arg Ile Ser Lys Glu Cys
145                 150                 155                 160

Ala Arg Lys Pro Asn Lys Lys Ile Cys Arg Lys Gly Gly Ser Gly Ala
                165                 170                 175

Lys Lys Gln Gly Glu Asp Leu Ala Asp Asn Asp Gly Asp Glu Asp Glu
            180                 185                 190

Asp Ile Arg Asp Ser Gly Ala Lys Pro Val Met Val Tyr Ile His Gly
        195                 200                 205

Gly Ser Tyr Met Glu Gly Thr Gly Asn Met Ile Asp Gly Ser Val Leu
    210                 215                 220

Ala Ser Tyr Gly Asn Val Ile Val Ile Thr Leu Asn Tyr Arg Val Gly
225                 230                 235                 240

Val Leu Gly Phe Leu Ser Thr Gly Asp Gln Ala Ala Lys Gly Asn Tyr
                245                 250                 255

Gly Leu Leu Asp Gln Ile Gln Ala Leu Arg Trp Val Ser Glu Asn Ile
            260                 265                 270

Ala Phe Phe Gly Gly Asp Pro Arg Arg Ile Thr Val Phe Gly Ser Gly
        275                 280                 285

Ile Gly Ala Ser Cys Val Ser Leu Leu Thr Leu Ser His His Ser Glu
    290                 295                 300

Gly Leu Phe Gln Arg Ala Ile Ile Gln Ser Gly Ser Ala Leu Ser Ser
305                 310                 315                 320

Trp Ala Val Asn Tyr Gln Pro Val Lys Tyr Thr Ser Leu Leu Ala Asp
                325                 330                 335

Lys Val Gly Cys Asn Val Leu Asp Thr Val Asp Met Val Asp Cys Leu
            340                 345                 350

Arg Gln Lys Ser Ala Lys Glu Leu Val Glu Gln Asp Ile Gln Pro Ala
        355                 360                 365

Arg Tyr His Val Ala Phe Gly Pro Val Ile Asp Gly Asp Val Ile Pro
    370                 375                 380

Asp Asp Pro Glu Ile Leu Met Glu Gln Gly Glu Phe Leu Asn Tyr Asp
385                 390                 395                 400

Ile Met Leu Gly Val Asn Gln Gly Glu Gly Leu Lys Phe Val Glu Gly
                405                 410                 415

Val Val Asp Pro Glu Asp Gly Val Ser Gly Thr Asp Phe Asp Tyr Ser
            420                 425                 430

Val Ser Asn Phe Val Asp Asn Leu Tyr Gly Tyr Pro Glu Gly Lys Asp
        435                 440                 445

Thr Leu Arg Glu Thr Ile Lys Phe Met Tyr Thr Asp Trp Ala Asp Arg
    450                 455                 460

Asp Asn Pro Glu Thr Arg Arg Lys Thr Leu Val Ala Leu Phe Thr Asp
465                 470                 475                 480

His Gln Trp Val Glu Pro Ser Val Val Thr Ala Asp Leu His Ala Arg
                485                 490                 495

Tyr Gly Ser Pro Thr Tyr Phe Tyr Ala Phe Tyr His His Cys Gln Ser
            500                 505                 510

Leu Met Lys Pro Ala Trp Ser Asp Ala Ala His Gly Asp Glu Val Pro
        515                 520                 525

Tyr Val Phe Gly Val Pro Met Val Gly Pro Thr Asp Leu Phe Pro Cys
```

```
                530             535             540
Asn Phe Ser Lys Asn Asp Val Met Leu Ser Ala Val Val Met Thr Tyr
545                 550                 555                 560

Trp Thr Asn Phe Ala Lys Thr Gly Asp Pro Asn Lys Pro Val Pro Gln
                565                 570                 575

Asp Thr Lys Phe Ile His Thr Lys Ala Asn Arg Phe Glu Glu Val Ala
                580                 585                 590

Trp Ser Lys Tyr Asn Pro Arg Asp Gln Leu Tyr Leu His Ile Gly Leu
                595                 600                 605

Lys Pro Arg Val Arg Asp His Tyr Arg Ala Thr Lys Val Ala Phe Trp
610                 615                 620

Lys His Leu Val Pro His Leu Tyr Asn Leu His Asp Met Phe His Tyr
625                 630                 635                 640

Thr Ser Thr Thr Thr Lys Val Pro Pro Asp Thr Thr His Ser Ser
                    645                 650                 655

His Ile Thr Arg Arg Pro Asn Gly Lys Thr Trp Ser Thr Lys Arg Pro
                660                 665                 670

Ala Ile Ser Pro Ala Tyr Ser Asn Glu Asn Ala Pro Gly Ser Trp Asn
                675                 680                 685

Gly Asp Gln Asp Ala Gly Pro Leu Leu Val Glu Asn Pro Arg Asp Tyr
690                 695                 700

Ser Thr Glu Leu Ser Val Thr Ile Ala Val Gly Ala Ser Leu Leu Phe
705                 710                 715                 720

Leu Asn Val Leu Ala Phe Ala Ala Leu Tyr Tyr Arg Lys Asp Lys Arg
                725                 730                 735

Arg Gln Glu Pro Leu Arg Gln Pro Ser Pro Gln Arg Gly Thr Gly Ala
                740                 745                 750

Pro Glu Leu Gly Thr Ala Pro Glu Glu Leu Ala Ala Leu Gln Leu
                755                 760                 765

Gly Pro Thr His His Glu Cys Glu Ala Gly Pro Pro His Asp Thr Leu
770                 775                 780

Arg Leu Thr Ala Leu Pro Asp Tyr Thr Leu Thr Leu Arg Arg Ser Pro
785                 790                 795                 800

Asp Asp Ile Pro Leu Met Thr Pro Asn Thr Ile Thr Met Ile Pro Asn
                805                 810                 815

Ser Leu Val Gly Leu Gln Thr Leu His Pro Tyr Asn Thr Phe Ala Ala
                820                 825                 830

Gly Phe Asn Ser Thr Gly Leu Pro Asn Ser His Ser Thr Thr Arg Val
                835                 840                 845

<210> SEQ ID NO 5
<211> LENGTH: 2532
<212> TYPE: DNA
<213> ORGANISM: Rattus norvegicus
<220> FEATURE:
<221> NAME/KEY: CDS
<222> LOCATION: (1)..(2532)

<400> SEQUENCE: 5 atg gca ctt ccc aga tgc atg tgg cca aat tat gtt tgg aga gcc atg      48
Met Ala Leu Pro Arg Cys Met Trp Pro Asn Tyr Val Trp Arg Ala Met
1               5                   10                  15 atg gca tgt gtg gtc cac agg gga tcg ggt gcc ccg ttg act ctc tgc      96
Met Ala Cys Val Val His Arg Gly Ser Gly Ala Pro Leu Thr Leu Cys
            20                  25                  30 ttg ttg gga tgt ctg cta cag act ttc cac gta ctc tct caa aag ttg     144
Leu Leu Gly Cys Leu Leu Gln Thr Phe His Val Leu Ser Gln Lys Leu
```

```
                35                    40                    45
gat gat gta gac cca ttg gtt act act aac ttt ggc aaa ata agg gga      192
Asp Asp Val Asp Pro Leu Val Thr Thr Asn Phe Gly Lys Ile Arg Gly
 50                   55                   60 att aag aaa gaa ctc aat aat gaa att ttg ggg cct gtc att cag ttt      240
Ile Lys Lys Glu Leu Asn Asn Glu Ile Leu Gly Pro Val Ile Gln Phe
 65                   70                   75                   80 ctt ggg gtt cca tat gct gct cca cca aca gga gaa cat cga ttt cag      288
Leu Gly Val Pro Tyr Ala Ala Pro Pro Thr Gly Glu His Arg Phe Gln
                      85                   90                   95 cct cca gaa cca cca tct ccc tgg tct gat atc cgg aat gcc act cag      336
Pro Pro Glu Pro Pro Ser Pro Trp Ser Asp Ile Arg Asn Ala Thr Gln
                     100                  105                  110 ttt gct cct gta tgt ccc cag aat atc att gat ggc aga ttg cct gaa      384
Phe Ala Pro Val Cys Pro Gln Asn Ile Ile Asp Gly Arg Leu Pro Glu
                     115                  120                  125 gtt atg ctt cct gtg tgg ttc act aat aac ttg gat gtg gtt tcc tca      432
Val Met Leu Pro Val Trp Phe Thr Asn Asn Leu Asp Val Val Ser Ser
            130                  135                  140 tat gtg caa gac cag agt gaa gac tgt cta tac tta aac atc tat gtc      480
Tyr Val Gln Asp Gln Ser Glu Asp Cys Leu Tyr Leu Asn Ile Tyr Val
145                  150                  155                  160 cca act gaa gat gta aaa aga ata tcc aag gaa tgt gcc aga aaa ccc      528
Pro Thr Glu Asp Val Lys Arg Ile Ser Lys Glu Cys Ala Arg Lys Pro
                     165                  170                  175 ggc aag aaa ata tgt aga aaa gga gat att cgg gac agt ggg ggt ccc      576
Gly Lys Lys Ile Cys Arg Lys Gly Asp Ile Arg Asp Ser Gly Gly Pro
                180                  185                  190 aaa cca gtg atg gtg tac atc cat ggt ggc tct tac atg gaa ggt act      624
Lys Pro Val Met Val Tyr Ile His Gly Gly Ser Tyr Met Glu Gly Thr
            195                  200                  205 gga aat cta tat gat ggg agt gtg ttg gca agc tac ggt aat gtg atc      672
Gly Asn Leu Tyr Asp Gly Ser Val Leu Ala Ser Tyr Gly Asn Val Ile
210                  215                  220 gtc atc aca gtc aac tat cgg ctt ggg gta ctt ggc ttc ttg agc aca      720
Val Ile Thr Val Asn Tyr Arg Leu Gly Val Leu Gly Phe Leu Ser Thr
225                  230                  235                  240 ggg gat cag gct gcc aaa gga aac tac ggg ctc ctt gac ctc atc cag      768
Gly Asp Gln Ala Ala Lys Gly Asn Tyr Gly Leu Leu Asp Leu Ile Gln
                     245                  250                  255 gcc ctc aga tgg acc agc gag aac att ggg ttc ttt ggt ggt gac ccc      816
Ala Leu Arg Trp Thr Ser Glu Asn Ile Gly Phe Phe Gly Gly Asp Pro
                     260                  265                  270 ttg cga atc acc gtg ttt gga tca ggc gct ggg ggt tca tgt gtc aat      864
Leu Arg Ile Thr Val Phe Gly Ser Gly Ala Gly Gly Ser Cys Val Asn
            275                  280                  285 ctg ctg act tta tcc cat tat tct gaa ggt aac cgt tgg agc aat tca      912
Leu Leu Thr Leu Ser His Tyr Ser Glu Gly Asn Arg Trp Ser Asn Ser
290                  295                  300 acc aaa gga ctt ttt caa cga gca ata gct cag agt gga aca gcc ctt      960
Thr Lys Gly Leu Phe Gln Arg Ala Ile Ala Gln Ser Gly Thr Ala Leu
305                  310                  315                  320 tcc agc tgg gct gtt agt ttc cag cct gca aaa tac gct aga att cta     1008
Ser Ser Trp Ala Val Ser Phe Gln Pro Ala Lys Tyr Ala Arg Ile Leu
                     325                  330                  335 gcc aca aaa gtt ggc tgc aat gtg tca gat aca gta gag tta gta gaa     1056
Ala Thr Lys Val Gly Cys Asn Val Ser Asp Thr Val Glu Leu Val Glu
                340                  345                  350 tgc ctg cag aag aag cct tac aaa gaa ctt gtt gat caa gat gtt caa     1104
Cys Leu Gln Lys Lys Pro Tyr Lys Glu Leu Val Asp Gln Asp Val Gln
```

```
                    -continued
         355            360            365
cca gcc cga tac cac ata gcc ttt gga cct gtg atc gat ggt gat gta   1152
Pro Ala Arg Tyr His Ile Ala Phe Gly Pro Val Ile Asp Gly Asp Val
370             375             380 ata cca gat gac cct cag ata ctg atg gaa caa gga gag ttc ctc aat   1200
Ile Pro Asp Asp Pro Gln Ile Leu Met Glu Gln Gly Glu Phe Leu Asn
385             390             395             400 tat gat atc atg tta gga gtt aac caa ggg gaa ggg ttg aag ttt gtg   1248
Tyr Asp Ile Met Leu Gly Val Asn Gln Gly Glu Gly Leu Lys Phe Val
            405             410             415 gaa aac ata gta gat agt gat gat ggt gta tca gcc agt gat ttt gac   1296
Glu Asn Ile Val Asp Ser Asp Asp Gly Val Ser Ala Ser Asp Phe Asp
        420             425             430 ttt gct gtc tct aat ttt gtt gat aat tta tat gga tat cct gaa ggc   1344
Phe Ala Val Ser Asn Phe Val Asp Asn Leu Tyr Gly Tyr Pro Glu Gly
            435             440             445 aaa gat gtt ttg aga gaa acc att aaa ttc atg tat act gac tgg gct   1392
Lys Asp Val Leu Arg Glu Thr Ile Lys Phe Met Tyr Thr Asp Trp Ala
450             455             460 gat cgc cat aac cct gaa act aga agg aag aca ttg ttg gct ttg ttt   1440
Asp Arg His Asn Pro Glu Thr Arg Arg Lys Thr Leu Leu Ala Leu Phe
465             470             475             480 aca gac cat cag tgg gta gca ccc gct gtg gct aca gca gac ctt cac   1488
Thr Asp His Gln Trp Val Ala Pro Ala Val Ala Thr Ala Asp Leu His
            485             490             495 tcg aac ttt ggc tca cct aca tac ttc tat gcc ttt tat cat cat tgc   1536
Ser Asn Phe Gly Ser Pro Thr Tyr Phe Tyr Ala Phe Tyr His His Cys
        500             505             510 caa act gac caa gtt cca gct tgg gct gat gca gct cat ggg gat gag   1584
Gln Thr Asp Gln Val Pro Ala Trp Ala Asp Ala Ala His Gly Asp Glu
            515             520             525 gtt ccc tat gta ttg gga atc ccc atg att ggc cct aca gag tta ttt   1632
Val Pro Tyr Val Leu Gly Ile Pro Met Ile Gly Pro Thr Glu Leu Phe
530             535             540 cct tgc aat ttc tcc aag aat gat gtg atg ttg agt gct gta gta atg   1680
Pro Cys Asn Phe Ser Lys Asn Asp Val Met Leu Ser Ala Val Val Met
545             550             555             560 aca tac tgg acg aat ttt gct aaa acc ggt gac cca aat caa cca gtt   1728
Thr Tyr Trp Thr Asn Phe Ala Lys Thr Gly Asp Pro Asn Gln Pro Val
            565             570             575 cct caa gac aca aaa ttc att cat acc aaa ccc aac cgc ttt gaa gaa   1776
Pro Gln Asp Thr Lys Phe Ile His Thr Lys Pro Asn Arg Phe Glu Glu
        580             585             590 gta gca tgg acc aga tat tcc cag aaa gac caa ctt tat ctc cat att   1824
Val Ala Trp Thr Arg Tyr Ser Gln Lys Asp Gln Leu Tyr Leu His Ile
            595             600             605 gga tta aaa ccg aga gtt aaa gaa cat tac aga gcc aat aag gta aat   1872
Gly Leu Lys Pro Arg Val Lys Glu His Tyr Arg Ala Asn Lys Val Asn
610             615             620 ctc tgg ttg gag ctg gta cct cat ctg cat aat ctc aat gac att tct   1920
Leu Trp Leu Glu Leu Val Pro His Leu His Asn Leu Asn Asp Ile Ser
625             630             635             640 cag tat acc tcg aca aca act aaa gtg cca tca aca gac atc act ctc   1968
Gln Tyr Thr Ser Thr Thr Thr Lys Val Pro Ser Thr Asp Ile Thr Leu
            645             650             655 aga cct aca agg aaa aat tcc act cca gtc aca tca gcc ttt ccc act   2016
Arg Pro Thr Arg Lys Asn Ser Thr Pro Val Thr Ser Ala Phe Pro Thr
        660             665             670 gcc aag cag gat gat ccc aaa caa caa cca agt ccc ttc tcg gta gat   2064
Ala Lys Gln Asp Asp Pro Lys Gln Gln Pro Ser Pro Phe Ser Val Asp
```

```
                  675                 680                 685
caa agg gac tac tcc aca gag cta agt gtc aca atc gca gtg gga gcc      2112
Gln Arg Asp Tyr Ser Thr Glu Leu Ser Val Thr Ile Ala Val Gly Ala
    690                 695                 700 tct ctg ctg ttt ctg aac atc ttg gct ttt gca gcc cta tac tac aag      2160
Ser Leu Leu Phe Leu Asn Ile Leu Ala Phe Ala Ala Leu Tyr Tyr Lys
705                 710                 715                 720 aaa gac aag agg aga cat gat gtc cac cgg agg tgc agc cct cag cgc      2208
Lys Asp Lys Arg Arg His Asp Val His Arg Arg Cys Ser Pro Gln Arg
                725                 730                 735 acc acg acc aac gac cta acc cat gct cca gaa gag gaa att atg tct      2256
Thr Thr Thr Asn Asp Leu Thr His Ala Pro Glu Glu Glu Ile Met Ser
            740                 745                 750 ctc caa atg aag cac act gac ttg gat cac gag tgt gag tcc atc cat      2304
Leu Gln Met Lys His Thr Asp Leu Asp His Glu Cys Glu Ser Ile His
        755                 760                 765 cca cat gag gtg gtt ctt cgg acc gcc tgc ccc cca gat tat act ctt      2352
Pro His Glu Val Val Leu Arg Thr Ala Cys Pro Pro Asp Tyr Thr Leu
    770                 775                 780 gct atg agg agg tca ccg gat gat gtt cct tta atg aca cct aac acc      2400
Ala Met Arg Arg Ser Pro Asp Asp Val Pro Leu Met Thr Pro Asn Thr
785                 790                 795                 800 atc aca atg att ccc aac act ata cca ggg att cag ccc tta cat aca      2448
Ile Thr Met Ile Pro Asn Thr Ile Pro Gly Ile Gln Pro Leu His Thr
                805                 810                 815 ttc aac aca ttt act gga gga cag aat aat aca ctg ccc cac ccc cac      2496
Phe Asn Thr Phe Thr Gly Gly Gln Asn Asn Thr Leu Pro His Pro His
            820                 825                 830 cct cac ccc cat tca cat tca aca acc agg gta tag                      2532
Pro His Pro His Ser His Ser Thr Thr Arg Val
        835                 840

<210> SEQ ID NO 6
<211> LENGTH: 843
<212> TYPE: PRT
<213> ORGANISM: Rattus norvegicus

<400> SEQUENCE: 6

Met Ala Leu Pro Arg Cys Met Trp Pro Asn Tyr Val Trp Arg Ala Met
1               5                   10                  15

Met Ala Cys Val Val His Arg Gly Ser Gly Ala Pro Leu Thr Leu Cys
            20                  25                  30

Leu Leu Gly Cys Leu Leu Gln Thr Phe His Val Leu Ser Gln Lys Leu
        35                  40                  45

Asp Asp Val Asp Pro Leu Val Thr Thr Asn Phe Gly Lys Ile Arg Gly
    50                  55                  60

Ile Lys Lys Glu Leu Asn Asn Glu Ile Leu Gly Pro Val Ile Gln Phe
65                  70                  75                  80

Leu Gly Val Pro Tyr Ala Ala Pro Pro Thr Gly Glu His Arg Phe Gln
                85                  90                  95

Pro Pro Glu Pro Pro Ser Pro Trp Ser Asp Ile Arg Asn Ala Thr Gln
            100                 105                 110

Phe Ala Pro Val Cys Pro Gln Asn Ile Ile Asp Gly Arg Leu Pro Glu
        115                 120                 125

Val Met Leu Pro Val Trp Phe Thr Asn Asn Leu Asp Val Val Ser Ser
    130                 135                 140

Tyr Val Gln Asp Gln Ser Glu Asp Cys Leu Tyr Leu Asn Ile Tyr Val
145                 150                 155                 160
```

```
Pro Thr Glu Asp Val Lys Arg Ile Ser Lys Glu Cys Ala Arg Lys Pro
            165                 170                 175

Gly Lys Lys Ile Cys Arg Lys Gly Asp Ile Arg Asp Ser Gly Gly Pro
            180                 185                 190

Lys Pro Val Met Val Tyr Ile His Gly Gly Ser Tyr Met Glu Gly Thr
            195                 200                 205

Gly Asn Leu Tyr Asp Gly Ser Val Leu Ala Ser Tyr Gly Asn Val Ile
            210                 215                 220

Val Ile Thr Val Asn Tyr Arg Leu Gly Val Leu Gly Phe Leu Ser Thr
225                 230                 235                 240

Gly Asp Gln Ala Ala Lys Gly Asn Tyr Gly Leu Leu Asp Leu Ile Gln
            245                 250                 255

Ala Leu Arg Trp Thr Ser Glu Asn Ile Gly Phe Phe Gly Gly Asp Pro
            260                 265                 270

Leu Arg Ile Thr Val Phe Gly Ser Gly Ala Gly Gly Ser Cys Val Asn
            275                 280                 285

Leu Leu Thr Leu Ser His Tyr Ser Glu Gly Asn Arg Trp Ser Asn Ser
            290                 295                 300

Thr Lys Gly Leu Phe Gln Arg Ala Ile Ala Gln Ser Gly Thr Ala Leu
305                 310                 315                 320

Ser Ser Trp Ala Val Ser Phe Gln Pro Ala Lys Tyr Ala Arg Ile Leu
            325                 330                 335

Ala Thr Lys Val Gly Cys Asn Val Ser Asp Thr Val Glu Leu Val Glu
            340                 345                 350

Cys Leu Gln Lys Lys Pro Tyr Lys Glu Leu Val Asp Gln Asp Val Gln
            355                 360                 365

Pro Ala Arg Tyr His Ile Ala Phe Gly Pro Val Ile Asp Gly Asp Val
            370                 375                 380

Ile Pro Asp Asp Pro Gln Ile Leu Met Glu Gln Gly Glu Phe Leu Asn
385                 390                 395                 400

Tyr Asp Ile Met Leu Gly Val Asn Gln Gly Glu Gly Leu Lys Phe Val
            405                 410                 415

Glu Asn Ile Val Asp Ser Asp Asp Gly Val Ser Ala Ser Asp Phe Asp
            420                 425                 430

Phe Ala Val Ser Asn Phe Val Asp Asn Leu Tyr Gly Tyr Pro Glu Gly
            435                 440                 445

Lys Asp Val Leu Arg Glu Thr Ile Lys Phe Met Tyr Thr Asp Trp Ala
450                 455                 460

Asp Arg His Asn Pro Glu Thr Arg Arg Lys Thr Leu Leu Ala Leu Phe
465                 470                 475                 480

Thr Asp His Gln Trp Val Ala Pro Ala Val Ala Thr Ala Asp Leu His
            485                 490                 495

Ser Asn Phe Gly Ser Pro Thr Tyr Phe Tyr Ala Phe Tyr His His Cys
            500                 505                 510

Gln Thr Asp Gln Val Pro Ala Trp Ala Asp Ala Ala His Gly Asp Glu
            515                 520                 525

Val Pro Tyr Val Leu Gly Ile Pro Met Ile Gly Pro Thr Glu Leu Phe
            530                 535                 540

Pro Cys Asn Phe Ser Lys Asn Asp Val Met Leu Ser Ala Val Val Met
545                 550                 555                 560

Thr Tyr Trp Thr Asn Phe Ala Lys Thr Gly Asp Pro Asn Gln Pro Val
            565                 570                 575

Pro Gln Asp Thr Lys Phe Ile His Thr Lys Pro Asn Arg Phe Glu Glu
            580                 585                 590
```

-continued

```
Val Ala Trp Thr Arg Tyr Ser Gln Lys Asp Gln Leu Tyr Leu His Ile
            595                 600                 605

Gly Leu Lys Pro Arg Val Lys Glu His Tyr Arg Ala Asn Lys Val Asn
        610                 615                 620

Leu Trp Leu Glu Leu Val Pro His Leu His Asn Leu Asn Asp Ile Ser
625                 630                 635                 640

Gln Tyr Thr Ser Thr Thr Thr Lys Val Pro Ser Thr Asp Ile Thr Leu
            645                 650                 655

Arg Pro Thr Arg Lys Asn Ser Thr Pro Val Thr Ser Ala Phe Pro Thr
        660                 665                 670

Ala Lys Gln Asp Asp Pro Lys Gln Gln Pro Ser Pro Phe Ser Val Asp
675                 680                 685

Gln Arg Asp Tyr Ser Thr Glu Leu Ser Val Thr Ile Ala Val Gly Ala
            690                 695                 700

Ser Leu Leu Phe Leu Asn Ile Leu Ala Phe Ala Ala Leu Tyr Tyr Lys
705                 710                 715                 720

Lys Asp Lys Arg Arg His Asp Val His Arg Arg Cys Ser Pro Gln Arg
            725                 730                 735

Thr Thr Thr Asn Asp Leu Thr His Ala Pro Glu Glu Ile Met Ser
        740                 745                 750

Leu Gln Met Lys His Thr Asp Leu Asp His Glu Cys Glu Ser Ile His
            755                 760                 765

Pro His Glu Val Val Leu Arg Thr Ala Cys Pro Pro Asp Tyr Thr Leu
770                 775                 780

Ala Met Arg Arg Ser Pro Asp Asp Val Pro Leu Met Thr Pro Asn Thr
785                 790                 795                 800

Ile Thr Met Ile Pro Asn Thr Ile Pro Gly Ile Gln Pro Leu His Thr
            805                 810                 815

Phe Asn Thr Phe Thr Gly Gly Gln Asn Asn Thr Leu Pro His Pro His
        820                 825                 830

Pro His Pro His Ser His Ser Thr Thr Arg Val
            835                 840

<210> SEQ ID NO 7
<211> LENGTH: 1329
<212> TYPE: DNA
<213> ORGANISM: homo sapiens
<220> FEATURE:
<221> NAME/KEY: CDS
<222> LOCATION: (1)..(1329)

<400> SEQUENCE: 7 atg tac cag agg atg ctc cgg tgc ggc gcc gag ctg ggc tcg ccc ggg      48
Met Tyr Gln Arg Met Leu Arg Cys Gly Ala Glu Leu Gly Ser Pro Gly
1               5                   10                  15 ggc ggc ggc ggc ggc ggc ggc ggc ggc gca ggg ggg cgc ctg gcc           96
Gly Gly Gly Gly Gly Gly Gly Gly Gly Ala Gly Gly Arg Leu Ala
            20                  25                  30 ctg ctt tgg ata gtc ccg ctc acc ctc agc ggc ctc cta gga gtg gcg     144
Leu Leu Trp Ile Val Pro Leu Thr Leu Ser Gly Leu Leu Gly Val Ala
        35                  40                  45 tgg ggg gca tcc agt ttg gga gcg cac cac atc cac cat ttc cat ggc     192
Trp Gly Ala Ser Ser Leu Gly Ala His His Ile His His Phe His Gly
    50                  55                  60 agc agc aag cat cat tca gtg cct att gca atc tac agg tca ccg gca     240
Ser Ser Lys His His Ser Val Pro Ile Ala Ile Tyr Arg Ser Pro Ala
65                  70                  75                  80
```

-continued

```
tcc ttg cga ggc gga cac gct ggg acg aca tat atc ttt agc aaa ggt       288
Ser Leu Arg Gly Gly His Ala Gly Thr Thr Tyr Ile Phe Ser Lys Gly
            85                  90                  95 ggt gga caa atc acg tat aag tgg cct cct aat gac cga ccc agt aca       336
Gly Gly Gln Ile Thr Tyr Lys Trp Pro Pro Asn Asp Arg Pro Ser Thr
        100                 105                 110 cga gca gac aga ctg gcc ata ggt ttt agc act gtt cag aaa gaa gcc       384
Arg Ala Asp Arg Leu Ala Ile Gly Phe Ser Thr Val Gln Lys Glu Ala
        115                 120                 125 gta ttg gtg cga gtg gac agt tct tca ggc ttg ggt gac tac cta gaa       432
Val Leu Val Arg Val Asp Ser Ser Ser Gly Leu Gly Asp Tyr Leu Glu
130                 135                 140 ctg cat ata cac cag gga aaa att gga gtt aag ttt aat gtt ggg aca       480
Leu His Ile His Gln Gly Lys Ile Gly Val Lys Phe Asn Val Gly Thr
145                 150                 155                 160 gat gac atc gcc att gaa gaa tcc aat gca atc att aat gat ggg aaa       528
Asp Asp Ile Ala Ile Glu Glu Ser Asn Ala Ile Ile Asn Asp Gly Lys
                165                 170                 175 tac cat gta gtt cgt ttc acg agg agt ggt ggc aat gcc acg ttg cag       576
Tyr His Val Val Arg Phe Thr Arg Ser Gly Gly Asn Ala Thr Leu Gln
        180                 185                 190 gtg gac agc tgg cca gtg atc gag cgc tac cct gca ggg cgt cag ctc       624
Val Asp Ser Trp Pro Val Ile Glu Arg Tyr Pro Ala Gly Arg Gln Leu
        195                 200                 205 aca atc ttc aat agc caa gca acc ata ata att ggc ggg aaa gag cag       672
Thr Ile Phe Asn Ser Gln Ala Thr Ile Ile Ile Gly Gly Lys Glu Gln
        210                 215                 220 ggc cag ccc ttc cag ggc cag ctc tct ggg ctg tac tac aat ggc ttg       720
Gly Gln Pro Phe Gln Gly Gln Leu Ser Gly Leu Tyr Tyr Asn Gly Leu
225                 230                 235                 240 aaa gtt ctg aat atg gca gcc gaa aac gat gcc aac atc gcc ata gtg       768
Lys Val Leu Asn Met Ala Ala Glu Asn Asp Ala Asn Ile Ala Ile Val
                245                 250                 255 gga aat gtg aga ctg gtt ggt gaa gtg cct tcc tct atg aca act gag       816
Gly Asn Val Arg Leu Val Gly Glu Val Pro Ser Ser Met Thr Thr Glu
        260                 265                 270 tca aca gcc act gcc atg caa tca gag atg tcc aca tca att atg gag       864
Ser Thr Ala Thr Ala Met Gln Ser Glu Met Ser Thr Ser Ile Met Glu
        275                 280                 285 act acc acg acc ctg gct act agc aca gcc aga aga gga aag ccc ccg       912
Thr Thr Thr Thr Leu Ala Thr Ser Thr Ala Arg Arg Gly Lys Pro Pro
        290                 295                 300 aca aaa gaa ccc att agc cag acc aca gat gac atc ctt gtg gcc tca       960
Thr Lys Glu Pro Ile Ser Gln Thr Thr Asp Asp Ile Leu Val Ala Ser
305                 310                 315                 320 gca gag tgt ccc agc gat gat gag gac att gac ccc tgt gag ccg agc      1008
Ala Glu Cys Pro Ser Asp Asp Glu Asp Ile Asp Pro Cys Glu Pro Ser
                325                 330                 335 tca ggt ggg tta gcc aac cca acc cga gca ggc ggc aga gag ccg tat      1056
Ser Gly Gly Leu Ala Asn Pro Thr Arg Ala Gly Gly Arg Glu Pro Tyr
        340                 345                 350 cca ggc tca gca gaa gtg atc cgg gag tcc agc agc acc acg ggt atg      1104
Pro Gly Ser Ala Glu Val Ile Arg Glu Ser Ser Ser Thr Thr Gly Met
        355                 360                 365 gtc gtt ggg ata gta gcc gct gcc gcc ctg tgc atc ctt atc ctc ctc      1152
Val Val Gly Ile Val Ala Ala Ala Ala Leu Cys Ile Leu Ile Leu Leu
        370                 375                 380 tat gcc atg tac aag tac aga aac cgg gat gaa ggc tca tac cat gtg      1200
Tyr Ala Met Tyr Lys Tyr Arg Asn Arg Asp Glu Gly Ser Tyr His Val
385                 390                 395                 400
```

|                                                                                  |      |
|----------------------------------------------------------------------------------|------|
| gac gag agt cga aac tac atc agt aac tca gca cag tcc aat ggg gct                  | 1248 |
| Asp Glu Ser Arg Asn Tyr Ile Ser Asn Ser Ala Gln Ser Asn Gly Ala                  |      |
|             405                 410                 415                          |      |
| gtt gta aag gag aaa caa ccc agc agt gcg aaa agc tcc aac aaa aat                  | 1296 |
| Val Val Lys Glu Lys Gln Pro Ser Ser Ala Lys Ser Ser Asn Lys Asn                  |      |
|         420                 425                 430                              |      |
| aag aaa aac aag gat aaa gag tat tat gtc tga                                      | 1329 |
| Lys Lys Asn Lys Asp Lys Glu Tyr Tyr Val                                          |      |
|         435                 440                                                  |      |

<210> SEQ ID NO 8
<211> LENGTH: 442
<212> TYPE: PRT
<213> ORGANISM: homo sapiens

<400> SEQUENCE: 8

Met Tyr Gln Arg Met Leu Arg Cys Gly Ala Glu Leu Gly Ser Pro Gly
1               5                   10                  15

Gly Gly Gly Gly Gly Gly Gly Gly Ala Gly Gly Arg Leu Ala
            20                  25                  30

Leu Leu Trp Ile Val Pro Leu Thr Leu Ser Gly Leu Leu Gly Val Ala
        35                  40                  45

Trp Gly Ala Ser Ser Leu Gly Ala His His Ile His His Phe His Gly
    50                  55                  60

Ser Ser Lys His His Ser Val Pro Ile Ala Ile Tyr Arg Ser Pro Ala
65                  70                  75                  80

Ser Leu Arg Gly Gly His Ala Gly Thr Thr Tyr Ile Phe Ser Lys Gly
                85                  90                  95

Gly Gly Gln Ile Thr Tyr Lys Trp Pro Pro Asn Asp Arg Pro Ser Thr
            100                 105                 110

Arg Ala Asp Arg Leu Ala Ile Gly Phe Ser Thr Val Gln Lys Glu Ala
        115                 120                 125

Val Leu Val Arg Val Asp Ser Ser Ser Gly Leu Gly Asp Tyr Leu Glu
    130                 135                 140

Leu His Ile His Gln Gly Lys Ile Gly Val Lys Phe Asn Val Gly Thr
145                 150                 155                 160

Asp Asp Ile Ala Ile Glu Glu Ser Asn Ala Ile Ile Asn Asp Gly Lys
                165                 170                 175

Tyr His Val Val Arg Phe Thr Arg Ser Gly Gly Asn Ala Thr Leu Gln
            180                 185                 190

Val Asp Ser Trp Pro Val Ile Glu Arg Tyr Pro Ala Gly Arg Gln Leu
        195                 200                 205

Thr Ile Phe Asn Ser Gln Ala Thr Ile Ile Gly Gly Lys Glu Gln
    210                 215                 220

Gly Gln Pro Phe Gln Gly Gln Leu Ser Gly Leu Tyr Tyr Asn Gly Leu
225                 230                 235                 240

Lys Val Leu Asn Met Ala Ala Glu Asn Asp Ala Asn Ile Ala Ile Val
                245                 250                 255

Gly Asn Val Arg Leu Val Gly Glu Val Pro Ser Ser Met Thr Thr Glu
            260                 265                 270

Ser Thr Ala Thr Ala Met Gln Ser Glu Met Ser Thr Ser Ile Met Glu
        275                 280                 285

Thr Thr Thr Thr Leu Ala Thr Ser Thr Ala Arg Arg Gly Lys Pro Pro
    290                 295                 300

Thr Lys Glu Pro Ile Ser Gln Thr Thr Asp Asp Ile Leu Val Ala Ser
305                 310                 315                 320

```
Ala Glu Cys Pro Ser Asp Glu Asp Ile Asp Pro Cys Glu Pro Ser
            325                 330                 335

Ser Gly Gly Leu Ala Asn Pro Thr Arg Ala Gly Arg Glu Pro Tyr
            340                 345                 350

Pro Gly Ser Ala Glu Val Ile Arg Glu Ser Ser Ser Thr Thr Gly Met
            355                 360                 365

Val Val Gly Ile Val Ala Ala Ala Leu Cys Ile Leu Ile Leu Leu
            370                 375                 380

Tyr Ala Met Tyr Lys Tyr Arg Asn Arg Asp Glu Gly Ser Tyr His Val
385                 390                 395                 400

Asp Glu Ser Arg Asn Tyr Ile Ser Asn Ser Ala Gln Ser Asn Gly Ala
                405                 410                 415

Val Val Lys Glu Lys Gln Pro Ser Ser Ala Lys Ser Ser Asn Lys Asn
                420                 425                 430

Lys Lys Asn Lys Asp Lys Glu Tyr Tyr Val
            435                 440

<210> SEQ ID NO 9
<211> LENGTH: 663
<212> TYPE: PRT
<213> ORGANISM: Artificial
<220> FEATURE:
<223> OTHER INFORMATION: Fusion Protein

<400> SEQUENCE: 9

Asp Tyr Lys Asp Asp Asp Lys Leu Ala Ala Ala Asn Ser Ser Ile
1               5                   10                  15

Asp Leu Gln Lys Leu Asp Asp Val Asp Pro Leu Val Thr Thr Asn Phe
                20                  25                  30

Gly Lys Ile Arg Gly Ile Lys Lys Glu Leu Asn Asn Glu Ile Leu Gly
            35                  40                  45

Pro Val Ile Gln Phe Leu Gly Val Pro Tyr Ala Ala Pro Pro Thr Gly
            50                  55                  60

Glu His Arg Phe Gln Pro Pro Glu Pro Pro Ser Pro Trp Ser Asp Ile
65              70                  75                  80

Arg Asn Ala Thr Gln Phe Ala Pro Val Cys Pro Gln Asn Ile Ile Asp
                85                  90                  95

Gly Arg Leu Pro Glu Val Met Leu Pro Val Trp Phe Thr Asn Asn Leu
            100                 105                 110

Asp Val Val Ser Ser Tyr Val Gln Asp Gln Ser Glu Asp Cys Leu Tyr
            115                 120                 125

Leu Asn Ile Tyr Val Pro Thr Glu Asp Val Lys Arg Ile Ser Lys Glu
130                 135                 140

Cys Ala Arg Lys Pro Gly Lys Lys Ile Cys Arg Lys Gly Asp Ile Arg
145                 150                 155                 160

Asp Ser Gly Gly Pro Lys Pro Val Met Val Tyr Ile His Gly Gly Ser
                165                 170                 175

Tyr Met Glu Gly Thr Gly Asn Leu Tyr Asp Gly Ser Val Leu Ala Ser
            180                 185                 190

Tyr Gly Asn Val Ile Val Ile Thr Val Asn Tyr Arg Leu Gly Val Leu
            195                 200                 205

Gly Phe Leu Ser Thr Gly Asp Gln Ala Ala Lys Gly Asn Tyr Gly Leu
            210                 215                 220

Leu Asp Leu Ile Gln Ala Leu Arg Trp Thr Ser Glu Asn Ile Gly Phe
225                 230                 235                 240

Phe Gly Asp Pro Leu Arg Ile Thr Val Phe Gly Ser Gly Ala Gly Gly
```

-continued

```
                245                 250                 255
    Ser Cys Val Asn Leu Leu Thr Leu Ser His Tyr Ser Glu Gly Asn Arg
                    260                 265                 270

Trp Ser Asn Ser Thr Lys Gly Leu Phe Gln Arg Ala Ile Ala Gln Ser
                275                 280                 285

Gly Thr Ala Leu Ser Ser Trp Ala Val Ser Phe Gln Pro Ala Lys Tyr
                290                 295                 300

Ala Arg Ile Leu Ala Thr Lys Val Gly Cys Asn Val Ser Asp Thr Val
    305                 310                 315                 320

Glu Leu Val Glu Cys Leu Gln Lys Lys Pro Tyr Lys Glu Leu Val Asp
                    325                 330                 335

Gln Asp Val Gln Pro Ala Arg Tyr His Ile Ala Phe Gly Pro Val Ile
                340                 345                 350

Asp Gly Asp Val Ile Pro Asp Pro Gln Ile Leu Met Glu Gln Gly
                355                 360                 365

Glu Phe Leu Asn Tyr Asp Ile Met Leu Gly Val Asn Gln Gly Glu Gly
                370                 375                 380

Leu Lys Phe Val Glu Asn Ile Val Asp Ser Asp Gly Val Ser Ala
    385                 390                 395                 400

Ser Asp Phe Asp Phe Ala Val Ser Asn Phe Val Asp Asn Leu Tyr Gly
                    405                 410                 415

Tyr Pro Glu Gly Lys Asp Val Leu Arg Glu Thr Ile Lys Phe Met Tyr
                420                 425                 430

Thr Asp Trp Ala Asp Arg His Asn Pro Glu Thr Arg Arg Lys Thr Leu
                435                 440                 445

Leu Ala Leu Phe Thr Asp His Gln Trp Val Ala Pro Ala Val Ala Thr
    450                 455                 460

Ala Asp Leu His Ser Asn Phe Gly Ser Pro Thr Tyr Phe Tyr Ala Phe
    465                 470                 475                 480

Tyr His His Cys Gln Thr Asp Gln Val Pro Ala Trp Ala Asp Ala Ala
                    485                 490                 495

His Gly Asp Glu Val Pro Tyr Val Leu Gly Ile Pro Met Ile Gly Pro
                500                 505                 510

Thr Glu Leu Phe Pro Cys Asn Phe Ser Lys Asn Asp Val Met Leu Ser
                515                 520                 525

Ala Val Val Met Thr Tyr Trp Thr Asn Phe Ala Lys Thr Gly Asp Pro
                530                 535                 540

Asn Gln Pro Val Pro Gln Asp Thr Lys Phe Ile His Thr Lys Pro Asn
    545                 550                 555                 560

Arg Phe Glu Glu Val Ala Trp Thr Arg Tyr Ser Gln Lys Asp Gln Leu
                    565                 570                 575

Tyr Leu His Ile Gly Leu Lys Pro Arg Val Lys Glu His Tyr Arg Ala
                580                 585                 590

Asn Lys Val Asn Leu Trp Leu Glu Leu Val Pro His Leu His Asn Leu
                595                 600                 605

Asn Asp Ile Ser Gln Tyr Thr Ser Thr Thr Lys Val Pro Ser Thr
    610                 615                 620

Asp Ile Thr Leu Arg Pro Thr Arg Lys Asn Ser Thr Pro Val Thr Ser
    625                 630                 635                 640

Ala Phe Pro Thr Ala Lys Gln Asp Pro Lys Gln Gln Pro Ser Pro
                    645                 650                 655

Phe Ser Val Asp Gln Arg Asp
                660
```

METHOD OF PROMOTING DELIVERY OF AN ANTIOXIDANT AGENT TO A CELL EXPRESSION NEUROLIGIN

CROSS REFERENCE TO RELATED APPLICATIONS

This application is filed under 35 U.S.C. §371 and claims priority to International Application Serial No. PCT/US2005/017522, filed May 10, 2005, which claims the benefit under 35 U.S.C. §119 of Provisional Applications No. 60/570,324, filed May 11, 2004, the disclosures of which are incorporated by reference herein.

STATEMENT REGARDING FEDERALLY SPONSORED RESEARCH

The invention was funded in part by Grant No. GM-18360 awarded by the National Institute of Health. The Government may have certain rights in this invention.

TECHNICAL FIELD

This invention relates to methods of diagnosing autism and autism-related diseases/disorders, methods of screening for compounds useful to treat autism and autism-related diseases and disorders and methods of treating autism and autism-related diseases and disorders.

BACKGROUND

Appropriate differentiation and maturation of neurons are essential requirements for synapse formation and achieving patterns of fidelity for cell signaling. Because of the multiplicity of potential targets for any given axon and owing to the asymmetric nature of the synapse, partner recognition is critical for developing and maintaining functional synapses. Improper synapse formation has long been thought to be a cause of autism.

Autism is characterized by a subtle set of behavioral and social abnormalities that appear to be developmentally based. Current therapeutic strategies for the diverse forms of autistic syndromes are solely targeted to the correction of the most severe behavioral problems or symptoms associated with the main disorder. Pharmacological interventions remain a prime candidate for this spectrum of disorders.

SUMMARY

The identification of a mutated form of neuroligin-3 along with its capacity to be retained in the ER (e.g., by chaperon proteins), is provided herein as a novel biological target for disease treatment and the development of a class of molecules with reducing properties that can be used systemically. In one aspect, the invention provides the use of antioxidants targeted at ER oxidoreductases is a novel concept. Ligands that associate within neuroligin, such as neurexin or partner chaperones will promote proper folding of neuroligin and provide targets for stabilizing expressed mutant neuroligins. The invention also provides methods and compositions for enhancing neuroligin expression to augment efficacy of unstable neuroligin molecules.

The invention provide methods of treating autism spectrum disorders comprising targeting an agent to a cell expressing neuroligin, comprising linking the agent to a molecule that interacts with a binding domain of neuroligin. In one aspect, the agent is an antioxidant. For example, the antioxidant can be selected from the group consisting of 2-mercaptoethanol, dithiothreitol, glutathione, S-adenosylmethionine, dithiocarbamate, dimethylsulfoxide, cysteine, methionine, cysteamine, oxo-thiazolidine-carboxylate, timonacic acid, WR-2721, malotilate, 1,2-dithiol 3-thione, 1,3-dithiol 2-thione, lipoamide, sulfarlem, and oltipraz. In another aspect, the cell expresses a neuroligin-1 or a neuroligin-3. In a specific embodiment, the cell comprises a mutated neuroligin-3. For example, the mutated neuroligin-3 comprises SEQ ID NO:2 having an Arg451Cys mutation or SEQ ID NO:4 having an Arg471Cys mutation. In another aspect, the agent is a small molecule resembling the binding surface of neurexin or a neuroligin binding partner that stabilizes expressed or nascent neuroligin. For example, the molecule is a soluble neurexin domain that binds to a neuroligin.

The invention also provides an isolated polynucleotide encoding a polypeptide comprising SEQ ID NO:2 having a cysteine at position 451. In another aspect, the invention comprises fragments of the polynucleotide useful as probes to identify mutations in a nucleic acid that encode a neuroligin-3 having a cysteine at position 451.

The invention also provides an isolated polynucleotide encoding a polypeptide comprising SEQ ID NO:4 having a cysteine at position 471. In another aspect, the invention comprises fragments of the polynucleotide useful as probes to identify mutations in a nucleic acid that encode a neuroligin-3 having a cysteine at position 471.

The invention also provides a substantially purified polypeptide that is at least 95%, 96%, 97%, 98% or 99% identical to SEQ ID NO:2, wherein the polypeptide has a cysteine at position 451.

The invention also provides a substantially purified polypeptide that is at least 95%, 96%, 97%, 98% or 99% identical to SEQ ID NO:4, wherein the polypeptide has a cysteine at position 471.

The invention also provides a polypeptide comprising 1-10 conservative amino acid substitutions to SEQ ID NO:2 or 4 and having a cysteine at position 451 or 471, respectively.

The invention further provides an isolated antibody the specifically binds to SEQ ID NO:2 or 4 and having an Arg to Cys mutation at position 451 or 471.

The invention provides a substantially purified polypeptide or peptidomimetic comprising a soluble fragment of a neurexin that interacts with neuroligin. In one aspect of the invention the polypeptide comprises a sequence VIERYPAGRQL-TIFNSQATIII (SEQ ID NO:8 from about amino acid 198 to 219).

The invention provides a composition comprising an antioxidant linked to a ligand that interacts with a binding domain of a neuroligin. In one aspect, the antioxidant is a sulfur-containing antioxidant is selected from the group consisting of 2-mercaptoethanol, dithiothreitol, glutathione, S-adenosylmethionine, dithiocarbamate, dimethylsulfoxide, cysteine, methionine, cysteamine, oxo-thiazolidine-carboxylate, timonacic acid, WR-2721, malotilate, 1,2-dithiol 3-thione, 1,3-dithiol 2-thione, lipoamide, sulfarlem, and oltipraz. In another aspect, the ligand interacts with a calcium binding domain of neuroligin. In another aspect, the ligand comprises a soluble fragment of neurexin that interacts with a neuroligin.

The invention also provides a method of treating an autism spectrum disorder comprising contacting a subject having or at risk of having such a disorder with a compound that inhibits the intracellular retention of a neuroligin wherein a symptom of the disorder is treated. In one embodiment, the subject is a mammal such as a human. In another aspect, the compound is an antioxidant. In a further aspect, the antioxidant is a sulfur-containing antioxidant. In one aspect, the sulfur-containing antioxidant is selected from the group consisting of 2-mercaptoethanol, dithiothreitol, glutathione, S-adenosylmethionine, dithiocarbamate, dimethylsulfoxide, cysteine, methionine, cysteamine, oxo-thiazolidine-carboxylate, timonacic acid, WR-2721, malotilate, 1,2-dithiol 3-thione, 1,3-dithiol 2-thione, lipoamide, sulfarlem, and oltipraz. In another aspect of the invention, the compound is a soluble peptide or peptidomimetic of neurexin, wherein the compound stabilizes expressed or nascent neuroligin. In a specific embodiment, the soluble peptide comprises a sequence VIERYPAGRQLTIFNSQATIII (SEQ ID NO:8 from about amino acid 198 to 219).

The invention also provides a method of determining the risk of autism in a fetus comprising identifying an Arg451Cys mutation of neuroligin-3 in a biological sample. In a specific embodiment, the invention identifies a mutation in SEQ ID NO:1 giving rise to a polypeptide comprising SEQ ID NO:2 with an Arg451Cys mutation. In another embodiment, the invention utilizes and antibody that specifically binds to a mutant neuroligin-3 comprising an Arg451Cys mutation in SEQ ID NO:2.

The invention provides a method of identifying autism spectrum disorder in a subject comprising identifying an Arg451Cys mutation of neuroligin-3 in a biological sample from the subject. In a specific embodiment, the invention identifies a mutation in SEQ ID NO:1 giving rise to a polypeptide comprising SEQ ID NO:2 with an Arg451Cys mutation. In another embodiment, the invention utilizes and antibody that specifically binds to a mutant neuroligin-3 comprising an Arg451Cys mutation in SEQ ID NO:2.

The invention also provides a non-human transgenic animal comprising a mutant neuroligin-3 wherein the transgenic animal comprises a polynucleotide encoding a polypeptide comprising SEQ ID NO:4 and having an Arg471Cys mutation and wherein the transgenic non-human animal displays behavioral symptoms of autism. In another aspect, the invention provides a cell line derived from the non-human transgenic animal.

The invention further provides a method of screening an agent for use in treating autism spectrum disorders comprising contacting a non-human transgenic animal or a cell line of the invention with the agent and measuring the amount of neuroligin-3 intracellularly in the treated animals compared to a control.

The invention provides a method of screening an agent that inhibits retention of neuroligin-3 intracellularly (or promotes transport to the cell membrane) comprising: contacting a cell comprising a mutant neuroligin-3 with an agent; and measuring the intracellular retention of neuroligin-3 compared to a control cell.

The details of one or more embodiments are set forth in the accompanying drawings and the description below. Other features, objects, and advantages will be apparent from the description and drawings, and from the claims.

DESCRIPTION OF DRAWINGS

FIG. 1 shows a sequence (SEQ ID NO:9) of recombinant NL1 extracellular domain. The entire extracellular domain, devoid of the leader peptide, is shown. The added flag peptide is shown on a black background; the arrow defines the N-terminus of NL1 sequence whose coding begins at residue 46, N-glycosylation consensus sequences are shown in bold type; splice sites are boxed; the Ser-Thr rich region for potential O-linked glycosylation is shown on a gray background; stars indicate the final residue of each of 5 successive truncation mutants; the numbering of the right side indicates NL1 residue number according to the start methionine in the leader peptide. The inserted flag peptide and intervening extension are unnumbered.

FIG. 2A-B shows an SDS polyacrylamide gel, showing the relative migration of the NL1 full-length and two truncated mutants. A: comparison between full-length NL1 purified from detergent extract of the cells and NL1-691 purified from the cell culture medium. B: comparison between two truncated proteins (NL1-638 and NL1-691) purified from the cell extract (ce) and medium (m).

FIG. 22A-B shows synapse formation induced by wildtype and 'autism' mutant neuroligins 1 and 3. A. Formation of synapses from co-cultured hippocampal neurons on COS cells transfected with neuroligins 1 (NL1) and 3 (NL3) and their corresponding mutants (NL1$^{R473C}$ and NL3$^{R471C}$) Assays performed with the chimeric protein NA5 that does not bind to β-neurexins (see FIG. 20) are not illustrated because no synapse formation was observed. B. Synapsin and neuroligin immunofluorescence signals observed over transfected COS cells expressing the indicated proteins (NL1 and NL3=neuroligins 1 and 3; NA-5=acetylcholinesterase/NL1 chimera (see FIG. 18); NL1$^{R473C}$ and NL3$^{R471C}$=autism mutants of NL1 and NL3), and ratio of the signals (columns). Dashed and dotted lines refer to the signals of NL1 as a positive control, and of NA-5 (the inactive acetylcholinesterase/NL1 hybrid) as a negative control.

DETAILED DESCRIPTION

Figure 3:
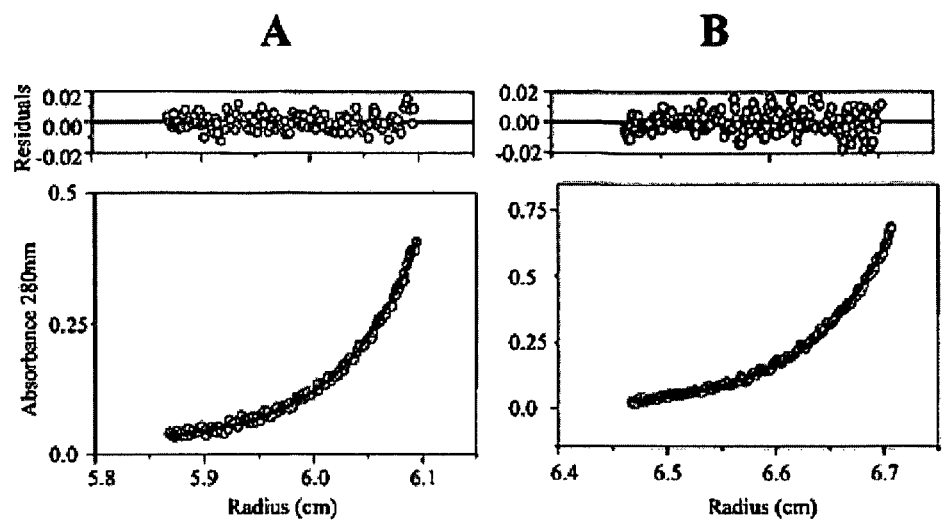
FIG. 3A-B shows an equilibrium ultracentrifugation analysis of NL1. The raw data are shown as circles; the solid line is the "best fit". The distribution of the residuals of the best fit is shown. Data were collected at 10,000 rpm, 20° C., 100 mg/ml NL1 (10 mM Hepes, pH 7.4; 150 mM NaCl). A) NL1-691, mass determined by sedimentation equilibrium: M=179,000. B) NL1-638, mass determined by sedimentation equilibrium: M=159,000.

Neurexin and neuroligin proteins appear to form heterologous cell contacts at synaptic connections and are suitable candidates for controlling synaptic recognition patterns. Neurexin-1-β (NX1β) is a member of a large family of neuronal proteins, composed of at least three genes (neurexins 1 through 3) driven by two promoters (α and β), resulting in the expression of at least six neurexin forms. Alternative mRNA splicing confers additional complexity to the possible gene products.

The neuroligins form a family of cell adhesion proteins encoded by at least five genes that are widely expressed in brain as well as in selected locations outside the central nervous system. Neuroligins are postsynaptic cell-adhesion molecules that bind to NX1β's. Neuroligin binding to NX1β's is regulated by alternative splicing of NX1β's. In transfected cells, neuroligin 1 and NX1β mediate cell adhesion. Neuroligin-1 (NL1) has been localized at post-synaptic densities of glutamatergic synapses; neuroligin-2 is localized to γ-aminobuytric acid synapses. Association between the neurexin-β and neuroligins appears to be Ca$^{2+}$ dependent and selectively blocked by insertion of an alternatively spliced region in NX1β. In brain, neuroligin 1 is localized to postsynaptic densities indicating that postsynaptic neuroligins may form a transsynaptic interactions with presynaptic NX1β.

Neuroligin 1, when expressed in a non-neuronal cells induces presynaptic differentiation in co-cultured pontine explants. Like acetylcholinesterase, neuroligins constitutively dimerize via their extracellular domain. Dimerization of postsynaptic neuroligins may be required for stable association with presynaptic NX1β and/or for activation of presynaptic signaling via β-neurexin binding. Mutations of the putative dimerization sequences of neuroligin 1 abolished its ability to form synapses, and addition of agents that bind to NX1β's-immobilized recombinant neuroligin 1 or antibodies to epitope tagged transfected neurexins—promote the clustering of synaptic vesicle antigens in cultured neurons.

Mutations in neuroligin-3 and 4 are linked to autistic spectrum disorders in man. Consistent with the hypothesis that NX1β and NL1 can mediate the assembly of the pre- and postsynaptic terminals the disruption of functional neuroligin-3 poses a risk for proper synaptic formation.

Neuroligins have structural features typical of other type I cell surface receptors with an extended N-terminal globular region, an O-linked carbohydrate rich domain linked to the single transmembrane region and C-terminal cytoplasmic domain containing a PDZ recognition sequence. The N-terminal domain of NL1 consisting of 695 residues has an α/β-hydrolase fold that is characteristic of the cholinesterases and many other serine hydrolases. The NL1 extracellular domain contains two regions of alternative splicing: the first (residues 165-184) has a net charge of +8 and a potential disulfide bond formed between cysteines at positions 172 and 181; the second (residues 298-305) contains an N-glycosylation consensus sequence at Asn303. NL1 contains a total of five potential N-glycosylation sites throughout the extracellular domain and, in the stalk region, a Ser-Thr rich module that is likely to be highly O-glycosylated. The extracellular domain of NL1 between the leader peptide and residue 638 shares ~34% residue identity with acetylcholinesterase (AChE) and likely the same α/β-hydrolase fold.

Rodents have at least three neuroligin genes, but humans have five neuroligin genes. The invention is based, at least in part, upon the identification of missense mutation in human neuroligin 3 (Arg451Cys mutation in SEQ ID NO:2). The Arg471Cys mutation in rat neuroligin 3 (SEQ ID NO:4) (which corresponds to the human Arg451Cys substitution) causes at least partial retention of neuroligin 3 in the endoplasmic reticulum. Human and Rat neuroligin 3 polynucleotide and polypeptide sequences are set forth in SEQ ID Nos: 1-4, respectively.

Although substantial evidence has accrued for a genetic linkage to autism spectrum disorders, the absence of an altered function in a defined gene product is a major limitation in understanding the pathogenesis of the disorder. The invention provides such a link and provides compositions and methods for early detection of autism and autism-like disorders as well as therapeutic compositions and methods to treat such disorders. The invention provides data on how neuroligin-3 polymorphisms, discovered in man, are associated with autism spectrum disorders.

Neuroligins bind, in the presence of calcium, to neurexins. The Arg451Cys mutation identified in neuroligin 3 was hypothesized to cause a disruption of the potential calcium binding domain present in neuroligin. However, the invention demonstrates that the mutation mainly affected the posttranslational processing of the protein causing intracellular retention of the mutated protein and a decrease in its neurexin affinity. In addition, the protein is disulfide bonded with other proteins (e.g., chaperones) and retained in the endoplasmic reticulum. Because of this retention of neuroligin-3 intracellularly proper synaptic formation is prevented.

The invention provides a method of treating and/or preventing autism, autism-like disorders, and/or symptoms using antioxidants as therapeutic agents. Such agents are useful to reverse the disulfide bonding with intracellular proteins (e.g., chaperones) thereby reducing the retention of the mutated neuroligin in the endoplasmic reticulum (ER). Autism and autism-like disorders include, for example, familial forms of autism, mental retardation, and/or Asperger syndrome.

By delivery of agents that modulate red-ox in a cell (e.g., an agent such as acetaminophen) autistic disorders caused by the Cys substitution mutation (discussed herein) can be modulated. For example, it is possible to take advantage of administration of antioxidants that can prevent the detrimental effects resulting from the lack of surface delivery of the mutated protein and/or help restore the neuroligin function by virtue of the larger delivery of the defective protein to the synapse.

In yet another aspect of the invention, a method of treating autism and autism-like disorders is provided by targeting antioxidants to areas and tissues that comprise mutated neuroligin. For example, by site directing the antioxidants to areas of neuroligin biosynthesis antioxidant toxicity would be minimized.

A drug properly targeted to the central nervous system, to the endoplasmic reticulum or directly to neuroligin (for instance by mean of its affinity for the calcium ion), can reduce the amount of retained protein, thus restoring function of the mutated protein of neuroligin to migrate to the cell surface and assist in synaptic formation.

This disclosure provides methods and compositions for treating autism spectrum disorders by administering an antioxidant or neuroligin stabilizing agents. In one aspect, the antioxidant is a sulfur-containing antioxidant, e.g., those which contain a sulfhydryl group such as PDTC and NAC. In addition to PDTC and NAC, the class of sulfur-containing antioxidants includes, but is not limited to, 2-mercaptoethanol, dithiothreitol, glutathione, S-adenosylmethionine, dithiocarbamate, propylthiouracil, dimethylsulfoxide, cysteine, methionine, cysteamine, oxo-thiazolidine-carboxylate, timonacic acid, WR-2721, malotilate, 1,2-dithiol 3-thione, 1,3-dithiol 2-thione, lipoamide, sulfarlem, and oltipraz. These and other sulfur-containing antioxidants, as well as antioxidants which do not contain sulfur, may be tested in vitro for their ability to modify the secretion of neuroligin, e.g., incubating cells comprising a mutant neuroligin (e.g., mutant neuroligin-3) with the test compound and detecting neuroligin in the endoplasmic reticulum. Furthermore, such agents can be tested in vivo in a rat transgenic model provided herein.

Antioxidants or neuroligin stabilizing agents can be administered to a subject, e.g., systemically such as orally, intravenously, intraperitoneally, intracerebrally, epiderally, or locally such as during a surgical procedure.

In one aspect, the disclosure teaches a site-specific delivery of the antioxidant to the endoplasmic reticulum (ER) to reverse incorrect disulfide binding of the protein neuroligin. In a further aspect, because neuroligins bind, in presence of calcium, to neurexins and because a point mutation in the neuroligin-3 gene that mutated Arg451 to a Cys causes intracellular retention of the mutated protein and a decrease in its neurexin affinity, delivery of an antioxidant such as, for example, cysteamine enables the mutated form of neuroligin-3 to reach the cell surface, where it is needed to bind with neurexin.

In another aspect, the antioxidant is targeted to neuroligin by using the calcium binding site or other recognition area to direct the antioxidant to neuroligin. For example, the antioxidant (e.g., cysteamine) would be linked to a site directed molecule which binds to the calcium binding or other recognition site. In another embodiment, peptidomimetic compounds resembling the recognition region of neurexin or other neuroligin associating molecules will be used to stabilize the aberrant neuroligin gene product. For example, the neuroligin-neurexin complex is more stable that is free neuroligin. Therefore it is possible to stabilize the aberrant or mutant neuroligin by contacting the mutant neuroligin (in vitro or in vivo) with a polypeptide, peptide or peptidomimetic that resembles the binding region of neurexin in the complex. Hence, this would stabilize and encourage proper folding of the mutant neuroligin. Also, by enhancing expression of neuroligins, the invention provides an alternative means of compensating for a deficiency in the mutant neuroligin. Since removing splice site 2 can enhance neuroligin binding, this might provide a means for compensating for low expression or an unstably expressed neuroligin.

The compounds (antioxidant active ingredients) of this invention can be formulated and administered to treat autism spectrum disorders/disease by any means that produces contact of the active ingredient with the site of action in the body of a vertebrate (e.g., in the neuronal cells comprising a mutated neuroligin). The formulations and administrative routes described herein are applicable to both small molecule therapeutics as well as the delivery of some nucleic acids (gene therapy agents) described elsewhere herein. They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

The dosage administered will be a therapeutically effective amount of active ingredient and will, of course, vary depending upon known factors such as the pharmacodynamic characteristics of the particular active ingredient and its mode and route of administration; age, sex, health and weight of the recipient; nature and extent of symptoms; kind of concurrent treatment, frequency of treatment and the effect desired.

The active ingredient can be administered orally in solid dosage forms such as capsules, tablets and powders, or in liquid dosage forms such as elixirs, syrups, emulsions and suspensions. The active ingredient can also be formulated for administration parenterally by injection, rapid infusion, nasopharyngeal absorption or dermoabsorption. The agent may be administered intramuscularly, intravenously, subcutaneously, transdermally, intracranially or as a suppository.

Gelatin capsules contain the active ingredient and powdered carriers such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration typically contain a water soluble salt of the active ingredient, suitable stabilizing agents and, if necessary, buffer substances. Antioxidizing agents (in addition to the active ingredient) such as sodium bisulfate, sodium sulfite or ascorbic acid, either alone or combined, are suitable stabilizing agents. Also used are citric acid and its salts and sodium Ethylenediaminetetraacetic acid (EDTA). In addition, parenteral solutions can contain preservatives such as benzalkonium chloride, methyl- or propyl-paraben and chlorobutanol. Suitable pharmaceutical carriers are described in Remington's Pharmaceutical Sciences, a standard reference text in this field.

Additionally, standard pharmaceutical methods can be employed to control the duration of action. These are well known in the art and include control release preparations and can include appropriate macromolecules, for example polymers, polyesters, polyamino acids, polyvinyl, pyrolidone, ethylenevinylacetate, methyl cellulose, carboxymethyl cellulose or protamine sulfate. The concentration of macromolecules as well as the methods of incorporation can be adjusted in order to control release. Additionally, the agent can be incorporated into particles of polymeric materials such as polyesters, polyamino acids, hydrogels, poly (lactic acid) or ethylenevinylacetate copolymers. In addition to being incorporated, these agents can also be used to trap the compound in microcapsules.

The pharmaceutical composition of the invention may be delivered via various routes and to various sites to achieve a particular effect. One skilled in the art will recognize that although more than one route can be used for administration, a particular route can provide a more immediate and more effective reaction than another route. Local or systemic delivery can be accomplished by administration comprising application or instillation of the formulation into body cavities, inhalation or insufflation of an aerosol, or by parenteral introduction, comprising intramuscular, intravenous, peritoneal, subcutaneous, intradermal, intracranial, epidural administration as well as topical administration.

The composition of the invention can be provided in unit dosage form wherein each dosage unit, e.g., a teaspoonful, tablet, solution, or suppository, contains a predetermined amount of the composition, alone or in appropriate combination with other active agents. The term "unit dosage form" as used herein refers to physically discrete units suitable as unitary dosages for human and animal subjects, each unit containing a predetermined quantity of the compositions of the invention, alone or in combination with other active agents, calculated in an amount sufficient to produce the desired effect, in association with a pharmaceutically acceptable diluent, carrier, or vehicle, where appropriate. The specifications for the unit dosage forms of the invention depend on the particular effect to be achieved and the particular pharmacodynamics associated with the pharmaceutical composition in the particular host.

These methods described herein are by no means all-inclusive, and further methods to suit the specific application will be apparent to the ordinary skilled artisan. Moreover, the effective amount of the compositions can be further approximated through analogy to compounds known to exert the desired effect.

The term "therapeutically effective" as used herein is defined as the amount of a compound required to improve some symptom associated with a disease. For example, in the treatment of autism, a compound which decreases, prevents, delays, or arrests any symptom of autism would be therapeutically effective. A therapeutically effective amount of a compound is not required to cure a disease but will provide a treatment for a disease. For example, a therapeutically effective amount would be that amount that reduces or eliminates behavioral symptoms associated with autism.

The invention has identified a genetic mutation associated with autism. Accordingly, the invention provides genetic therapy/gene delivery techniques to treat subject having such a genetic mutation in order to treat and/or reduce the risk of developing autism and autism-like disorders. In addition, the invention provides recombinant molecular biology compositions and methods useful in the study and treatment of autism and autism-like diseases/disorders.

The term "polynucleotide" generally refers to at least one molecule or strand of DNA, RNA or a derivative or mimic thereof, comprising at least one nucleobase, such as, for example, a naturally occurring purine or pyrimidine base found in DNA (e.g. adenine "A," guanine "G," thymine "T" and cytosine "C") or RNA (e.g. A, G, uracil "U" and C). The term "polynucleotide" encompass the terms "oligonucleotide" and "nucleic acid." These definitions generally refer to at least one single-stranded molecule, but in specific embodiments will also encompass at least one additional strand that is partially, substantially or fully complementary to the at least one single-stranded molecule. Thus, a polynucleotide may encompass at least one double-stranded molecule or at least one triple-stranded molecule that comprises one or more complementary strand(s) or "complement(s)" of a particular polynucleotide comprising a strand of the molecule.

A polynucleotide may be made by any technique known to one of ordinary skill in the art. Non-limiting examples of synthetic polynucleotide, particularly a synthetic oligonucleotide, include a polynucleotide made by in vitro chemically synthesis using phosphotriester, phosphite or phosphoramidite chemistry and solid phase techniques, or via deoxynucleoside H-phosphonate intermediates. A non-limiting example of enzymatically produced polynucleotide include one produced by enzymes in amplification reactions such as PCR. A non-limiting example of a biologically produced polynucleotide includes recombinant nucleic acid production in living cells, such as recombinant DNA vector production in bacteria.

The polynucleotide(s) of the invention, regardless of the length, may be combined with other polynucleotides, including but not limited to, promoters, enhancers, polyadenylation signals, restriction enzyme sites, multiple cloning sites, coding segments, and the like, to create one or more polynucleotide construct(s).

In certain embodiments, the polynucleotide construct is a recombinant vector. As used herein, a "recombinant vector" is a nucleic acid molecule comprising different polynucleotide segments including at least one polynucleotide of interest, wherein the vector is utilized for transmittal of the polynucleotide of interest between biological entities, such as between cells, between tissues, or even between laboratory container, such as an eppendorf tube or test tube, and a cell.

The invention provides isolated polynucleotides comprising SEQ ID NO:1 or 3 encoding a neuroligin polypeptide an Arg451Cys mutation or an Arg471Cys mutation, respectively. In addition, the invention provides probes and primers that are useful in identifying Arg to Cys mutations in neuroligin-3. In one aspect, the probe comprises polynucleotide of at least 7 nucleotides (e.g., 7, 10, 20, 50, 100 nucleotides) that selectively hybridizes to SEQ ID NO:1 and/or 3 wherein Arg451 is Cys or Arg471 is Cys (human or rat, respectively). In a more specific embodiment the probe comprises nucleotides from about 1342 to about 1356 of SEQ ID NO:1 or from about 1405 to about 1419 of SEQ ID NO:3, wherein the codon CGT comprising nucleotide 1351 to 1353 of SEQ ID NO:1 and 1411 to 1413 of SEQ ID NO:3 encodes a cysteine (e.g., comprises TGT or TGC). In another aspect, the probe comprises an antibody that specifically binds to a mutant form of neuroligin-3 comprising an Arg451Cys mutation, but not the wild-type neuroligin-3.

Vectors are routinely used in the art to manipulate, transfer and express nucleic acids. Typically a polynucleotide is inserted into a vector for introduction into a cell where it can be replicated and/or expressed. Typically the polynucleotide is "exogenous," which means that it is foreign to the cell into which the vector is being introduced or that the polynucleotide is homologous to a sequence in the cell but in a position within the host cell where the polynucleotide is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Maniatis et al., 1988 and Ausubel et al., 1994, both incorporated herein by reference.

The term "expression vector" refers to a vector containing a polynucleotide coding for at least part of a gene product capable of being transcribed. In some cases, RNA molecules are then translated into a protein, polypeptide, or peptide. In other cases, the polynucleotides are not translated, for example, in the production of antisense molecules or ribozymes. Expression vectors can contain a variety of "control elements," which refer to elements necessary for the transcription and possibly translation of a coding sequence in a particular host organism. In addition to control elements that govern transcription and translation, vectors and expression vectors may contain polynucleotides that serve other functions as well.

A "promoter" is a control element at which initiation and rate of transcription are controlled. It may contain genetic elements at which regulatory proteins and molecules may bind such as RNA polymerase and other transcription factors.

The promoter is in a correct functional location and/or orientation in relation to a polynucleotide to control transcriptional initiation and/or expression of that polynucleotide. A promoter may or may not be used in conjunction with an "enhancer," which refers to a cis-acting regulatory sequence involved in the transcriptional activation of a polynucleotide.

A promoter may be one naturally associated with a gene, as may be obtained by isolating the 5' non-coding region located upstream of the coding segment and/or exon. Such a promoter can be referred to as "endogenous." Similarly, an enhancer may be one naturally associated with a polynucleotide, located either downstream or upstream. Alternatively, certain advantages will be gained by positioning the coding polynucleotide segment under the control of a recombinant or heterologous promoter, which refers to a promoter that is not normally associated with a polynucleotide in its natural environment. A recombinant or heterologous enhancer refers also to an enhancer not normally associated with a polynucleotide in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing polynucleotides of promoters and enhancers synthetically, such molecules may be produced using recombinant cloning and/or nucleic acid amplification technology, including PCR. Furthermore, it is contemplated the control elements that direct transcription and/or expression within non-nuclear organelles such as mitochondria, chloroplasts, and the like, can be employed as well.

Naturally, it will be important to employ a promoter and/or enhancer that effectively directs the expression of the polynucleotide in the cell type, organelle, and organism chosen for expression. Those of skill in the art of molecular biology generally know the use of promoters, enhancers, and cell type combinations for protein expression, for example, see Sambrook et al. The promoters employed may be constitutive, tissue-specific, inducible, and/or useful under the appropriate conditions to direct high level expression of the introduced polynucleotide, such as is advantageous in the large-scale production of recombinant proteins and/or peptides. The promoter may be heterologous or endogenous.

In certain embodiments of the invention, the cells contain a nucleic acid construct of the invention (e.g., a neuroligin-3 comprising an Arg451Cys (human) or Arg471Cys (rat) mutant). Such host cells comprising mutant neuoligins are useful for screening compounds that modify the intracellular retention of the neuroligin. Vectors used to modify transfect such host cells typically carry selectable markers. A cell may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is calorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous polynucleotide, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

Host cells may be derived from prokaryotes or eukaryotes, depending upon whether the desired result is replication of the vector or expression of part or all of the vector-encoded polynucleotides. Numerous cell lines and cultures are available for use as a host cell, and they can be obtained through the American Type Culture Collection (ATCC), which is an organization that serves as an archive for living cultures and genetic materials. An appropriate host can be determined by one of skill in the art based on the vector backbone and the desired result. A plasmid or cosmid, for example, can be introduced into a prokaryote host cell for replication of many vectors.

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control elements that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

Numerous expression systems exist that comprise at least a part or all of the compositions discussed above. Prokaryote- and/or eukaryote-based systems can be employed for use with the invention to produce polynucleotides, or their cognate polypeptides, proteins and peptides. Many such systems are commercially and widely available.

The invention also provides methods of detecting a neuroligin-3 polynucleotide comprising an Arg-Cys mutation as described herein. For example, the polynucleotides, host cells and vectors are useful in the preparation of primers and probes. For example, they have utility as probes or primers for embodiments involving nucleic acid hybridization in screening assays and the like.

The use of a probe or primer of between 13 and 100 nucleotides, typically between 17 and 50 nucleotides in length, allows the formation of a duplex molecule that is both stable and selective. Molecules having complementary sequences over contiguous stretches greater than 20 bases in length are useful to increase stability and/or selectivity of the hybrid molecules obtained. One will generally design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production. Such primers and probes can be designed based upon the sequences provided in SEQ ID NO:1 and 3.

Accordingly, the polynucleotides of the invention may be used for their ability to selectively form duplex molecules with complementary stretches of DNAs and/or RNAs or to provide primers for amplification of DNA or RNA from samples. Depending on the application envisioned, one would desire to employ varying conditions of hybridization to achieve varying degrees of selectivity of the probe or primers for the target sequence.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

In certain embodiments, it will be advantageous to employ polynucleotides of the invention in combination with an appropriate means, such as a label, for determining hybridization. A wide variety of appropriate indicator means are known in the art, including fluorescent, radioactive, enzymatic or other ligands, such as avidin/biotin, which are capable of being detected. In some embodiments, a polynucleotide (e.g., a nucleic acid probe or primer) can be selectively located on a chip for rapid screening of various genetic disorders. Chip technology is commonly used to screen biological samples. Commercially available chips for gene screening are available from Affymetrix, Inc. Accordingly, the invention provides a polynucleotide of the invention or a fragment thereof comprising an Arg to Cys mutation on a DNA chip. For example, the invention provides a chip comprising a polynucleotide that is at least 15 nucleotides in length of SEQ ID NO:1 and comprises nucleotides 1351-1352 of SEQ ID NO:1, wherein the codon encodes a cysteine (e.g., from about 1345-1360 of SEQ ID NO:1). One of skill in the art will recognize that the size and sequence of the polynucleotide can vary and the invention is intended to encompass such variation so long as the polynucleotide on the chip comprises a sequence capable of identifying an Arg451Cys mutation. Similar polynucleotides and fragments of SEQ ID NO:3 can be used.

In general, it is envisioned that the probes or primers described herein will be useful as reagents in hybridization techniques, as in PCR, for detection of expression of corresponding genes, as well as in embodiments employing a solid phase. In embodiments involving a solid phase, the probe (e.g., DNA or RNA) comprising SEQ ID NO:1 or 3 or a fragment thereof encoding an Arg-Cys mutation as described above is adsorbed or otherwise affixed to a selected matrix or surface. This fixed, single-stranded polynucleotide is then subjected to hybridization with selected probes under desired conditions. The conditions selected will depend on the particular circumstances (depending, for example, on the G+C content, type of target nucleic acid, source of nucleic acid, size of hybridization probe, and the like). Optimization of hybridization conditions for the particular application of interest is well known to those of skill in the art. After washing of the hybridized molecules to remove non-specifically bound molecules, hybridization is detected, and/or quantified, by determining the amount of label. Representative solid phase hybridization methods are known in the art.

Nucleic acids used as a template for amplification may be isolated from cells, tissues or other samples according to standard methodologies (Sambrook et al., 1989). In certain embodiments, analysis is performed on whole cell or tissue homogenates or biological fluid samples (e.g., amniotic fluid) without substantial purification of the template nucleic acid. The nucleic acid may be genomic DNA or fractionated or whole cell RNA. Where RNA is used, it may be desired to first convert the RNA to a complementary DNA.

A reverse transcriptase PCR amplification procedure may be performed to quantify the amount of mRNA amplified. Methods of reverse transcribing RNA into cDNA are well known and described in Sambrook et al., 1989. Alternative methods for reverse transcription utilize thermostable DNA polymerases. Polymerase chain reaction methodologies are well known in the art. Representative methods of RT-PCR are described in U.S. Pat. No. 5,882,864.

Following any amplification, it may be desirable to separate the amplification product from the template and/or the excess primer. In one embodiment, amplification products are separated by agarose, agarose-acrylamide or polyacrylamide gel electrophoresis using standard methods (Sambrook et al., 1989). Separated amplification products may be cut out and eluted from the gel for further manipulation. Using low melting point agarose gels, the separated band may be removed by heating the gel, followed by extraction of the nucleic acid.

Separation of nucleic acids may also be effected by chromatographic techniques known in art. There are many kinds of chromatography which may be used in the practice of the invention, including adsorption, partition, ion-exchange, hydroxylapatite, molecular sieve, reverse-phase, column, paper, thin-layer, and gas chromatography as well as HPLC. In another aspect, the amplification products are then subject to hybridization to a DNA-chip as described above.

In particular embodiments, detection is by Southern blotting and hybridization with a labeled probe. The techniques involved in Southern blotting are well known to those of skill in the art. See Sambrook et al., 1989.

One method of screening for point mutations in neuroligin-3 is based on RNase cleavage of base pair mismatches in RNA/DNA or RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single or multiple base point mutations.

All the essential materials and/or reagents required for detecting a mutation of neuroligin-3 associated with autism and autism-like disorders may be assembled together in a kit. Additional reagents can be included to identify mutations in other gene (e.g., neuroligin-1, -4 and the like). This generally will comprise a probe (nucleic acid or antibody) or primers designed to hybridize specifically to individual nucleic acids of interest in the practice of the invention, including a neuroligin-3 having a sequence as set forth in SEQ ID NO:1, but encoding a Cys at position 451 of SEQ ID NO:2. Also included may be enzymes suitable for amplifying nucleic acids, including various polymerases (reverse transcriptase, Taq, and the like), deoxynucleotides and buffers to provide the necessary reaction mixture for amplification. Such kits may also include enzymes and other reagents suitable for detection of specific nucleic acids or amplification products or labeling of bound antibodies. Such kits generally will comprise, in suitable means, distinct containers for each individual reagent or enzyme as well as for each probe or primer pair.

The invention also provides transgenic animals useful to study autism and autism-like disorders resulting from improper post-translational processing of neuroligin (e.g., retention of neuroligin-3 intracellularly). "Transgenic animal" refers to an animal to which exogenous DNA has been introduced while the animal is still in its embryonic stage. In most cases, the transgenic approach aims at specific modifications of the genome. The targeted character of certain of these procedures sets transgenic technologies apart from experimental methods in which random mutations are conferred to the germline, such as administration of chemical mutagens or treatment with ionizing solution. Typically, the genome of the transgenic non-human mammal comprises one or more mutations in a gene and further comprises a heterologous selectable marker gene.

The term "heterozygote," "heterozygotic mammal" and the like, refers to a transgenic mammal with a mutation on one of a chromosome pair in all of its genome-containing cells.

The term "homozygote," "homozygotic mammal" and the like, refers to a transgenic mammal with a mutation on both members of a chromosome pair in all of its genome-containing cells.

In principle, transgenic animals may have one or both copies of the gene sequence of interest mutated. In the latter case, in which a homozygous mutation is present, the mutation is sometimes referred to as a "null" mutation in that both genes of the organism produce a non-functional protein. In the case where only one copy of the nucleic acid sequence of interest is disrupted, the transgenic animal is termed a "heterozygous animal".

A "non-human animal" of the invention includes mammals such as rodents, non-human primates, sheep, dog, cow, chickens, amphibians, reptiles, and the like. Typical non-human animals are selected from the rodent family including rat and mouse, though transgenic amphibians, such as members of the *Xenopus* genus, and transgenic chickens can also provide important tools for understanding and identifying agents which can affect, for example, protein function and disease models.

Techniques for obtaining the transgenic animals of the invention are well known in the art; the techniques for introducing foreign DNA sequences into the mammalian germ line were originally developed in mice. One route of introducing foreign DNA into a germ line entails the direct microinjection of linear DNA molecules into a pronucleus of a fertilized one-cell egg. Microinjected eggs are subsequently transferred into the oviducts of pseudopregnant foster mothers and allowed to develop. About 25% of the progeny mice inherit one or more copies of the micro-injected DNA. Currently, the most frequently used techniques for generating chimeric and transgenic animals are based on genetically altered embryonic stem cells or embryonic germ cells. Techniques suitable for obtaining transgenic animals have been amply described. A suitable technique for obtaining completely ES cell derived transgenic non-human animals is described in WO 98/06834.

A "targeting vector" is a vector comprising a polynucleotide of interest (e.g., a mutant neuroligin-3) that can be inserted into the genome of the host cell, e.g., by homologous recombination. In the invention the wild-type neuroligin gene is recombined with a mutated neuroligin gene. For example, based upon the sequences provided herein a targeting vector can be designed such that homologous recombination occurs whereby the wild-type gene is recombined with a mutated neuroligin encoding a neuroligin-3 polypeptide comprising an Arg471Cys mutation (see, SEQ ID NO:3 and 4) in the rat. The targeting vector generally has a 5' flanking region and a 3' flanking region homologous to segments of the gene of interest, surrounding a foreign DNA sequence to be inserted into the gene (e.g., the mutated sequence). The 5' flanking region and the 3' flanking region are homologous to regions within the gene surrounding the portion of the gene to be replaced with the mutated region of the polynucleotide. DNA comprising the targeting vector and the native gene of interest are contacted under conditions that favor homologous recombination. For example, the targeting vector and native gene sequence of interest can be used to transform embryonic stem (ES) cells, in which they can subsequently undergo homologous recombination. Proper homologous recombination can be confirmed by Southern blot analysis of restriction endonuclease digested DNA.

In an animal obtained by the methods above, the extent of the contribution of the ES cells that contain the disrupted gene to the somatic tissues of the transgenic animal can be determined visually by choosing animal strains for the source of the ES cells and blastocyst that have different coat colors. Alternatively, behavioral difference can be identified.

Generally, the embryonic stem cells (ES cells) used to produce a transgenic animal will be of the same species as the transgenic animal to be generated. Thus for example, mouse embryonic stem cells will be used for generation of transgenic mice, rat ES cells for transgenic rats and the like.

Embryonic stem cells are generated and maintained using methods well known to the skilled artisan such as those described by Doetschman et al. (1985) J. Embryol. Exp. Mol. Biol. 87:27-45). Any line of ES cells can be used; however, the line chosen is typically selected for the ability of the cells to integrate into and become part of the germ line of a developing embryo so as to create germ line transmission of the transgenic construct. Thus, any ES cell line that is believed to have this capability is suitable for use herein. One mouse strain that is typically used for production of ES cells is the 129J strain. Another ES cell line is murine cell line D3 (American Type Culture Collection, catalog no. CKL 1934). Still another ES cell line is the WW6 cell line (Ioffe et al. (1995) PNAS 92:7357-7361). The cells are cultured and prepared for construct insertion using methods well known to the skilled artisan, such as those set forth by Robertson in: Teratocarcinomas and Embryonic Stem Cells: A Practical Approach, E. J. Robertson, ed. IRL Press, Washington, D.C. 1987); by Bradley et al. (1986) Current Topics in Devel. Biol. 20:357-371); and by Hogan et al. (Manipulating the Mouse Embryo: A Laboratory Manual, Cold Spring Harbor Laboratory Press, Cold Spring Harbor, N.Y. (1986)).

A stem cell in which such a homologous recombination event has taken place can be selected for by virtue of the stable integration into the genome of the nucleic acid of the gene encoding a positive selectable marker and subsequent selection for cells expressing this marker gene in the presence of an appropriate drug (e.g., neomycin).

Each targeting vector to be inserted into the cell is linearized. Linearization is accomplished by digesting the DNA with a suitable restriction endonuclease selected to cut only within the vector sequence and not the 5' or 3' homologous regions or the selectable marker region.

For insertion, the targeting vector is added to the ES cells under appropriate conditions for the insertion method chosen, as is known to the skilled artisan. For example, if the ES cells are to be electroporated, the ES cells and targeting vector are exposed to an electric pulse using an electroporation machine and following the manufacturer's guidelines for use. After electroporation, the ES cells are typically allowed to recover under suitable incubation conditions. The cells are then screened for the presence of the targeting vector as explained herein. Where more than one construct is to be introduced into the ES cell, each targeting vector can be introduced simultaneously or one at a time.

After suitable ES cells containing the transgenic construct in the proper location have been identified by the selection techniques outlined herein, the cells can be inserted into an embryo. Insertion may be accomplished in a variety of ways known in the art, however the typical method is by microinjection. For microinjection, about 10-30 cells are collected into a micropipet and injected into embryos that are at the proper stage of development to permit integration of the foreign ES cell containing the recombination construct into the developing embryo. For instance, the transformed ES cells can be microinjected into blastocytes. The suitable stage of development for the embryo used for insertion of ES cells is very species dependent, however for mice it is about 3.5 days. The embryos are obtained by perfusing the uterus of pregnant females. Suitable methods for accomplishing this are known to the skilled artisan.

While any embryo of the right stage of development is suitable for use, typical embryos are male. In mice, the typical embryos also have genes coding for a coat color that is different from the coat color encoded by the ES cell genes. In this way, the offspring can be screened easily for the presence of the transgenic construct by looking for mosaic coat color (indicating that the ES cell was incorporated into the developing embryo). Thus, for example, if the ES cell line carries the genes for white fur, the embryo selected will carry genes for black or brown fur.

After the ES cell has been introduced into the embryo, the embryo may be implanted into the uterus of a pseudopregnant foster mother for gestation. While any foster mother may be used, the foster mother is typically selected for her ability to breed and reproduce well, and for her ability to care for the young. Such foster mothers are typically prepared by mating with vasectomized males of the same species. The stage of the pseudopregnant foster mother is important for successful implantation, and it is species dependent. For mice, this stage is about 2-3 days pseudopregnant.

Offspring that are born to the foster mother may be screened initially for mosaic coat color where the coat color selection strategy (as described herein) has been employed. In addition, or as an alternative, DNA from tail tissue of the offspring may be screened for the presence of the transgenic construct using Southern blots and/or PCR techniques. Offspring that appear to be mosaics may then be crossed to each other, if they are believed to carry the transgenic construct in their germ line, in order to generate homozygous transgenic animals. Homozygotes may be identified by Southern blotting of equivalent amounts of genomic DNA from mice that are the product of this cross, as well as mice that are known heterozygotes and wild type mice.

Progeny of the transgenic animals may be obtained by mating the transgenic animal with a suitable partner, or by in vitro fertilization of eggs and/or sperm obtained from the transgenic animal. Where mating with a partner is to be performed, the partner may or may not be transgenic and/or a knockout; where it is transgenic, it may contain the same or a different knockout, or both. Alternatively, the partner may be a parental line. Where in vitro fertilization is used, the fertilized embryo may be implanted into a surrogate host or incubated in vitro, or both. Using either method, the progeny may be evaluated using methods described above, or other appropriate methods.

Retroviral infection can also be used to introduce a targeting vector into an animal. The developing embryo can be cultured in vitro to the blastocyst stage. During this time, the blastomeres can be targets for retroviral infection (Jaenich, R. (1976) PNAS 73:1260-1264). Efficient infection of the blastomeres is obtained by enzymatic treatment to remove the zona pellucida (Manipulating the Mouse Embryo, Hogan eds. (Cold Spring Harbor Laboratory Press, Cold Spring Harbor, 1986). The viral vector system used to introduce the targeting vector is typically a replication-defective retrovirus carrying the exogenous nucleic acid (Jahner et al. (1985) PNAS 82:6927-6931; Van der Putten et al. (1985) PNAS 82:6148-6152). Transfection is easily and efficiently obtained by culturing the blastomeres on a monolayer of virus-producing cells (Stewart et al. (1987) EMBO J. 6:383-388). Alternatively, infection can be performed at a later stage. Virus or virus-producing cells can be injected into the blastocoele (Jahner et al. (1982) Nature 298:623-628). Most of the founders will be mosaic for the targeting vector (e.g., the exogenous nucleic acids) since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo.

The transgenic non-human animals of the invention provide useful models for studying the expression and post-translational processing of mutant neuroligin-3. Such transgenic animals of the invention also provide models for screening agents useful in modifying intracellular retention and proper processing of neuroligin-3. The transgenic animals of the invention also provide sources of cells useful in in vitro studies and screening techniques.

The development of a subject predisposed or at risk of having autism or an autism-like disorder provides an opportunity for presymptomatic therapeutic intervention, especially if newborn screening programs can identify affected subjects. It is contemplated that subjects and fetuses can be treated for such autism spectrum disorders resulting from mutant neuroligin proteins that are retained intracellularly by contacting the subject or fetus using gene replacement or modification therapies alone or in combination with other therapies described herein.

Where appropriate, the gene therapy vectors can be formulated into preparations in solid, semisolid, liquid or gaseous forms in the ways known in the art for their respective route of administration. Means known in the art can be utilized to prevent release and absorption of the composition until it reaches the target organ or to ensure timed-release of the composition. In pharmaceutical dosage forms, the compositions can be used alone or in combination with other pharmaceutically active compounds. A sufficient amount of vector containing the therapeutics polynucleotide is administered to provide a pharmacologically effective dose of the gene product. In one aspect, the invention contemplates gene therapy whereby a subject comprising a mutant neuroligin is contact with a wild-type neuroligin such that the wild-type neuroligin is expressed in the subject.

One skilled in the art recognizes that different methods of delivery may be utilized to administer a vector into a cell. Examples include: (1) methods utilizing physical means, such as electroporation (electricity), a gene gun (physical force) or applying large volumes of a liquid (pressure); and (2) methods wherein said vector is complexed to another entity, such as a liposome or transporter molecule or retroviral vector.

Accordingly, the invention provides a method of transferring a therapeutic gene to a host, which comprises administering a vector of the invention having a wild-type neuroligin, typically as part of a composition, using any of the aforementioned routes of administration or alternative routes known to those skilled in the art and appropriate for a particular application. Effective gene transfer of a vector to a host cell in accordance with the invention can be monitored in terms of a therapeutic effect (e.g. alleviation of some symptom associated with autism spectrum disorders) or, further, by evidence of the transferred gene or expression of the gene within the host (e.g., using the polymerase chain reaction in conjunction with sequencing, Northern or Southern hybridizations, or transcription assays to detect the nucleic acid in host cells, or using immunoblot analysis, antibody-mediated detection, mRNA or protein half-life studies, or particularized assays to detect protein or polypeptide encoded by the transferred nucleic acid, or impacted in level or function due to such transfer).

The amount of vector to be added per cell will likely vary with the length and stability of the therapeutic gene inserted in the vector, as well as also the nature of the sequence, and is particularly a parameter which needs to be determined empirically.

It is possible that cells containing the therapeutic gene may also contain a silicide gene (i.e., a gene which encodes a product that can be used to destroy the cell, such as herpes simplex virus thymidine kinase). In many gene therapy situations, it is desirable to be able to express a gene for therapeutic purposes in a host cell but also to have the capacity to destroy the host cell once the therapy is completed, becomes uncontrollable, or does not lead to a predictable or desirable result. Thus, expression of the therapeutic gene in a host cell can be driven by a promoter, although the product of said silicide gene remains harmless in the absence of a prodrug. Once the therapy is complete or no longer desired or needed, administration of a prodrug causes the silicide gene product to become lethal to the cell. Examples of silicide gene/prodrug combinations which may be used are Herpes Simplex Virus-thymidine kinase (HSV-tk) and ganciclovir, acyclovir or FIAU; oxidoreductase and cycloheximide; cytosine deaminase and 5-fluorocytosine; thymidine kinase thymidilate kinase (Tdk::Tmk) and AZT; and deoxycytidine kinase and cytosine arabinoside.

The effect of therapeutics, or agents being screened for therapeutic potential, can be identified by measuring changes in behavioral symptoms of animal models and subjects afflicted with autistic syndromes. For example, the hallmarks of autistic disorders include severely impaired social interactions, bizarre and narrow range of interests, severe speech and language disorder. Asperger syndrome and autism are quite similar in behavioral symptoms. In Asperger syndrome, the severe language delay or regression in behavior is not present in the early preschool years. In recent years, atypical sensory systems with both hypo and hypersensitivity to a variety of sensory stimulation has been added to the classic diagnostic symptoms of these disorders. The diagnosis of autism is confirmed by the presence or absence of behavioral symptoms using the DSM-IV manual. Since this is a clinical diagnosis the initial evaluation is of importance and should include an in-depth history from the primary caregivers, observation of the child, medical and neurological examination and standardized developmental testing. Additionally, most pediatric specialists will perform a variety of routine blood tests to identify possible medical causes for the child's developmental delay. Subject with autism may spend hours performing repetitive activities or watching the same video over and over. This hyper attention to repetitive stimulation is often obsessive in nature. Conversely, these very same subjects are remarkably inattentive, distractible and disorganized in interactive play and verbal tasks. This profile of inattention, distractibility and hyperactivity has resulted in the speculation that autism could be an extreme form of Attention Deficit Hyperactive Disorder (ADHD). The use of stimulants has been effective for many children with autism and extreme hyperactivity. It should be noted that the methods and compositions of the invention can be used in combination with such therapies (e.g., in combination with stimulants).

The invention has been generally described above, the following examples are provided to further illustrate the invention. The specific examples below are not intended to limit the invention.

EXAMPLES

Example 1

In one aspect, the disclosure shows that truncations just beyond the cholinesterase homology domain yield a soluble NL1 whose binding to neurexin can be quantitated by surface plasmon resonance. This approach has delineated the recognition domain for NL1 and establish a role for glycosylation processing in governing the interaction with NX1β.

By inserting a stop codon in the NL1 cDNA at various positions 5' of the region encoding the transmembrane span, the disclosure demonstrates the expression and characterization of soluble neuroligins with sequences replicating the extracellular domain of NL1. In stably transfected HEK293 cells, the protein is exported into the medium and can be purified in milligram quantities using the FLAG epitope attached at the amino-terminus of the processed protein. The soluble protein is glycosylated at the predicted N-linked glycosylation signals and presumably at several of the candidate O-linked glycosylation sites. Hydrodynamic analyses indicate that the protein behaves as a dimer in solution.

The principal advantage of the soluble protein is that studies to measure NL1 binding with its cognate partner, NX1β, can be conducted in solution, in real time and using physiologic buffers. Surface plasmon resonance can be employed to characterize the association of NL1 with NX1β and to rank order the affinities and binding capacities of the various members of the complex NL1 and NX1β gene families.

To examine the molecular determinants of the neuroligin-neurexin interaction, several truncated forms of NL1 were constructed and expressed in HEK293 cells. The truncated proteins are secreted into the cell culture medium, and can be purified as soluble neuroligins in milligram quantities. This enabled the analysis of several molecular features of NL1 that govern selectivity in its interaction with neurexin. The data indicate that specific posttranslational modifications may provide an additional level of control in the NX1β-NL1 interaction.

Plasmids, mutagenesis—The extracellular domain of the rat-NX1β-1 protein between residues 48 and 300 (hereafter referred as NX1β) was fused to a C-terminal end of GST using a pGEX-6P-3 plasmid that permits site-specific cleavage and simultaneous NX1β purification and production in *E. coli* BL21 cells (Stratagene, SD, CA). cDNAs encoding rat-NL1 (SEQ ID NO:5) and NL3 (SEQ ID NO:3) were subcloned into FLAG tagged vector (Sigma, St. Louis, Mo.) for detection and purification (Comoletti et al., 2003). Briefly, both NL1 and NL3 encode the FLAG octapeptide at their N-termini, a linker peptide of 10 residues followed by the NL sequence beginning at Gln-46 and Ala-35 respectively. Soluble mutants were also constructed by introducing stop codons at Tyr-692 in NL1 (SEQ ID NO:6) and Tyr-640 in NL3 (SEQ ID NO:4), generating the proteins NL1-691 and NL3-639 respectively. Soluble mutants were also constructed by introducing stop codons at Tyr-692, Thr-652, Ile-639, His-634 and Leu-627 generating the proteins NL1-691, NL1-651, NL1-638, NL1-633 and NL1-626. To eliminate individual N-glycosylation consensus sequences Asn, Ser or Thr were mutated to Ala generating the following proteins: T111A-NL1-638, N303A-NL1-638, N343A-NL1-638 and S549A-NL1-638. An N-Flag-mouse-AChE expression plasmid, truncated at Pro-548 and lacking the most carboxyl-terminal cysteine and thus incapable of intersubunit cross-linking (mAChE-548), was also constructed. Mutation sequences were introduced using the Quickchange Mutagenesis Kit (Stratagene, San Diego, Calif.) and subsequently subcloned into vectors and verified by restriction digests and DNA sequencing. Large-scale plasmid purifications used DEAE columns (Qiagen Inc., Valencia, Calif.). Mouse AChE truncated at L539 was fused to the C-terminal part of NL1 starting at His634, resulting in the AChE-NL1 chimera.

Cell culture and transfections—HEK293 cells were maintained at 37° C. and 10% $CO_2$ in Dulbecco's modified Eagle's (DMEM) medium containing 10% fetal bovine serum and periodically tested to ensure the absence of mycoplasma. Cells were transfected by $(Ca)_3(PO_4)_2$ precipitation with 10 μg of plasmids carrying the neomycin acetyltransferase gene and were selected by growth in 800 μg/ml G418 (Geneticin, Sigma). After two to three weeks, surviving cells formed colonies suitable for clonal selection. The best producing clones were further expanded for large-scale production.

NL1-1 and NX1β expression and purification—To purify soluble neuroligins and NX1β, two to four liters of media were typically collected over a few days from triple layer flasks (120 mL/flask) maintained in Ultraculture serum free medium (Biowhittaker, Walkersville, Md.) at 37° C. and 5% $CO_2$. The medium containing expressed NL1 was passed over a column containing 6 mL of M2 anti-FLAG-affinity gel (Sigma) at approximately 1 mL/min. After washing, the protein was eluted in 2.5 bed volumes of Hepes buffer (10 mM Hepes, pH 7.4; 150 mM NaCl; 1 μg/ml Leupeptin) containing 100 μg/mL of FLAG peptide (Sigma) and the column rinsed immediately with 2.5 bed volumes of Hepes buffer. The eluate and rinse were concentrated using Centriprep 30 (Millipore, Bedford, Mass.) to a final volume of 0.5-1 mL, and stored at 4° C.

For purification of the soluble NX1β fusion protein a similar set was used; however, protein A Sepharose 4 Fast Flow (Amersham Pharmacia Biotech AB, Sweden) was employed to bind the human-IgG portion of NX1β. Elution was accomplished with 10 mM glycine buffer (pH 3.5). The eluate was immediately pH-equilibrated with 20 μl of 1M Tris HCl, pH 8, per mL of eluate.

To purify NL1 from cell extracts, 25 to 50 15 cm-dishes were grown to confluence. The cells were then harvested in cold phosphate buffered saline (PBS), centrifuged and resuspended in 5 mL of cold lysis buffer solution (10 mM Tris HCl, pH 8.0; 150 mM NaCl; 0.5% NP40; 0.01% bacitracin; 0.04% benzamidine; 0.02% sodium azide; 1 mM EGTA). The cell suspension was spun at 2,000 rpm for 10 min at 4° C. to remove insoluble material and then at 20,000×g for 30 min at 4° C. The supernatant containing all the soluble proteins was cycled three times over a column containing 3 mL of M2 anti-FLAG-affinity gel, washed and eluted with FLAG peptide as above.

Sedimentation equilibrium analysis—Analytical ultracentrifugation was conducted in a Beckman/Coulter XL-I centrifuge equipped with UV absorption optics using an 60 Ti rotor. Protein solutions of 30, 100 and 300 μg/mL of NL1 were used in a six-channel charcoal-filled epon centerpiece loaded with 110 μL of sample and 125 μL of reference Hepes buffer pH 7.4. Samples were spun at 20° C. for 16 hours at 8,000, 10,000 and 12,000 rpm. Equilibrium was attained as judged by the overlay of the last three scans. Data were recorded in step mode with a Δr of 0.001 cm, and 5 replicate absorption measurements were performed at each step every two hours. The partial specific volume, $\bar{v}$, of NL1 was calculated using Sednterp software (ver. 1.06) accounting for total sugars. Molar masses of the proteins were calculated using XL-A/XL-I Data Analysis Software version 4.0 based on Origin™ program.

Size exclusion chromatography—NL1-691, NL1-651 and NL1-638 were analyzed by size exclusion chromatography using a Superdex 200 HR 10/30 column attached to a Pharmacia FPLC system. Columns were run at room temperature with Hepes buffer pH 7.4 at 0.5 ml/min.

Mass spectrometry—NL1-691 wild-type, C286A-NL1-691, C286A/R473C-NL1-691, NL3-639, and R471C-NL3-639 were prepared for mass spectrometric analysis using the following conditions. NLs (50 μg) at 1 mg/mL protein in 50 mM $NH_4HCO_3$, buffer pH 7.8, were incubated with 50 mM iodoacetamide for 2 h at 37° C., prior to the addition of 6 M guanidine-HCl, pH 6.5 and incubation for 2 h at 37° C. The alkylating reagent and denaturant were removed by spin-filtering using Microcon-30 devices (Millipore, Bedford, Mass.) and exchanged to 50 mM $NH_4HCO_3$, buffer pH 7.8. Digestion of NLs with protease and removal of N-linked glycosylation was carried out with sequence grade modified trypsin (Promega, Madison, Wis.) at 1:50 (w/w) of trypsin: NL and 15 mU of PNGase F (Prozyme, San Leandro, Calif.) for 18 h at 37° C.

Matrix-assisted laser desorption/ionization time-of-flight mass spectrometry (MALDI-TOF MS) was performed on a PE Biosystems Voyager DE-STR Biospectrometry workstation (Framingham, Mass.). Trypsinized and de-N-glycosylated NLs were mixed with 5 mg/ml alpha-cyano-4-hydroxy-cinnamic acid (CHCA) matrix in 50% (v/v) acetonitrile, 0.3% (v/v) TFA, pH 2.2. One-μl aliquots of peptide-matrix mixture were spotted on a target plate and dried by slow evaporation. Mass spectra were acquired using delayed extraction conditions in positive-ion reflector and linear modes with an acceleration voltage of 20 kV for 800 to 3500 Da mass-to-charge (m/z) and in positive-ion linear mode. External calibration was performed using angiotensin I and ACTH peptides (1-17 and 18-39) for reflector mode, and ACTH peptide (7-38) and bovine insulin for calibration in linear mode. Mass spectra were averaged from 256 laser scans, and data were processed with PE Biosystems Grams 3.0 software program.

Surface plasmon resonance analysis of the NL1-NX1β complex—NL1 binding was analyzed at 25° C. using Hepes buffer, pH 7.4, containing 2 mM of $CaCl_2$ and 0.005% (v/v) surfactant P20, on a BIAcore 3000. NX1β was covalently bound to the carboxymethylated dextran matrix of a CM5 chip (BIAcore, Uppsala, Sweden) (Jonsson et al., 1991) at approximately 3000 resonance units (RU). Reference data were subtracted from the sample flow channel that did not contain β-neurexin, to obtain specific NX10 binding. NL1 was usually injected over the NX1β surfaces as a set of 6 concentrations differing by three-fold at a flow rate of 50 μL/min to minimize sample diffusion and mass transport limitations.

Primary Neuronal Culture, Co-Culture Experiments and Immunocytochemistry—Primary hippocampal neuronal cultures were prepared from E18 rats. Dissociated neurons were plated onto poly-L-lysine-treated glass coverslips at a density of 150-500 cells/mm² over a monolayer of glia. Cells were maintained in Neurobasal medium (Invitrogen, Carlsbad, Calif.). COS cells were cultured in DMEM supplemented with 10% (v/v) fetal bovine serum in a humidified atmosphere of 5% $CO_2$ at 37° C. Cells were transfected with 1 μg/well of cDNA (in a 6-well plate or in a 35-mm dish) using Fugene6 (Roche Applied Science, Indianapolis, Ind.). Transfected COS cells were added to the neurons at DIV 10-14. Two to five days after addition of the COS cells the cultures were fixed in cold 100% methanol or 4% paraformaldehyde/PBS, permeabilized with 0.2% Triton X-100/PBS or 0.1% Saponin/PBS, and incubated with primary and secondary antibodies in PBS with 1% goat serum, 2% bovine serum albumin (BSA). The following antibodies were used for immunocytochemistry of the co-cultures: anti-neuroligin mouse monoclonal 4C12 and rabbit polyclonal L067; anti-synapsin mouse monoclonal C110.22, and rabbit polyclonal E028.

Image Acquisition and Analysis—Immunofluorescence Image Acquisition and Analysis—Parental HEK293 and NL1 and NL3-stably expressing cells were plated on poly-d-lysine coated glass coverslips and grown overnight in Dulbecco's modified Eagle's Medium. Cells were fixed in 4% paraformaldehyde-PBS for 20 minutes, washed and labeled for immunofluorescence. Briefly, cells were permeabilized with 0.5% saponin, 1% BSA, 10 mM EDTA in PBS for 5 minutes and incubated in blocking buffer (PBS, 2% normal donkey serum, 0.5% BSA, 50 mM glycine) in presence of 0.1% saponin for 30 minutes. Cells were then incubated for 1 hour in anti-flag M2 monoclonal antibody (Sigma, St. Louis, Mo.) diluted 1:500 in a 1:5 dilution of the blocking buffer. After washing in PBS and then the above buffer, cells were incubated for 1 hour in donkey anti mouse, Cy5-conjugated antibody (Jackson Immuno Research, West Grove, Pa.) diluted 1:100 in buffer. Cells were then washed in PBS containing RNase (Sigma) to remove excess secondary antibody and to degrade RNA. Cells were incubated with 5 μg/ml propidium iodide (Sigma) to label nuclei. After washing, cells were mounted in Gelvatol and imaged using an MRC-1024 laser-scanning confocal system (BioRad, Cambridge, Mass.) coupled to a Zeiss Axiovert 35 M microscope.

Analytical procedures—Western blots were performed using standard procedures. Protein concentrations were estimated by Bradford assay. To achieve deglycosylation 10-15 μg of NL1 in 200 μL was incubated: a) with PNGase F (Glyko, Novato, Calif.), using 0.5 mU/μg of protein, at 37° C.

for 16 h at pH 7.4; b) with 10 mU of Sialidase II (Glyko) and incubated at 37° C. for 16 h at pH 6.5; or c) with both glycosidases under the same conditions, but at pH 6.5. Samples were then stored on ice and a 2 μL aliquot taken for immunoblotting. Antibody anti neuroligin-1/3 were purchased from Synaptic System (Goettingen Germany).

Expression and characterization of soluble NL1—To express soluble recombinant forms of NL1, stop codons were introduced into the full-length NL1 cDNA at various positions N-terminal to the transmembrane spanning region (FIG. 1). The longest truncated neuroligin, NL1-691, contains a cleavable leader sequence that allows for export and processing of the proteins, an N-terminal FLAG epitope, the complete ChE-like domain and the entire Ser-Thr rich stalk region. All of the potential N- and O-linked glycosylation sites are retained. NL1-651 is devoid of 40 carboxyl-terminal residues that contain the Asn662 glycosylation site and about half of the predicted O-glycosylation sites; NL1-638 lacks all the potential O-linked glycosylation sites. NL1-633 and NL1-626 further shorten the protein and terminate in the cholinesterase homologous domain. Residue homology comparisons indicate that NL1-638 is of comparable length to mouse AChE truncated at residue Pro548 that expresses as a fully functional, soluble AChE. Recombinant NX1β, expressed as a soluble human-IgG fusion protein, appears in reducing SDS-PAGE gels as a broad band with an apparent $M_r$ of 72 kDa.

Since rat and human NL3 sequences are virtually identical (99.8%) and rat NL3 shares 74.1% amino acid identity with rat NL1 in the extracellular domain, NL1 and NL3 rat proteins with mutations at Arg473 and Arg471 respectively were used to study the biochemical anomalies caused by the Arg451Cys mutation in humans. The human numbering does not include a 20 amino acid splice insertion found in rat. Rat NL1 and NL3 cDNAs were truncated to generate the proteins NL1-691 and NL3-639, lacking both the transmembrane and cytoplasmic domains. The 691 truncation occurs just before the transmembrane span, while that at 639 also removes an O-glycosylation domain that connects αβ-hydrolase-fold region to the membrane spanning sequence. This region was found to have minimal influence on both expression and β-neurexin binding (Comoletti et al., 2003). Truncated soluble proteins were necessary both for measuring β-neurexin binding activity and for mass spectrometry analysis.

Transfection of the truncated NL1 and NL3 cDNAs, followed by immunoblotting, reveals the protein in both the cell extract and culture medium, indicating that truncated neuroligins are correctly translated, processed and transported along the proper trafficking pathway for secretion. The proteins are fully glycosylated, correctly folded and functional In immunoblots after SDS-polyacrylamide gel electrophoresis (SDS-PAGE), the soluble forms show distinctive migrations depending on whether they were harvested from the cell extract or medium. FLAG full-length NL1, with a calculated peptide mass of 91,175 Da appeared in SDS-PAGE as a double band with $M_{rs}$ of ~140 kDa and 120 kDa (FIG. 2 left and table 1). The relative density of the bands expressed in HEK293 cells, with the higher molecular mass band being more intense, resembles that seen in rat brain indicating that NL1 is constitutively expressed as two predominant, differentially glycosylated forms. NL1-691 appears in SDS-PAGE at a $M_r$ of ~98 kDa when extracted from the cell lysate, while after being exported outside the cell, presumably after completion of post-translational processing, it appears as broad band at ~126 kDa (FIG. 2). Similar differences in apparent $M_r$ depending on origin of harvest are visible in both NL1-651 and NL1-638.

Relative expression levels for each mutant were estimated from the amount of purified protein recovered from serum-free media. The three longer mutants (NL1-691, NL1-651 and NL1-638) have comparable expression but appearance in the medium markedly decreased for NL1-633 and was not detectable for NL1-626 (Table 1). Since intracellular expression of the two shorter mutants revealed levels of antigenically reactive protein comparable with the intracellular expression of the exported mutants, it is possible that folding of these mutants was compromised.

Hydrodynamic properties and the oligomeric state of the NL1s were initially monitored by size exclusion chromatography. The retention times of the NL1-691, NL1-651 and NL1-638 were compared to globular, non-glycosylated protein standards giving an apparent mass between 260-280 kDa, indicative of dimensionally asymmetric proteins or oligomers. Samples were analyzed by sedimentation equilibrium (SE), where the counterbalancing influences of the diffusion and sedimentation should reflect the molecular masses. Using different concentrations of NL1-691 (30-100-300 μg/ml) and three different rotor speeds, molecular weight was determined to be 174,000±5,000 Da (n=9). Comparison with the determined mass spectrometry (MS) weight averaged mass (88,900±200 for the monomer, 178,000 Da for the dimer) indicated that truncated NL1 was a dimer at these concentrations. NL1-638 had a mass of 160,000±6,000 Da (n=6) from sedimentation equilibrium data (MS data: 79,900±200 Da monomeric form, 160,000 Da for the dimer) (FIG. 3A, B). The distribution of the residuals in the analysis appeared to be random, and the difference between the experimental and measured $M_r$ is well within the 10% typically seen for ultracentrifugation sample columns of 2 mm in length.

Figure 4:
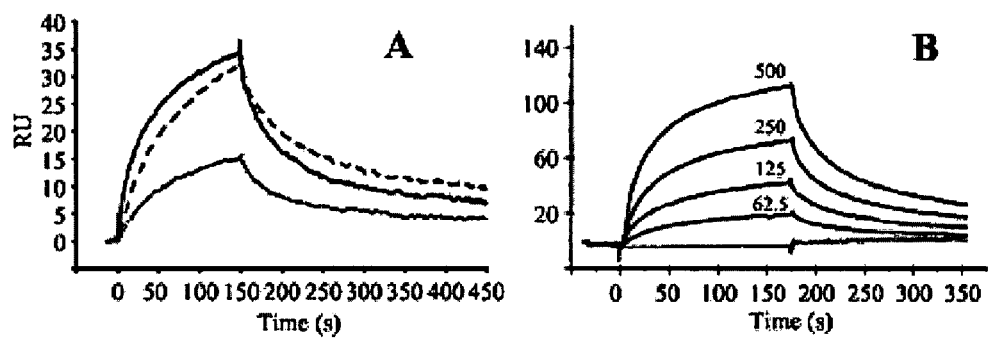
FIG. 4A-B shows the relative binding kinetics of three truncated NL1 mutants. A) Three neuroligins-1, truncated in the extracellular domain (solid line: NL1-638, dashed line: NL1-651, dotted line: NL1-691), were injected at 125 nM over the surface of neurexin-1-β (NX1β) attached to the BIAcore™ chip. Injections were in Hepes buffer at 20 mL/min. The injection interval was 150 seconds followed by a decay interval of 300 seconds in which running buffer alone runs through the surface. Table 1 (below) gives maximum binding of the three neuroligins. RU: resonance units. B) NX1β binding capacity of the four designated concentrations (nM) of NL1-638 (solid line) compared to identical concentrations of mAChE (dotted line).

Binding of soluble truncated NL1 is dependent on $Ca^{2+}$ and the amino-terminal NL1 sequence homologous to acetylcholinesterase—To compare the relative NX1β binding of the different NL1 mutants, a range of NL1 concentrations extending between 62.5 and 2000 nM was injected and binding monitored by SPR. NL1-651 and NL1-638 showed about 2.5-fold enhanced binding over NL1-691 indicating that the stalk region itself, when not associated to the cell membrane, reduces apparent binding of the soluble form (FIG. 4A). Rates of association and dissociation using recombinant, soluble entities provide an estimate of the kinetic parameters for the interaction. The calculated bimolecular association rate constant, $k_a=5\times10^4$ $M^{-1}$ $s^{-1}$; dissociation rate constant, $k_d=0.015$ $s^{-1}$, giving an equilibrium dissociation constant $K_D$ of ~300 nM. In SPR experiments binding of the full-length NL1 to NX1β in either the absence or presence of detergent (0.5% NP40) was not detected. The detergent requirement for solubility of the full-length NL1 precludes its direct comparison with the soluble forms.

Mouse AChE, when tested for NX1β binding over an extended concentration range (62.5 nM to 10 μM) using NX1β showed no binding for soluble monomeric form of mAChE in the subtracted sensorgram. A similar result was found for NX1β-3 that represents the unspliced isoform at position #4 (cf: FIG. 4B). Similarly no binding to the immobilized NX1β was observed for bovine serum albumin over the same concentration range.

Figure 5:
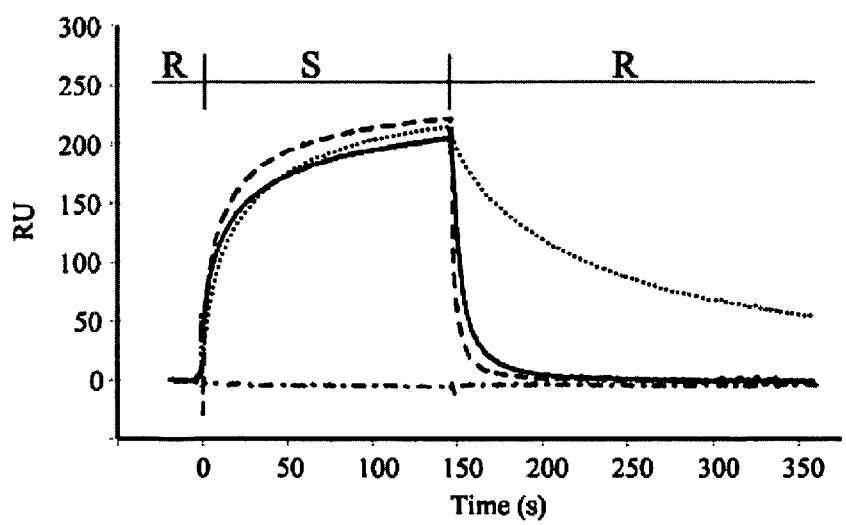
FIG. 5 shows cation dependence of NL1-NX1β associations. Dotted-dashed line, signal generated by 2 mM $Mg^{2+}$ both in running buffer and in NL1 sample (2 mM); solid line, 2 mM $Mg^{2+}$ in running buffer and 2 mM $Ca^{2+}$ in NL1 sample; dashed line, 5 mM EDTA in running buffer, 2 mM $Ca^{2+}$ in NL1 sample; dotted line, 2 mM $Ca^{2+}$ both in running buffer and in NL1 sample. R: running buffer alone flows through the flow channel; S: sample of NL1 is injected and replaces running buffer. RU: resonance units.

To examine the $Ca^{2+}$ dependence of NX1β-NL1 binding, NL1-691 purified in $Ca^{2+}$-free Hepes buffer was diluted in either Hepes-$Ca^{2+}$ or Hepes-$Mg^{2+}$ buffer and injected over the NX1β surface. Specific binding was detected only in presence of $Ca^{2+}$ (FIG. 5). Moreover, replacing $Ca^{2+}$-sample buffer with $Mg^{2+}$ at the end of the injection resulted in a rapid diminution of the signal to baseline. Addition of a divalent cation chelator (EDTA, 5 mM) to the Hepes buffer showed a loss of specific binding that was more rapid than when $Mg^{2+}$ simply replaced $Ca^{2+}$, indicating that removal of $Ca^{2+}$ does not require dissociation of the complex. Hence, the $Ca^{2+}$ is not apparently sequestered at the NX1β-NL1 interface.

Figure 6:
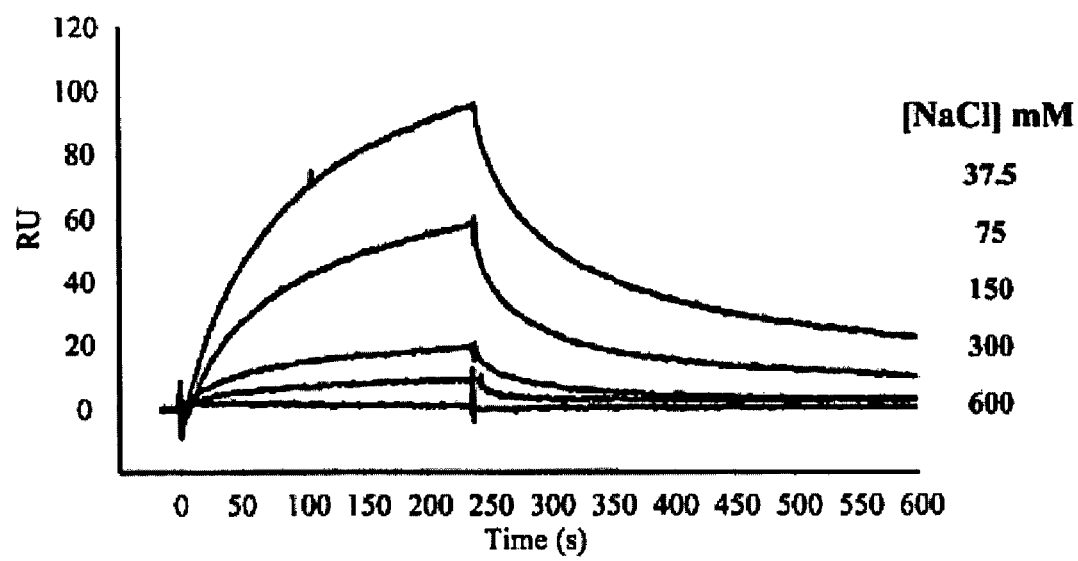
FIG. 6 shows the ionic strength dependence of NL1 binding. A non-saturating NL1-691 concentration (30 nM) was diluted in standard buffer with different ionic strengths adjusted by NaCl and injected on the same NX1β surface. Numbers on the right side indicated the NaCl concentration for each injection shown top to bottom. RU: resonance units.

To determine if the ionic strength of the buffer plays a role in the NX1β-NL1 association, NL1-691 was diluted in different buffers with NaCl concentrations ranging from 37.5 mM to 600 mM. As the sensorgram overlay in FIG. 6 shows, at NaCl concentration higher than 75 mM the binding becomes markedly reduced and is virtually lost above 300 mM, indicating that a significant component of the interaction is electrostatic.

Figure 7:
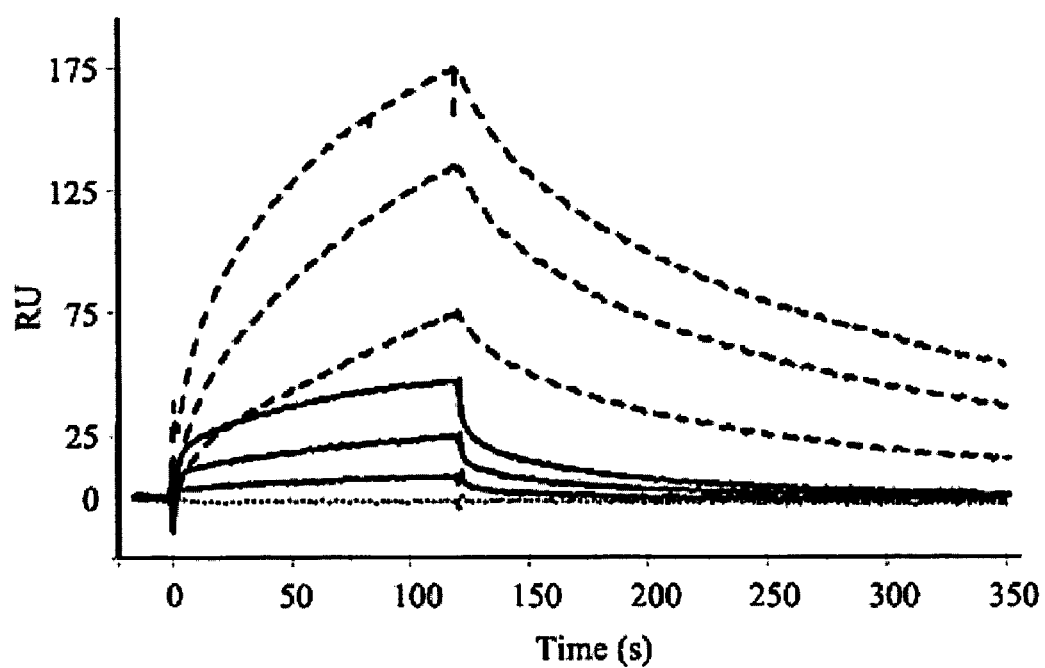
FIG. 7 shows NX-binding capacity of NL1-691 purified from medium and cell extract. Dashed lines, 65 nM, 32.5 nM and 16.25 nM of NL1 purified from cell extract; solid line, identical concentrations of NL1 purified from medium; dotted line, buffer only. RU: resonance units.

Removal of the NL1 N-glycosyl residues leads to an increased NX1β binding—SPR and immunoblotting techniques were used to ascertain if the glycosylation processing that gives rise to apparent migration differences in SDS-PAGE (FIG. 2) influences NX1β binding. Unprocessed NL1-691 purified from cell extract bound NX1β with a specific activity 4-6 fold higher than NL1-691 purified from the cell culture medium (FIG. 7) indicating that the post-translational modifications dramatically decreased both binding affinity as well as mobility on SDS-PAGE. The slower apparent association and dissociation rates measurable for the NL1-691 from the cell extract, compared to the NL1-691 from the medium, are due to the influence of ligand depletion (mass transport) that becomes important at high surface density in the face of lower ligand concentrations. High-density surfaces were necessary in order to detect the low signal generated by 16.25 nM of NL1-691 purified from medium.

Figure 8:
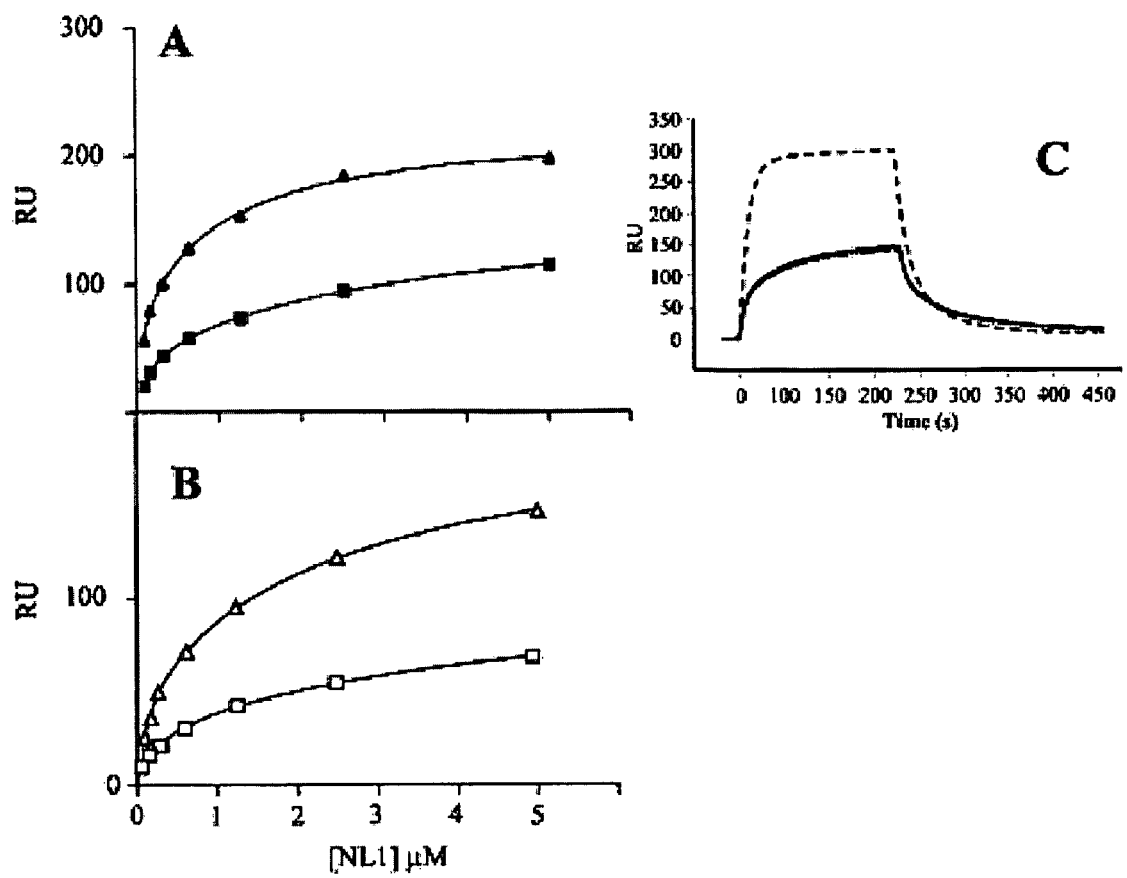
FIG. 8A-C shows the influence of N-linked glycosylation on NL1/NX1β interaction. Steady-state binding during flow is plotted as a function of NL1 concentration. A: NL1-638: Solid triangles, interaction kinetics for the PNGase F treated protein; solid squares, interaction kinetics for the native protein. B: NL1-691. Open triangles, interaction kinetics PNGase F treated protein; open squares, interaction kinetics for the native protein. NL1 concentrations ranged from 5000 nM to 78.21 nM in sequential two-fold dilutions. C: PNGase F control experiment using NL1-638: continuous line: neuroligin alone; dotted line: neuroligin and PNGase F (injected after immediate exposure); dashed line: neuroligin and PNGase F, injected after overnight incubation at 37° C. RU: resonance units.
Figure 9:
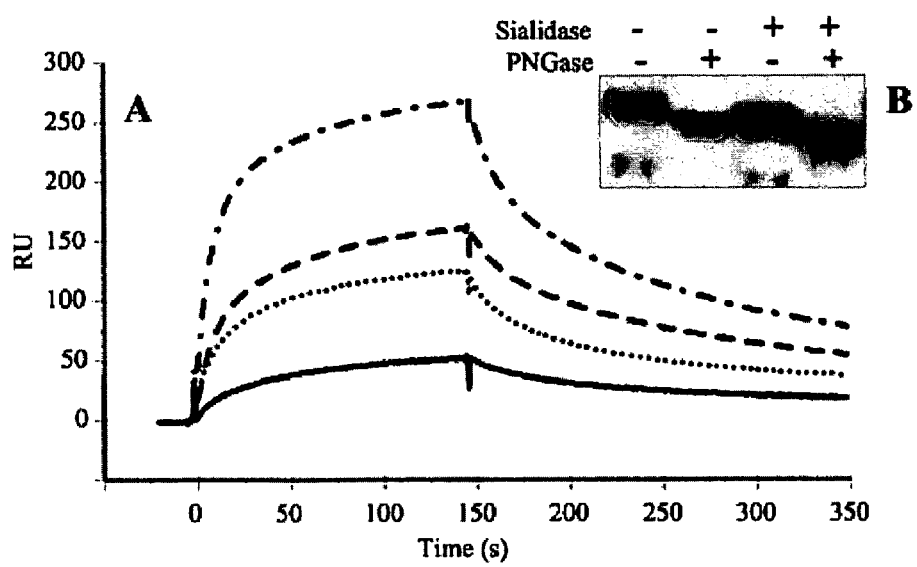
FIG. 9A-B shows the binding of NL1-638 prior to and following glycanase and sialidase treatment under non-denaturing conditions. A—Sialidase and PNGase were employed individually and in combination. Solid line, native protein; dotted line, PNGase treatment; dashed line, sialidase treatment; dotted-dashed line, PNGase F and sialidase treatment. A 500 nM solution of NL1-638 was employed in each injection. RU: resonance units. B—Immunoblot of the digested samples used in SPR study shows the extent of deglycosylation.

NL1-691 and NL1-638 were subjected overnight to enzymatic deglycosylation with PNGase F under non-denaturing conditions and analyzed by SPR (FIG. 8A, B). Each mutant showed approximately a three-fold increase in binding after PNGase F treatment that correlates with the increased mobility in SDS-PAGE. PNGase F alone did not bind NX1β and does not influence binding when mixed with NL1-638 immediately before injection over a NX1β surface (FIG. 8C). Proportional increases in binding following treatment of the two mutants indicated that the N-linked glycosylation site at position N662, which is not present in NL1-638, is not involved in the decreased binding of NL1-691. No binding was detected for PNGase F treated mAChE-548 (up to 10 μM). To determine whether sialic acid, that often terminally caps both N- and O-linked oligosaccharides, reduces binding affinity for NX1β, NL1-691 and NL1-638 were treated under non-denaturing conditions with sialidase II either alone or in combination with PNGase F. For both mutants, sialidase-II treatment alone increased binding about 2-2.5 fold. The combined treatment improved binding about 5 fold (FIG. 9). Since sialidase enhanced activity comparably in both mutants, it could not be ruled out that sialidation of the O-linked sugar set carried by the stalk region of NL1-691 mutant as source of binding hindrance.

To ascertain whether the single N-linked glycosylation site in NX1β influences the NX1β-NL1 interactions, NX1β treated with PNGase F was tested on NL1-691 and NL1-638. Enhanced migration in SDS-PAGE revealed that deglycosylation occurred; however, NL1 binding of deglycosylated NX1β was identical to untreated protein.

Figure 10:
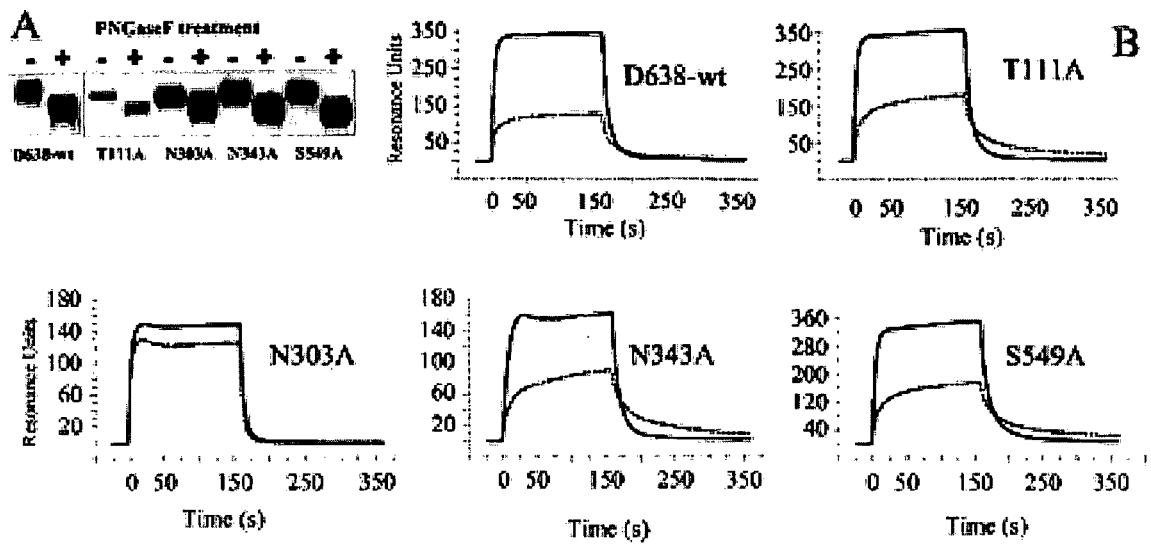
FIG. 10A-B depict the influence of deglycosylation of wild type and mutant NL1 on NX1β binding. A—Immunoblot of the wild type NL1-638 and the four N-linked glycosylation mutants shows the extent of PNGase F action. The respective samples were treated with PNGase F in non-denaturing buffer for 16 hrs and binding measured by surface plasmon resonance. B—Each graph shows the binding before and after deglycosylation of a single mutant over the same NX1β surface. The scale of each graph was chosen to optimally show the effect of the enzymatic treatment. Dotted line.

N-linked glycosylation of residue 303 found in the second splice site of NL1 reduces NX1β binding—To identify which of the N-linked glycosylation positions was responsible for hindering the NX1β binding, it was first determined that all four potential N-linked glycosylation sites of NL1-638 are fully occupied by oligosaccharides. The four N-glycosylation consensus sequences of NL1-638 were then mutated separately. Each mutant was divided in two identical aliquots, one of which was treated with PNGase F. NL1-638 wild type and three N-linked glycosylation mutants (T111A-NL1-638, N343A-NL1-638, S549A-NL1-638) digested with PNGase F increased their SDS-PAGE migration rates and their NX1B binding activity by 229±55% whereas N303A-NL1-638, enclosed in the second region of alternative splicing, revealed SDS-PAGE migration consistent with deglycosylation but exhibited no significant increase its NX1β binding (17±20%) (FIG. 10). The virtual lack of increase in activity after PNGase F treatment indicated that the mutation at position Asn303 was sufficient to remove a large fraction of the inhibitory behavior of soluble NL1 on the association with NX1β. This suggests that the 303 position may play a primary steric role in inhibiting NX1β-NL1 interaction.

The rate constant for NL1 dissociation, being a unimolecular reaction, should be independent of the concentration of the reacting species. The cross over of dissociation traces (FIG. 10) shows that deglycosylation of all the mutant forms of NL1 except N303A results in an increase in dissociation rate. Since total binding in the mutants is enhanced, the association rate constants must also increase, but to a greater extent. The N303A mutant has greater intrinsic rates of both association and dissociation, and it is marginally affected by PNGase F treatment The comparison of glycosylation mutations before and after PNGase F digestion using NL1-691 yielded a similar pattern of binding and enhancement with PNGase F, confirming position 303 as the main region for steric hindrance.

Figure 11:
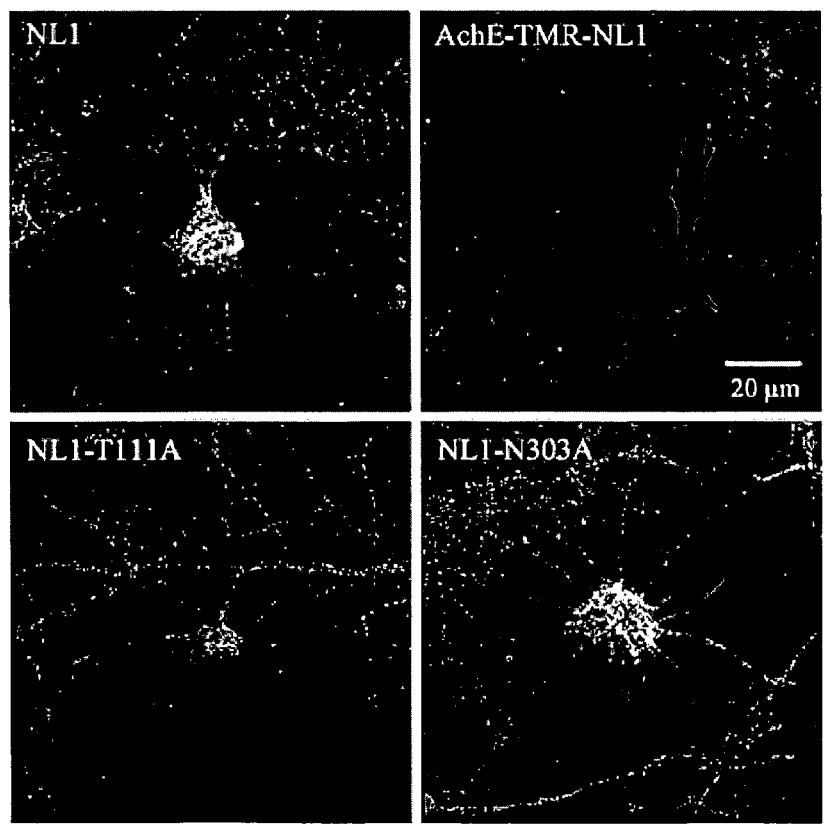

Further investigation focused on whether N303A-NL1 could stimulate presynaptic differentiation in hippocampal primary neurons co-cultured with NL1-transfected COS cells by determining co-localization of NL1 and synapsin expressed by the neurons at the contact points. Synapsin co-localized with cells expressing wild type NL1 as well as T111A-NL1 and N303A-NL1, while no co-localization was seen in co-cultures of AChE-NL1 chimera, indicating that NL1 mutants were able to initiate presynaptic maturation in these cultures (FIG. 11).

Expression and characterization of truncated neuroligins. Since rat and human NL3 sequences are virtually identical (99.8%) and rat NL3 shares 74.1% amino acid identity with rat NL1 in the extracellular domain, the NL1 and NL3 rat proteins were used with mutations at Arg473 and Arg471 respectively, to study the biochemical anomalies caused by the Arg451Cys mutation in humans. The human numbering does not include a 20 amino acid splice insertion found in rat. Rat NL1 and NL3 cDNAs were truncated to generate the proteins NL1-691 and NL3-639, lacking both the transmembrane and cytoplasmic domains. The 691 truncation occurs just before the transmembrane span, while that at 639 also removes an O-glycosylation domain that connects □⁀□-hydrolase-fold region to the membrane spanning sequence. This region was found to have minimal influence on both expression and β-neurexin binding. Truncated soluble proteins were necessary both for measuring β-neurexin binding activity and for mass spectrometry analysis.

Transfection of the truncated NL1 and NL3 cDNAs, followed by immunoblotting, reveals the protein in both the cell extract and culture medium, indicating that truncated neuroligins are correctly translated, processed and transported along the proper trafficking pathway for secretion. The proteins are fully glycosylated, correctly folded and functional.

Figure 12:
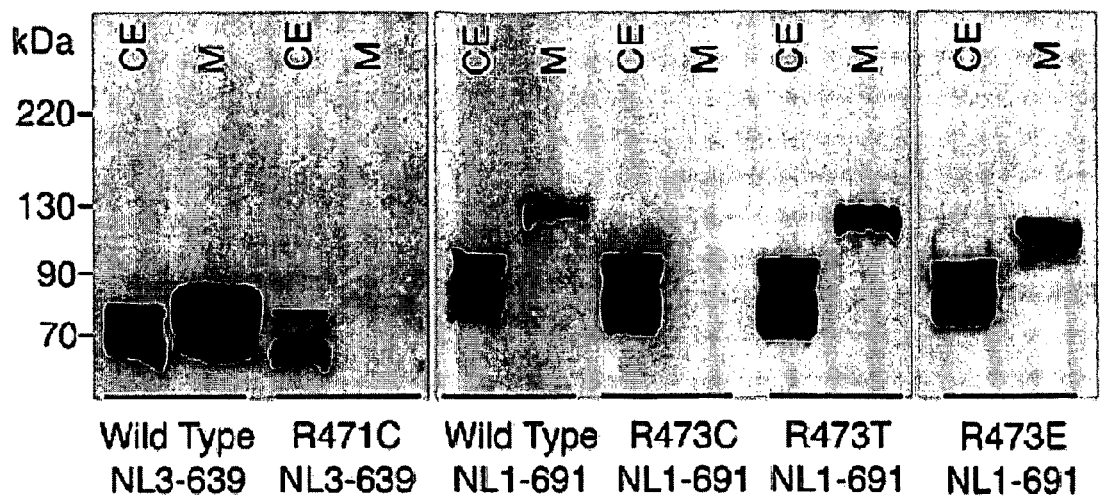

Expression and characterization of the mutated soluble neuroligins. Mutation of the conserved Arg451 to Cys virtually eliminated secretion of soluble NL1 and NL3 into the medium (FIG. 12), indicating that trafficking or folding of the mutated protein might be defective. To ascertain whether the alteration was general substitution for Arg or its specific replacement with Cys, two other mutants were made: R473T-NL1-691, to replace Cys with a residue of similar size and polarity, but unable to form disulfide bridges, and R473E-NL1-691 to reverse the charge of Arg451. Both mutants were secreted into the culture medium, demonstrating that only the Cys473 substitution disrupted neuroligin targeting to the cell surface (FIG. 12).

Figure 13:
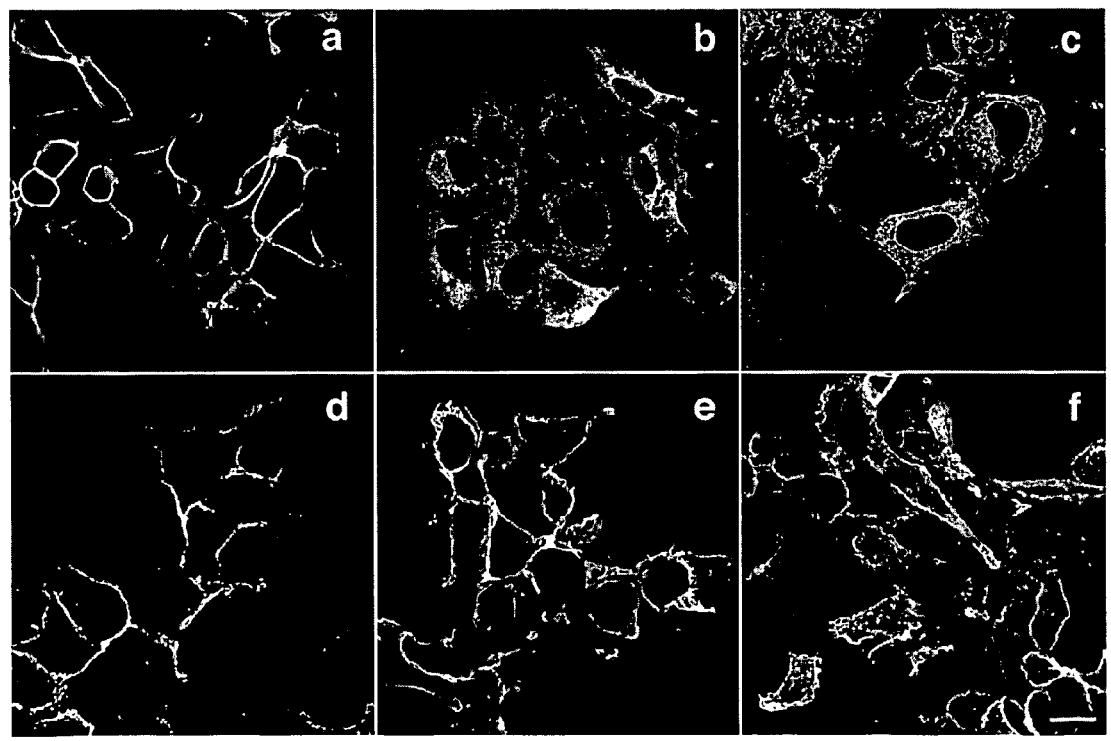

Immunofluorescence analysis of full-length neuroligins. Neuroligins, as synaptic proteins with a single transmembrane span, are targeted to the cell membrane. To insure that truncation of the protein in combination with the Arg mutation did not influence its trafficking, full-length neuroligins were expressed for an immunofluorescence cell based assay. Based on protein expression profiles, it is hypothesized that the newly introduced cysteine could form spurious disulfide bonds with other cysteines, preferentially with the single unpaired Cys286 found naturally in all four members of the NL family. To test this possibility, Cys286 was substituted with an Ala in wild type and the R473C-NL1-691 mutant protein, generating C286A/R473C-NL1-691 (CA/RC-NL1-691). Stably transfected cells permeabilized with saponin and probed with anti-FLAG antibody showed that wild type NL3 and NL1, as well as R473T-NL1, translocated normally to the cell surface, presenting indistinguishable patterns of expression. Consistent with immunoblotting data, both R473C-NL1 and R471C-NL3 were retained in the cytoplasm. On some cells, R471C-NL3 was visible on the cell membrane, displaying a fewer restrictions in retention than in mutated NL1. The residual secretion to the cell surface is possibly due to an intrinsically higher level of expression of the recombinant NL3. The double mutant CA/RC-NL1 did not show significant improvement in cell surface translocation when compared with the both R473C-NL1 or R471C-NL3 proteins (FIG. 13), indicating that abnormal disulfide bonding between the substituted Cys at 471 or 473 and Cys286 is not involved in the defective processing.

Figure 14:
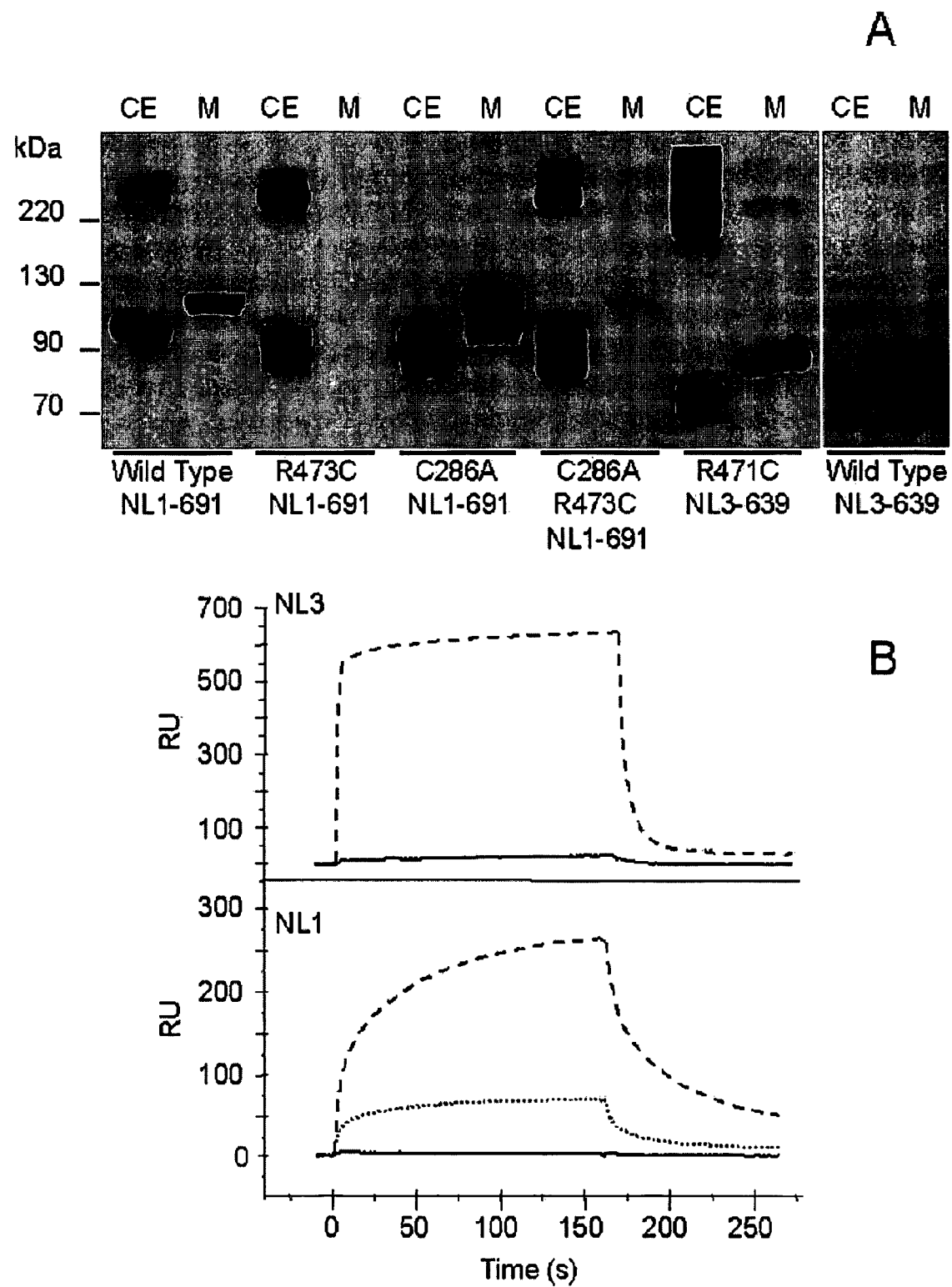

Electrophoresis under non-reducing conditions. To ascertain if the mutated Cys is implicated in intermolecular Cys bonding either with neuroligin itself or with heterologous ER resident proteins, the cell lysate and culture medium were subjected to SDS-PAGE in absence of β-mercaptoethanol followed by immunoblotting. In non-reducing conditions, expression of the exported proteins appears to be inversely related to the abundance of intracellular protein aggregates (FIG. 14A). Consistent with the expression pattern found in immunofluorescence, both R473C-NL1-691 and R471C-NL3-639 were largely retained intracellularly. On the contrary, C286A-NL1-691 showed no association with other proteins, but optimal extracellular expression. CA/RC-NL1-691 was almost completely retained intracellularly, indicating that the abnormal phenotype of the NL1 was not reversed by eliminating the potential for formation of an additional cysteine loop. Consistent with immunofluorescence data, this result suggests that solvent exposure of the cysteine is critical for retention within the cell.

The components of the aggregate of NL1 are unknown, but their prevalence in non-reducing conditions indicates that intermolecular disulfide bonding is involved (FIG. 14A). Whether the protein was incorrectly folded or subjected to thiol-mediated retention in the endoplasmic reticulum is thus far unresolved.

Mass spectrometric analysis of the soluble NL1 and NL3 proteins. The determination of the disulfide bonding pattern of NL1-691 using mass spectrometry is described herein. Respectable expression levels of NL3 enabled us to purify by affinity chromatography, both NL3-639 and R471C-NL3-639 from culture medium of stably transfected cells. A small amount of C286A/R473C-NL1-691 was also purified from culture medium, while this was not possible with R473C-NL1-691. Tryptic digests of purified de-N-glycosylated NL1-691, C286A/R473C-NL1-691, NL3-639, and R471C-NL3-639 were resolved by MALDI-TOF/MS to establish disulfide pairings. The small fractions of R471C-NL3-639 and C286A/R473C-NL1-691 that are secreted into the medium display the same disulfide bonding pattern as the wild-type proteins (see Table 1 for NL3 data), indicating that the exported proteins have the same secondary structure. By contrast, R473C-NL1-691 protein, purified from cellular lysates, revealed several peptides not attributable to neuroligin in the mass spectral profiles. Co-purification with other protein(s) suggests R473C-NL1-691 retained in the cell is covalently associated with cytoplasmic proteins, perhaps chaperones, as indicated by the large aggregates observed by immunoblotting in non-reducing conditions.

TABLE 1

Masses of Cys-containing peptides for alkylated, de-N-glycosylated, tryptic digests of NL3-639 proteins[a]

| Disulfide Linkages | NL3-639 Peptides | Calculated Masses[b] | Observed Masses Wildtype | R471C |
|---|---|---|---|---|
| C106-C141 | D98 -R195[c] | 6628.56[d] | 6627.69 | |
| C293[e] | I282-R309 | 2974.42 | 2974.43 | |
| C340-C351 | V338-R353 | 1749.81 | 1749.78 | |
| C510-C544 | Y497-K548[c] | 5877.69 | 5877.85 | |

[a]73% of NL3-639 amino acid sequence was accounted for in acquired mass spectra. The small tryptic peptide C471-K472 of the R471C mutant is not observed being below the limit of mass detection.
[b]masses are calculated from amino acid sequence (monoisotopic masses are given below 2000 Da, average masses above 2000 Da).
[c]native Asn is converted to Asp by PNGase-F treatment.
[d]numbering includes an alternatively splice sequence of 40 amino acid not found in NL3
[e]free Cys 293 is alkylated by iodoacetamide treatment of NL3 proteins.
[f]weak ionization signal compared to wildtype.

Surface plasmon resonance binding analysis of the mutated proteins. Analysis of β-neurexin binding by surface plasmon resonance showed R471C-NL3-639 to have ~50 fold less β-neurexin binding than wild type (FIG. 14 upper panel), while for R473T-NL1-691 total binding was about three-fold less than wild type. Moreover, R473E-NL1-691 strongly decreased β-neurexin binding, indicating that the homologous Arg in human NL3 also plays a role in recognition of β-neurexin or overall conformation of neuroligin (FIG. 15 lower panel), although the contact surface responsible for the neuroligin-neurexin association remains unknown.

Surface plasmon resonance show the expected specificity whereas binding of mouse AChE, a related α/β hydrolase fold protein, shows no binding to NX1β at concentrations up to 100-fold above where NL1 binding can be demonstrated. The absence of AChE binding does not appear to be a consequence of the different glycosylation pattern on AChE, since a glycosidase treated AChE also shows no detectable NX1β binding.

The analysis shows the expected dependence on $Ca^{2+}$ since when $Mg^{2+}$ is substituted for $Ca^{2+}$ no binding is evident. An analysis of the rates of NL1-NX1β dissociation by buffer perfusion (NL1 depletion) compared with $Ca^{2+}$ depletion by EGTA shows the latter to be far more rapid. This would suggest that the $Ca^{2+}$ site maintaining the conformation for binding does not become inaccessible upon formation of the NL1-NX1β complex, rather when $Ca^{2+}$ is removed the complex immediately dissociates (FIG. 5). Using the same Hepes buffer with different ionic strengths, it was noted that the binding of NL1 with NX1β is highly dependent on the NaCl concentration. Thus, high ionic strength wash procedures may yield different patterns of specificity than can be obtained through direct measures of binding in physiological buffers.

Sedimentation equilibrium analysis shows that soluble NL1 can associate as a homodimer with no indication that higher orders of associated oligomers are present. Dimer formation is unaffected by the presence or absence of the stalk region at the C-terminal end of the extracellular domain, thus confirming the involvement of a four helix bundle region within the cholinesterase homology domain in maintaining adhesion activity. It is therefore likely that both NL1-633 and NL1-626, being unable to form homodimers, do not fold in or retain conformations appropriate for their expression.

Owing largely to their expression patterns, the cholinesterases have been proposed to have non-catalytic morphogenic activities during vertebrate CNS development, promoting both neuritogenesis and synaptogenesis. Since some cell adhesion molecules (neuroligins, tactins) have high sequence similarities with AChE, and over-expression of AChE in transgenic mice caused a drastic decrease in NX1β mRNA, it has been conjectured that there may be an interaction between these two proteins. Mouse-AChE-548 shares with the ChE-like domain of NL1 almost 34% amino acid identity, distributed over the extracellular region up to NL1 residue 638, however no specific NX1β-AChE binding was evident using SPR, a technique that enables detection of complexes formed in the micromolar range (FIG. 4B). On the contrary, three NL1 truncation mutants bind NX1β, confirming that the binding surface in NL1 is located entirely in the ChE-like domain. This result is consistent with the domain swapping studies that demonstrated the AChE domain could not substitute for NL1 in triggering any pre-synaptic modification. These findings, however, cannot exclude the possibility that AChE binds other NX1β forms.

NL1 purified from cell extracts, that is presumably incompletely processed, bound NX1β several fold better than the secreted form. Accordingly, the role of the individual sugars of NL1 and their interaction with NX1β was examined. The demonstration that the deglycosylated protein shows enhanced binding contrasts with many glycoproteins where removal of N-linked sugars produces loss of function. Possibly glycosylation of NL1 plays a regulatory role similar to that seen in the Notch receptor family, where addition of certain O-linked oligosaccharides causes the receptor to become more sensitive to Delta and less sensitive to Serrate/Jagged. Accordingly, Notch signaling is amplified in certain cells, but not in others. Additionally, in the neural cell adhesion molecule (NCAM) protein, polysialic acid oligosaccharides exhibit a highly regulated expression pattern and their presence in certain glycoproteins serves as a modulator of cell-cell interactions.

Studies indicate that full-length NL1 expressed in HEK293 cells is able to trigger morphological and functional presynaptic differentiation in contacting axons. Hence posttranslational modifications of the recombinant protein expressed in the HEK293 cells yielded a NL1 with adhesive functions. The disclosure also shows activity with a mutant lacking a site for glycosylation at N303, whereas AChE does not show adhesion activity.

Given that glycosylation processing inhibited NL1's capacity to bind to NX1β, sequential mutations eliminating single glycosylation signals may indicate the region of the NL1-NX1β association. That only N303A-NL1 mutant is not or marginally influenced by PNGase treatment, indicates that glycosylation processing at Asn303 likely occurs in a region proximal to the NX1β binding site. The specific activity of the N303A mutant was not enhanced as might be anticipated, indicating that side chain substitution of the N303A mutant may alter folding of the protein domain, whereas PNGase F only removes exposed oligosaccharides without interfering with the basic peptide fold. Studies on conformational dynamics of oligopeptides indicate that glycosylation can allow a polypeptide to assume conformations originally not accessible to non-glycosylated peptides. Thus, a sequon may funnel a protein, or one of its domains, through a particular folding pathway producing a specific conformation not otherwise attainable. This role of structure is currently being explored with a series of mutations. Nevertheless, it is likely that the second alternative splicing region (insert B) and glycosylation processing of the product regulate association between NX1β and NL1.

Using a recombinant DNA expression system for protein production, mass spectrometric analysis for characterization of the gene product, surface plasmon resonance binding assays and cell biological analyses of protein biosynthesis, several observations were made on how neuroligin-3 polymorphisms, discovered in man, to explain their association with autism spectrum disorders.

Introduction of a single Cys in the C-terminal region of the extracellular domain of the NL1 or NL3 uniquely compromises the export of the neuroligins to their cell membrane location as they appear to be retained in the endoplasmic reticulum. By contrast, Thr or Glu substitutions allow the neuroligins to be correctly processed in biosynthesis. However, the pattern of cysteine pairings observed by mass spectrometry suggests that the secreted fraction of the protein is correctly folded. By analysis of migration in reducing versus non-reducing conditions of SDS-PAGE and by analysis of mass spectrometry data, the protein retained intracellularly appears disulfide linked with other cytoplasmic proteins, possibly chaperones. Thus far, the precise mechanisms involved in defective trafficking and diminished β-neurexin binding are not understood. Nevertheless, the data indicate that a global misfolding of the extracellular domain of the neuroligins during biosynthesis and altered secondary structure are not responsible. Rather, the data point toward two distinct mechanisms. First, the mutated Cys may become a ER retention signal for NL3, preventing the protein to reach the cell surface. A thiol retention system has been described in a variety of cell types including HEK293 cells, and involves formation of reversible disulfide bonds between ER chaperons and an exposed free Cys residue. This mechanism is believed to monitor the assembly status by assuring intermolecular disulfides bond formation of multimeric proteins such as secretory IgM assembly. Based on the available homology model, Cys at position 451 is exposed to solvent and could act as retention signal similar to Cys575 in the secretory µ chain of IgM polymers.

Second, the secreted neuroligins 3 and 1 mutated at positions 471 and 473, respectively compromise β-neurexin binding capacities, implicating this region in the neurexin-neuroligin association. Since Arg471 is highly conserved in the neuroligins and acetylcholinesterases among all species (from fruit fly to human) and is located in a predicted EF-hand region, Jamain and coworkers (2003) speculated that R451C might modify the binding of neuroligin to β-neurexin compromising the $Ca^{2+}$ dependence of the association. Such a mechanism could be at play in diminishing β-neurexin affinity for the mutant neuroligin. However, the retention in the endoplasmic reticulum appears to be unique to the Cys substitution found in the single base mutation in NL3. The association of the autism spectrum disorders with the neuroligin gene family and the demonstration of aberrant cellular processing with the Cys substitution and diminished affinity for neurexin with several other neuroligin mutants provide an important lead into the functions of proteins involved in the disorder. Certainly mutations in the diverse neuroligin family and other proteins forming heterologous cell contacts in the nervous system warrant further investigation.

Example 2

Construction of Expression Vectors. The pCMVIG constructs of neurexins used contain the following extracellular sequences of various neurexins fused to human IgG: pCMVIGN1β-1 (N1β-1), residues 1-299 of rat neurexin 1β without an insert in SS4; pCMVIGbN1α-1 (N1α-1), residues 1-1361 of bovine neurexin 1α lacking an insert in splice site 4. Chimeric neuroligin 1/acetylcholinesterase mutants (NA) were generated by PCR with corresponding oligonucleotides to create junctions between rat neuroligin 1 and mouse acetylcholinesterase sequences. Neuroligin constructs (schematically depicted in FIG. 18): pCMV5-NA-1: the loop P118-Q149 in neuroligin 1 was replaced by Y101-L123 from acetylcholinesterase. pCMV5-NA-2: neuroligin 1 N343-V348 was replaced by acetylcholinesterase P289-T298. pCMV5-NA-3: neuroligin 1 NL1 I535-C546 was replaced by acetylcholinesterase L488-L494; pCMV5-NA-4: neuroligin 1 Q574-E591 was replaced by acetylcholinesterase D522-K527. pCMV5-NA-1/3: double mutant of NA-1 and NA-3. pcDNA3-NA-5: The N-terminal sequence of acetylcholinesterase was fused at L570 to the C-terminal part of neuroligin 1 starting at H634. For expression vectors that encode secreted proteins containing neuroligin extracellular domains without transmembrane and intracellular domain, the rat-NL1/AChE chimeras were subcloned into FLAG tagged vector (Sigma, St. Louis, Mo.) for detection and purification, resulting in FLAG-NL1/AChE. FLAG-NL1/AChE proteins were truncated by introducing a stop codon at Ile-639, generating the protein FLAG-NL1/AChE-638.

Cell culture and Neurexin Binding Experiments. HEK293 and COS cells were maintained as above. Cells were transfected using Fugene 6 (Roche Molecular Biochemicals). To obtain cell clones expressing secreted neuroligins truncated at Ile-639, HEK293 cells were transfected and selected. After calcium phosphate transfection, cells were selected by growth in 800 μg/ml G418 (Geneticin, Sigma), and 32 resistant clones for each chimera were transferred into two 24-well plates. After incubating the growing cells for a period of 5-8 days, media was tested for the presence of soluble FLAG-NL1/AChE chimera.

In order to purify IgG neurexin fusion proteins, the supernatant of COS cells transfected with the corresponding plasmids was harvested 3-4 d after transfection, adjusted to 10 mM Hepes-NaOH pH 7.4 and 0.1 g/l PMSF, cleared by centrifugation (2,500 g), and incubated overnight with protein A Sepharose 4 Fast Flow (Amersham Pharmacia Biotech). The Ig-fusion proteins attached to Sepharose were washed three times with PBS before pulldown experiments or elution with 10 mM glycine buffer at pH 3.5. The eluate was immediately pH-equilibrated with 20 μl of 1 M Tris-HCl pH 8 per ml of eluate. Pulldown experiments were performed with neuroligins expressed in transfected COS cells that were harvested 3-5 days after transfection and solubilized in 1% (v/v) Triton X-100, 50 mM Tris-HCl pH 7.5, 0.15 M NaCl, 0.1 g/l PMSF, and 2 mM $CaCl_2$ under stirring at 4° C. for 90 min. The mixture was centrifuged at 100,000×g for 1 hour to remove insoluble materials. The supernatant was incubated with neurexin IgG fusion proteins immobilized on protein A beads at 4° C. for 2-4 hours. Proteins bound to the protein A beads containing the IgG fusion proteins were washed with PBS and eluted with sample buffer, and neuroligin binding to neurexin 1β was analyzed by SDS-PAGE electrophoresis, Western blotting and staining with antibodies to neuroligin 1 (4C12, L067).

For cell surface labeling experiments, wildtype and mutant neuroligins were transfected into HEK293 cells. Three days after transfection, soluble IgNrx1β-1 fusion protein was added to the media and incubated at 4° C. for 2 hours. Cells were washed three times with PBS and fixed in cold 4% paraformaldehyde/PBS without permeabilization, and incubated with antibodies against the extracellular part of NL1 (4C12) in PBS with 1% goat serum and 2% BSA. Bound IgNrx1β-1 fusion protein and neuroligin antibodies were detected by Alexa Fluor 488 protein A-conjugate and secondary antibodies Alexa Fluor 546 goat anti-mouse highly cross-adsorbed correspondingly (Molecular Probes). Z-section images were collected using Leica TCS2 confocal microscope.

Primary neuronal culture and neuron/COS-cell co-culture experiments. Primary hippocampal neuronal cultures used for synapse formation assays were prepared from E18 rats. Dissociated neurons were plated onto poly L-lysine treated glass coverslips at a density of 50-200 cells/mm² and co-cultured over a monolayer of glia. Cultures were maintained in Neurobasal medium supplemented with N2 (LifeTech/GIBO-BRL). Transfected COS cells were added to the neurons at 10-14 days in vitro (DIV). After 2-5 days of co-culture, cells were fixed in cold 100% methanol or 4% paraformaldehyde/PBS, permeabilized in 0.2% Triton X-100/PBS or 0.1% Saponin/PBS, and incubated with primary and secondary antibodies in PBS with 1% goat serum and 2% BSA. To test the effect of adding soluble neurexin ligand for neuroligins on synapse formation, soluble IgNrx1β-1 fusion protein (final concentration=10 μg/ml) was added to the neuronal media before the transfected COS cells were seeded onto the neurons. Two days later, the co-cultures were fixed and stained as described earlier. Soluble IgNrx1β-1 was visualized using protein A-488 conjugate, and neuroligin and synapsin antibodies were visualized subsequently using Alexa Fluor 546- and 633-labeled secondary antibodies (Molecular Probes). Fluorescence imaging was performed using sequential acquisition of different channels on a Leica TCS2 confocal microscope. The following antibodies were used for immunocytochemistry of the co-cultures: anti-neuroligin 1 mouse monoclonal 4C12 and rabbit polyclonal L067; anti-synapsin mouse monoclonal C110.22 and rabbit polyclonal E028, anti-synaptophysin rabbit polyclonal K831, anti-PSD-95 rabbit polyclonal L667, anti-ERC rabbit polyclonal P224, and anti Flag-epitope monoclonal antibody (Sigma Aldrich). Secondary antibodies (Alexa Fluor 488-, 546- or 633-labeled highly cross-adsorbed goat anti-mouse or goat anti-rabbit antisera) were from Molecular Probes.

Electron microscopy. For standard EM, cultured cells were fixed in 2% glutaraldehyde, 0.1M cacodylate buffer pH 7.4 for 20 min, and postfixed in 1% OsO4, 0.8% potassium ferricyanide ($K_3FeCN_6$) for 15 min on ice followed by 15 sec in a microwave oven (350W, BioWave, Ted Pella Inc., Redding. CA). For immunoelectron microscopy, cells were fixed in 1% glutaraldehyde, 2% paraformaldehyde in PBS pH 7.4 for 1 hour, and then blocked in 2% normal goat serum, 1% BSA and 0.1% Saponin in PBS. The primary incubation was carried out for 1 hour with the anti-GFP antibody at a dilution of 1:1000. After washing with PBS, the cells were incubated with anti-rabbit secondary antibody conjugated to 1.4 nm gold particles (Nanoprobes, Yaphank, N.Y.) for 1 hour, and then silver enhanced with the HQ silver enhancement kit (Nanoprobes). The immuno-labeled cells were dehydrated through a graded series of ethanol to 100% (15 sec each at 350 W in the microwave oven), and embedded in Poly/Bed 812 epoxy resin (Polysciences Inc., Warrington, Pa.). Ultrathin sections (70 nm) are stained with 5% uranyl acetate solution and examined under a JEOL 1200EX transmission electron microscope at 80 kV accelerating voltage.

Image Acquisition and Analysis. Images were recorded in a confocal microscope Leica TCS2 with the same confocal acquisition settings for all samples of an experiment. Collected z-section images were converted to maximal projection images and analyzed blindly using Leica Confocal Software. Transfected COS cells in close proximity to neurons were selected based on neuroligin and synapsin labeling. The contours of the transfected COS cell were chosen as the region of interest. Fluorescence intensity was quantified for both green and red channel in the region of interest. Statistical significance was determined by Student's t test. All data shown are means±SEMs.

Figure 15:
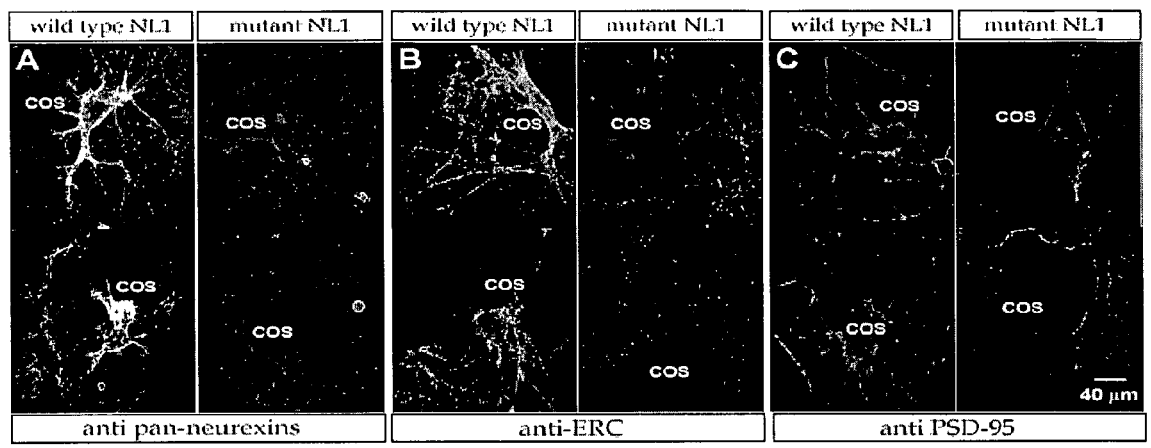

Synapses formed by hippocampal neurons with co-cultured transfected COS cells. COS cells were transfected with wildtype neuroligin 1 and, as a negative control, a mutant neuroligin 1 that does not bind to neurexin 1β (see below). The cells were co-cultured with hippocampal neurons at low density, and examined for synapse formation by indirect immunofluorescence. The co-cultures were stained with a series of antibodies to pre- and postsynaptic proteins to identify synapses, and with antibodies to neuroligin 1 applied at a low dilution to visualize COS cells that express neuroligin 1 (FIG. 15). In the transfected COS cells, neuroligin 1 was uniformly expressed over the entire COS cell surface as visualized by indirect immunofluorescence labeling. The presence of neuroligin 1 stimulated the elaboration of hundreds of presynaptic specializations by the co-cultured neurons. In spite of the uniform expression of neuroligin 1 on the COS cell surface, the induced synapses formed separate individual units that were densely spaced and covered entire cells (e.g., see FIG. 15A) or clustered in a particular region (e.g., see FIG. 15B). The artificially induced nerve terminals on the COS cells were stained with multiple presynaptic markers, including all vesicle proteins tested. In particular, the terminals contained high concentrations of neurexins (FIG. 15A), demonstrating that neurexins are enriched in presynaptic terminals. Active zone proteins such as ERCs (FIG. 15B) were also present, whereas no significant labeling of postsynaptic markers such as PSD-95 was observed (FIG. 15C).

Figure 16:
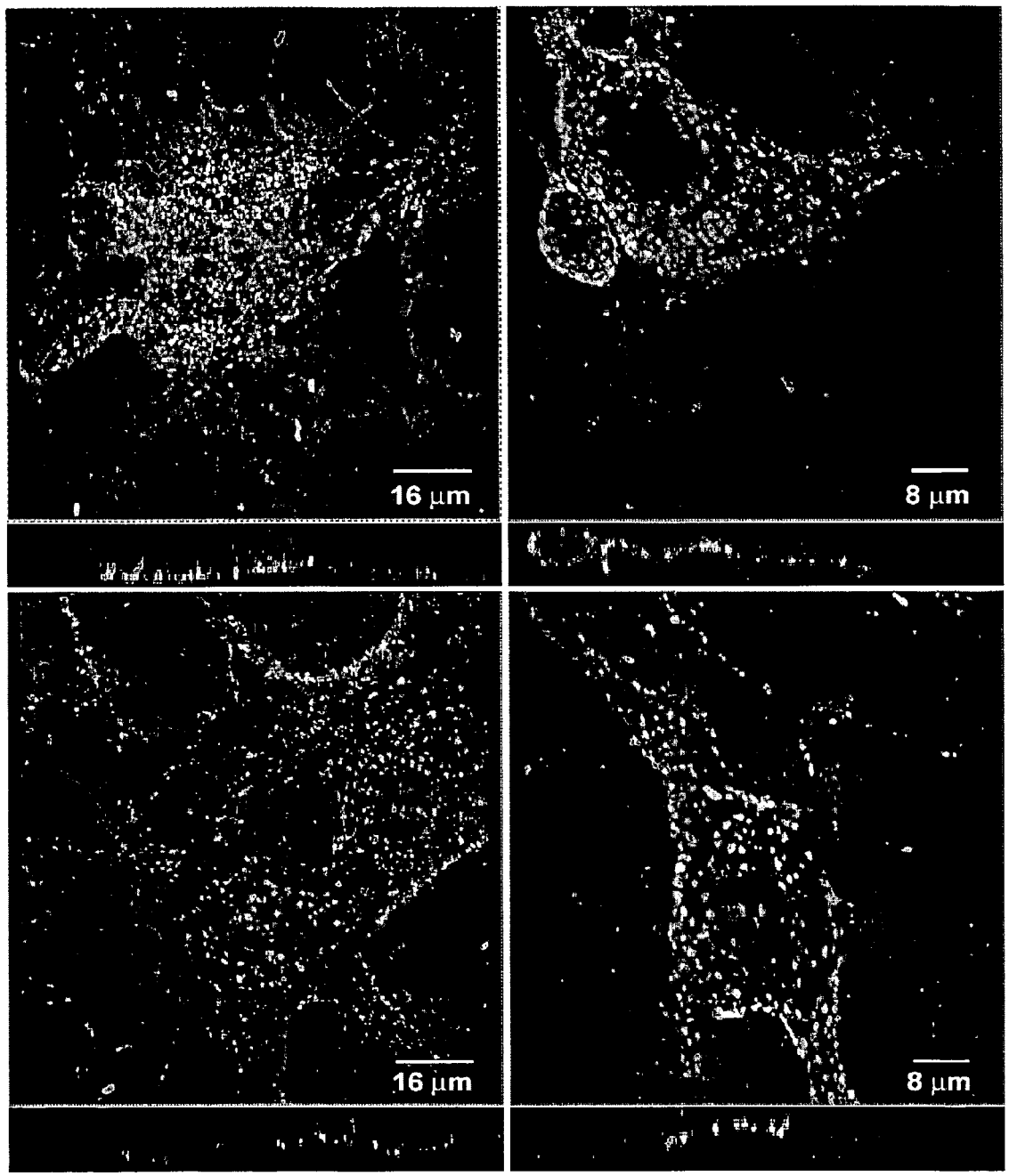

To characterize further the heterologous synapses induced by neuroligin 1, the cells were examined by confocal microscopy at higher resolution (FIG. 16). Synapses form on the surface of the COS cells as hundreds of densely packed presynaptic specializations with a uniform size (~0.75 $\mu m^2$). In most cases, the synapses on a transfected COS cell are derived from 2-4 adjacent neurons, but occasionally the hundreds of synapses on a COS cell are generated from a single adjacent neuron. The density of synapses between neurons and the neuroligin-expressing COS cells is much higher than that observed between neurons, suggesting that the overexpressed neuroligin 1 is a powerful inducing agent for synaptogenesis (FIG. 16).

Figure 17:
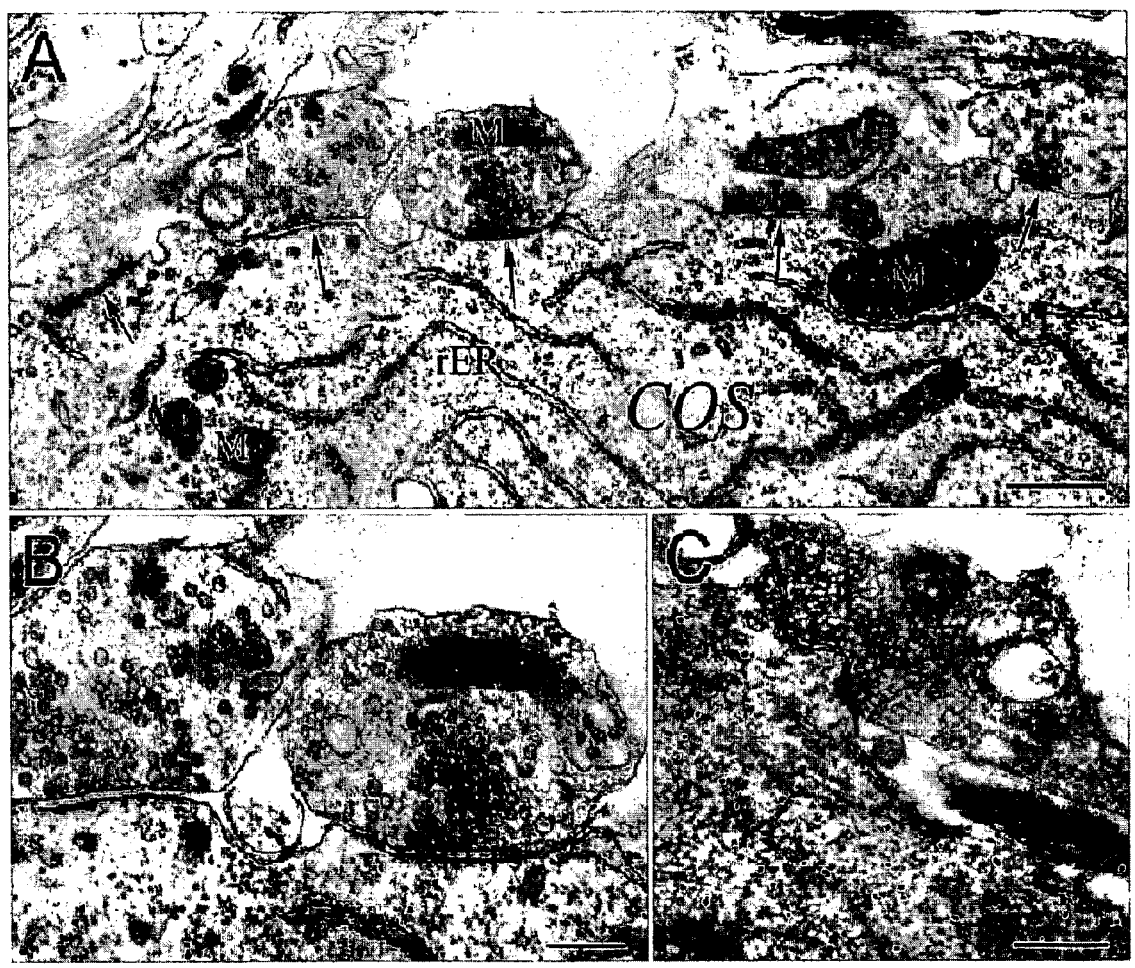

Electron microscopy revealed that the artificial synapses are morphologically similar to interneuronal synapses (FIG. 17). They are formed by nerve terminals or en-passant axons. The presynaptic terminal does not become unusually large but appears to wander on the surface of the transfected COS cells to generate a plexiform synaptic layer. Surprisingly, in some (but not all) of the formed synapses an electron dense thickening of the postsynaptic membrane in the transfected COS cells was observed (FIG. 17B). The postsynaptic thickening is similar to a postsynaptic density in normal synapses, even though the transfected cells only expressed neuroligin 1 and, as far as tested, no other typical postsynaptic marker. To ensure that the synapses analysed by electron microscopy are truly on transfected COS cells, their cellular features were examined. In the postsynaptic cell, the typical characteristics of COS cells were: Large irregularly shaped cell bodies, a high density of rough endoplasmic reticulum, and the absence of typically neuronal extensions or presynaptic specializations. The transfected COS were confirmed to be transfected by immunolabeling of co-transfected GFP (FIG. 17C) and neuroligin.

Figure 18:
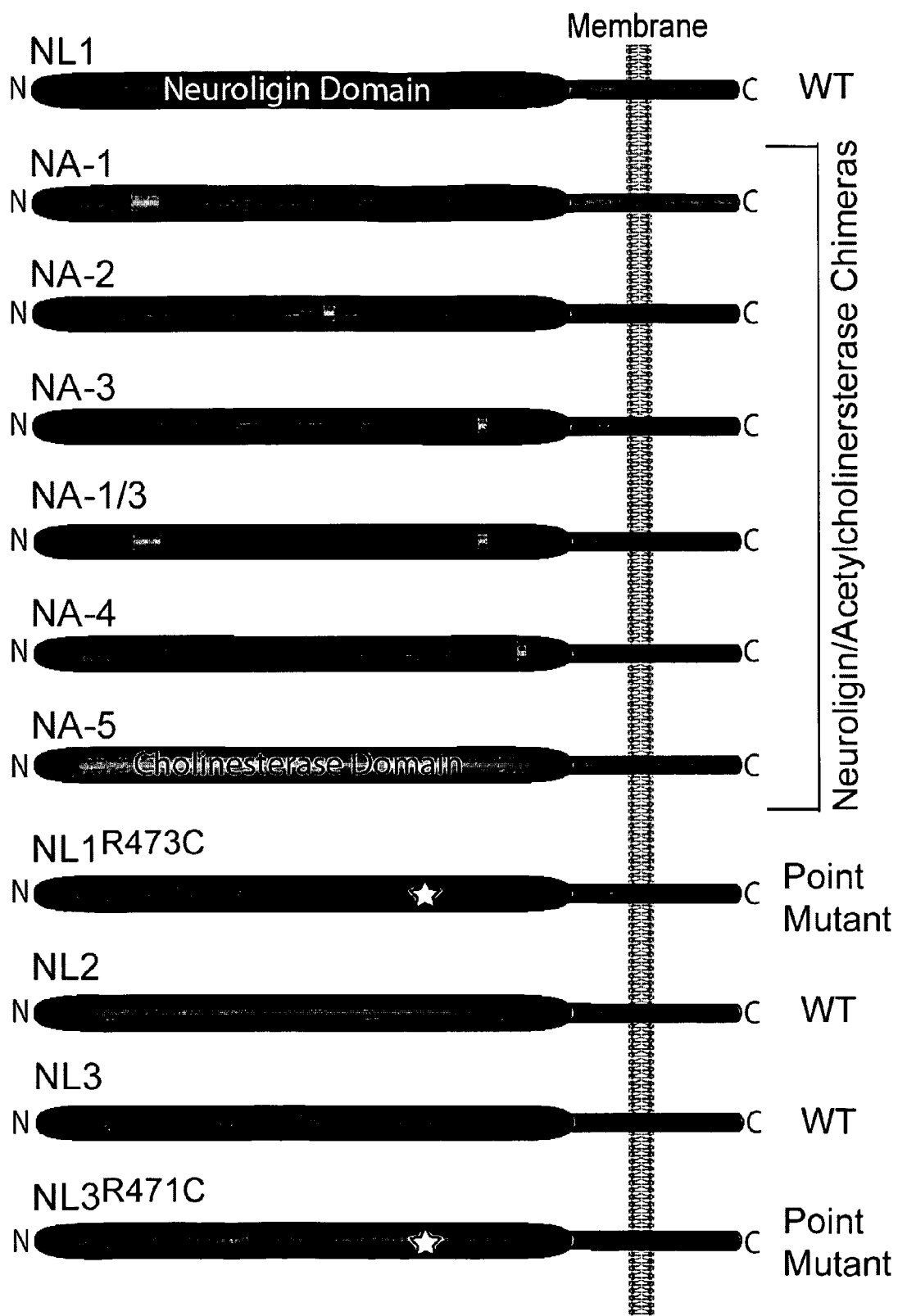
Figure 20:
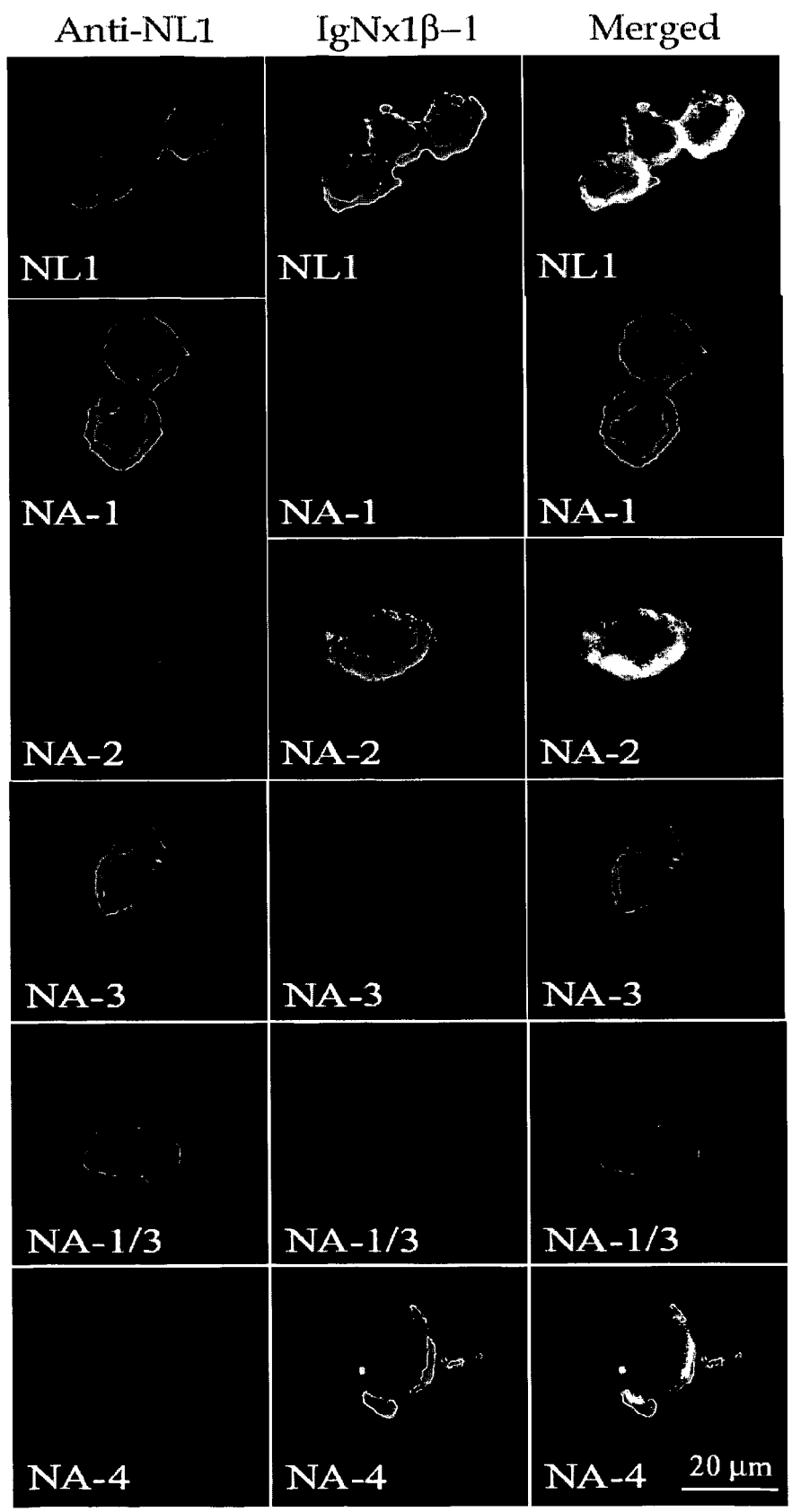
FIG. 20 shows that wildtype and mutant neuroligin 1 are transported to the cell surface. HEK293 cells transfected with wildtype or mutant neuroligin 1 were incubated with soluble neurexin 1β-fusion protein, fixed without permeabilization, and stained by double immunofluorescence with antibodies to the extracellular sequences of neuroligin 1 (left panels) and the Ig moiety of Ig-neurexin 1β (central panels); the merged fluorescence image is shown on the right. Calibration bar in the right lower panel applies to all panels.
Figure 21:
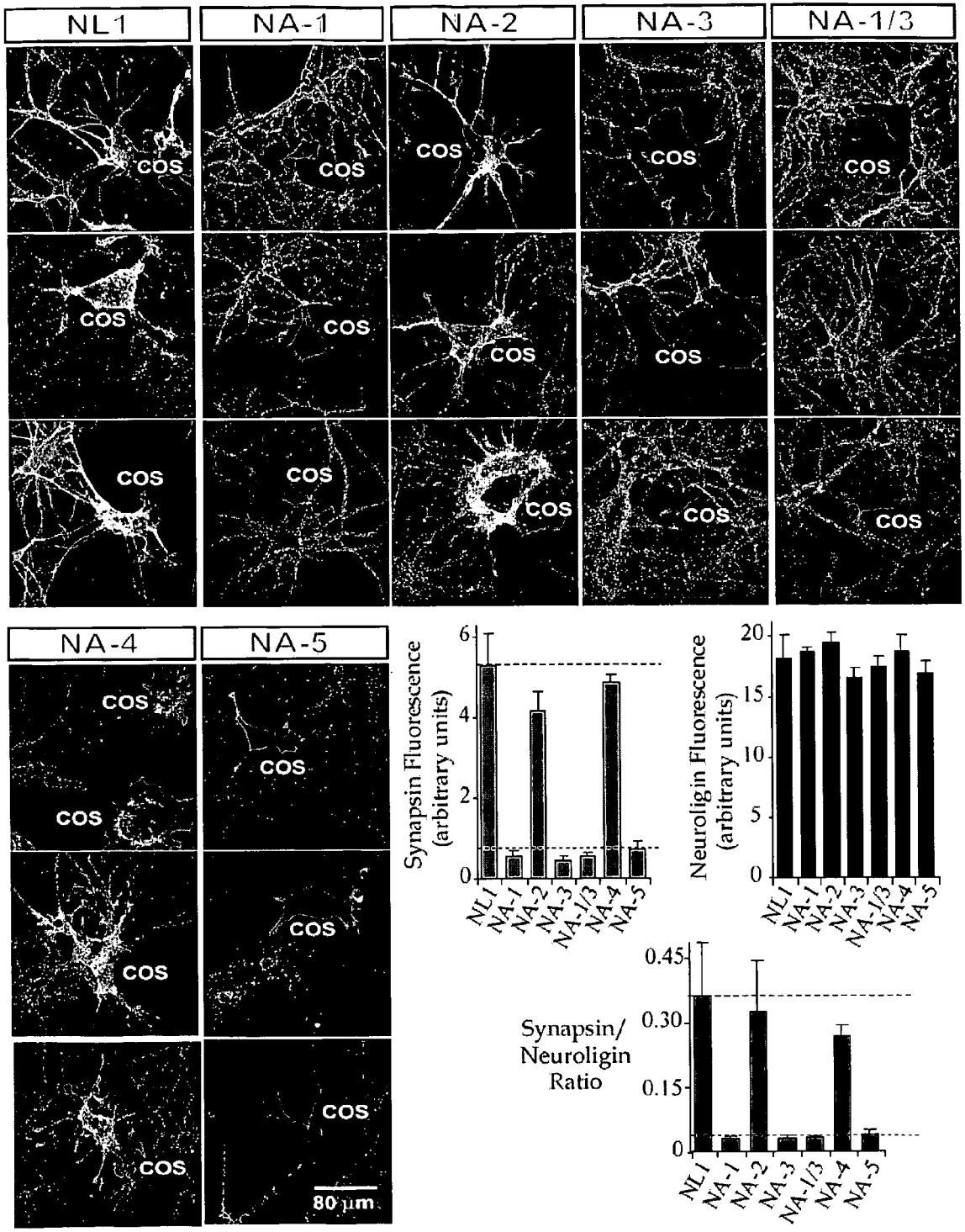
FIG. 21 shows synapse formation induced by mutants of neuroligin 1. COS cells transfected with the neuroligin 1 mutants described in FIG. 18 were co-cultured with hippocampal neurons at low-density. After two days in vitro, cells were fixed and labeled by immunofluorescence for neuroligin (red) or synapsin. For each neuroligin 1 variant, three examples are shown to illustrate that in spite of the variability of the transfected COS cells and of the extent with which neurons populate their surface with nerve terminals, the fundamental observation that synapses are only formed with neuroligin variants that bind to β-neurexins is highly reproducible (see also FIG. 22). Calibration bar in the upper right panel applies to all images. Quantitation of synapse formation by cultured hippocampal neurons onto transfected COS cells expressing various neuroligin mutants. The fluorescence signal obtained in double-labeling experiments was quantified in a CCD camera. The synapsin and neuroligin 1 signals observed in individual COS cells were measured. Dashed and dotted lines refer to the signals of NL1 as the positive control, and of NA-5 (the inactive acetylcholinesterase/NL1 hybrid) as a negative control.

Generation of neuroligin 1 mutants that lack neurexin 1β binding. A simple deletion of the C-terminal portion of the extracellular domain, a region presumably involved in dimerization of neuroligin 1, abolishes its transport through the secretory pathway. By comparing neuroligin and acetylcholinesterase sequences, four such solvent-exposed loops were identified. To examine the structure/function relation of neuroligin 1, the corresponding acetylcholinesterase sequence of these loops was substituted for the neuroligin 1 sequence (FIG. 18). In addition, a neuroligin 1 mutant was constructed in which two of the loop exchanges were combined, and (as a negative control) a hybrid molecule in which the whole extracellular domain of neuroligin was replaced by the cholinesterase catalytic domain. The resulting proteins were then tested for neurexin 1β binding (FIG. 19), transport to the cell surface (FIG. 20), and synapse formation (FIG. 21).

Figure 19:
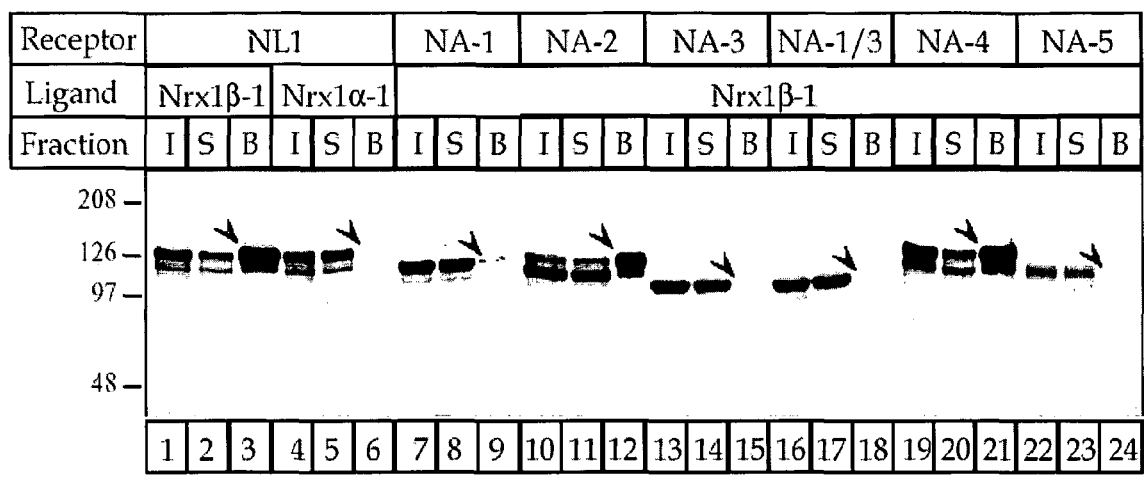

To measure neurexin 1β binding, the neuroligin 1 mutants were expressed in COS cells. An immobilized recombinant Ig-fusion protein of neurexin 1β was then used to monitor binding of the mutants solubilized from the transfected cells (FIG. 19). Neurexin 1β captured neuroligin 1 expressed in COS cells effectively (arrowhead in lane 3, FIG. 19), whereas neurexin 1β, used as a control, was unable to do so (arrowhead in lane 6). Analysis of the neuroligin 1 mutants revealed that two of the four substituted loops were essential for neurexin 1β binding (lanes 9, 15, and 18), while two other loops were dispensable (lanes 12 and 21). As expected, the extracellular acetylcholinesterase domain was unable to bind neurexin 1β (lane 24).

To independently confirm the neurexin 1β-binding properties of the various neuroligin 1 mutants and to ensure that the mutant neuroligins are still transported to the cell surface in transfected cells HEK293 cells expressing neuroligin 1 mutants were incubated with the soluble Ig-Neurexin 1β fusion protein. The cells were then fixed without permeabilization, and probed by immunofluorescence using an antibody to neuroligin 1 that recognizes its extracellular sequence and an antibody to human immunoglobulin that recognizes the Ig-neurexin 1β fusion protein (FIG. 20). All neuroligin 1 mutants were robustly expressed on the cell surface, whereas binding of Ig-neurexin 1β was only observed for those mutants that also bound neurexin 1β in the pulldown assay.

To examine quantitatively the binding of neurexin 1β to the chimeric neuroligins, the soluble recombinant forms of neuroligins were expressed by introducing stop codons into the full-length cDNA at Ile-639 (18). Thirty-two individual clones for each truncated chimeric neuroligin were selected, and the expression of each protein was confirmed by immunoblotting of the conditioned medium. Glycosylated proteins that misfold or form incorrect disulfide arrangements are often retained in the endoplasmic reticulum. The surface transport of the neuroligin 1 mutants NA1-4 in as a transmembrane protein, but not as truncated secreted proteins (at least for the NA1, NA3, and NA1/3 mutants), suggests that these mutants still maintain some of their secondary and tertiary structure, but do not form as stable of a conformation as the wildtype proteins. As described below, a similar observation was also made with the autism-mutant neuroligins.

Testing neuroligin mutants for synapse formation. The ability of various neuroligin 1 mutants to induce synapse formation was also examined (FIG. 21), using the assay described above that employs transfected COS cells with co-cultured hippocampal neurons plated at low density (FIGS. 15-17). The cells were stained after 2-5 days of co-culture with antibodies to neuroligin 1 (to visualize transfected COS cells) and to synapsins (to visualize nerve terminals). The two neuroligin mutants that still bound to neurexin 1β effectively stimulated synaptogenesis on the transfected COS cells. In contrast, no enrichment of presynaptic nerve terminals on COS cells expressing the neuroligin 1 mutants that did not bind to neurexin 1β was observed (FIG. 21). Quantitation of the synapsin and neuroligin 1 signal associated with transfected COS cells in multiple independent experiments revealed that synapse formation was reproducibly observed only with wildtype neuroligin 1 and with those neuroligin 1 mutants that still bound to neurexin 1β (FIG. 21).

Synapse formation by other neuroligins and by mutant neuroligins carrying the Arg471Cys substitution. To test whether synapse formation is a general property of neuroligins, neuroligins 1, 2, and 3 were investigated. In addition, to probe whether the Arg471Cys mutation, observed in the neuroligin 3 gene of a case of a familial autistic syndrome, this mutation both in the context of neuroligin 3 (the congenital mutation in man) and of the more extensively studied neuroligin 1 (where Arg471 corresponds to Arg473) was studied. The neuroligin constructs used are schematically depicted in FIG. 18.

In transfected cells, wildtype neuroligins 1, 2, and 3 were transported to the cell surface with a similar efficiency. Both mutants (neuroligin $1^{Arg473Cys}$ and neuroligin $3^{Arg471Cys}$) were largely retained in the cell interior as described, although some of the mutant molecules were still able to reach the cell surface. Neuroligins 1, 2, and 3 were fully capable of inducing synapse formation (FIG. 22). Surprisingly, in spite of their poor transport to the cell surface, the mutant neuroligin 1 and 3 encompassing the autism mutations also had a significant synapse induction activity (FIG. 22A). This is most clearly illustrated in the quantitations of synapse formation (FIG. 22B) demonstrating that the neuroligin 1 R473C mutant was almost as good in synapse induction as wildtype neuroligin 1, whereas the neuroligin 3 R471C mutant was still significantly better in synapse induction than the inactive NA5 control.

Figure 23:
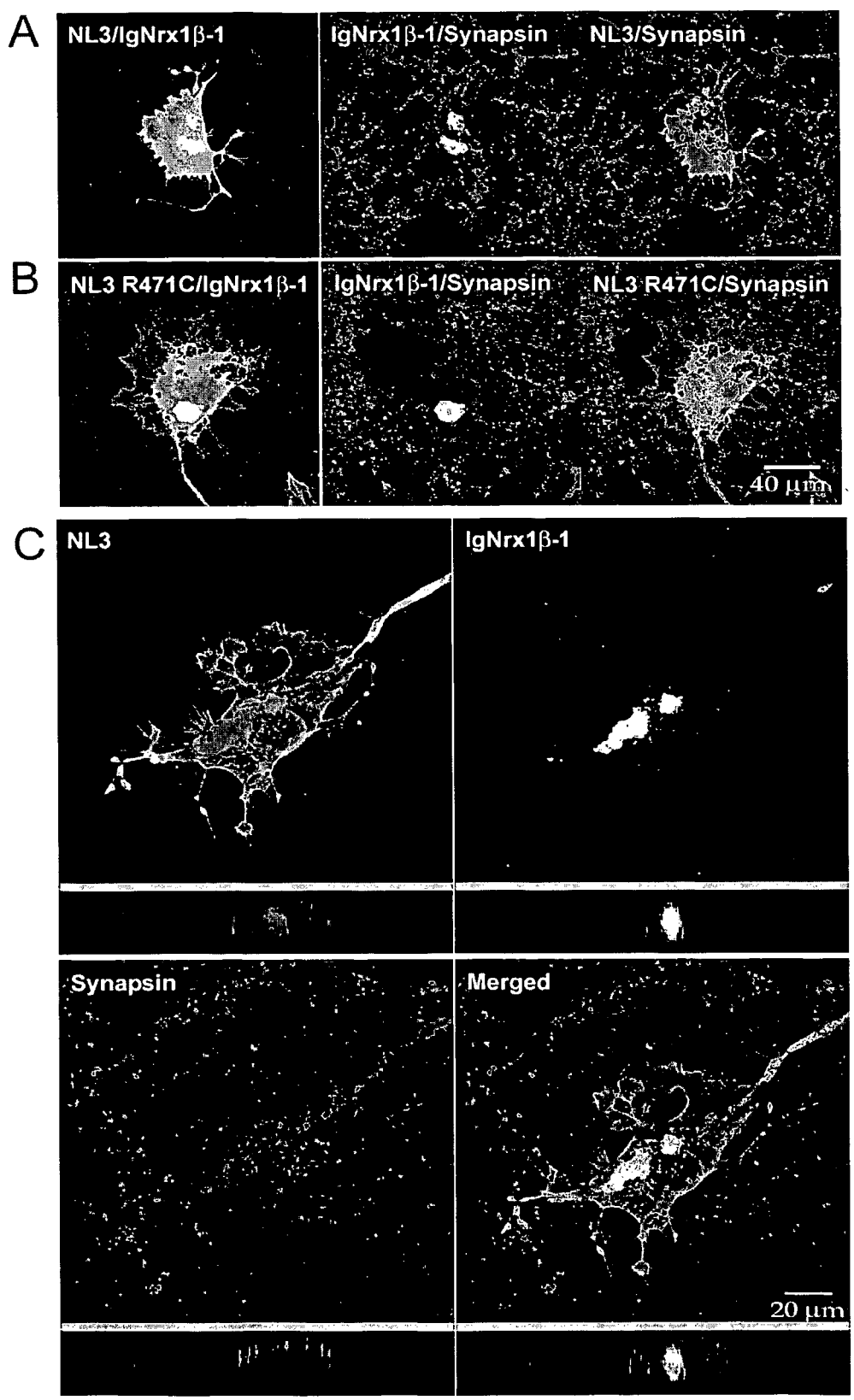
FIG. 23A-C shows that soluble Ig-Neurexin 1β fusion protein is endocytosed by COS cells expressing neuroligin, and fails to completely inhibit synapse formation. A. and B. Synapse formation on COS cells expressing either wild-type NL3 (A) or autism mutant NL3$^{R471C}$ (B) that were co-cultured with hippocampal neurons in the presence of soluble Ig-Neurexin 1βgNrx1β-1). Presynaptic terminals were visualized with polyclonal antibodies to synapsins, neuroligins NL3 or NL3$^{R471C}$ (that are flag-tagged) were visualized in the transfected COS cells with monoclonal FLAG antibodies, and IgNrx1β-1 was visualized with protein A-488 conjugate. Each panel simultaneously depicts two of the three staining reactions. Calibration bar in the right lower corner of the right. B panel applies to all panels in A and B. C. Higher magnification images of a COS cell co-cultured with neurons in the presence of soluble Ig-Neurexin 1β. The cell is shown either from the top surface (upper panels) or as a section through the cell (lower panels). Each panel depicts the result of a single staining reaction except for the merged lower right panels that exhibit the three images merged into a single picture. Note that the section views (lower panels) show that the synapses are formed on top of the surface of the COS cell, whereas the soluble IgNrx1β-1 is intracellular, presumably because it is rapidly endocytosed where it is co-localized with NL3.

A possible approach to testing the specificity of synapse formation by transfected neuroligins is to try to block their effect on the COS cell surface by addition of high concentrations of soluble Ig-neurexin 1β ligand. Synapse formation in co-culture assay using transfected COS cells expressing either wildtype or Arg471Cys-mutant neuroligin 3 when the cells were exposed to soluble Ig-neurexins for extended time periods was examined. However, added Ig-neurexin 1β was quantitatively removed from the cell surface and endocytosed into an intracellular perinuclear compartment (FIG. 23). Comparison of COS cells expressing wildtype or Arg471Cys-mutant neuroligin 3 showed that synapse formation was much less in the latter than the former, but the mutant neuroligin 3 nevertheless mediated uptake of soluble Ig-neurexin 1β (FIGS. 23A and 23B). This observation provides further evidence for the conclusion that when expressed in the context of a membrane-anchored protein, the Arg471Cys-mutant extracellular domain is still transported to the cell surface. FIG. 23C displays high-resolution images of a wildtype neuroligin 3-expressing COS cell co-cultured with neurons. Cross-sections through the cell unequivocally demonstrate that the added soluble Ig-neurexin 1β is transported to an intracellular perinuclear compartment (FIG. 23C), whereas no significant labeling of the cell-surface with Ig-neurexin 1β is observed (note this is in contrast to the experiment shown in FIG. 20 where the cells were incubated at 4° C., whereas in the FIG. 23 experiments the cells were incubated at 37° C. to inhibit synapse formation). In contrast, synapses are formed on top of the transfected cell above the intracellular compartment containing presumably endocytosed Ig-neurexin 1β (FIG. 23C). Together the experiments in FIG. 23 thus demonstrate that synapse formation by neuroligin cannot be easily inhibited by added neurexin ligand because neuroligin undergoes endocytosis even when present in the autism-mutant form.

These experiments show that neurons, when exposed to a large neuroligin-presenting cell surface, form hundreds of new individual 'artificial' synapses. These synapses contain all known presynaptic markers tested, including neurexins. Electron microscopy revealed that the heterologous synapses are composed of discrete, uniformly shaped units even though the expressed neuroligins are displayed homogenuously over the entire cell surface. The artificial synapses appeared to have a normal structure and size, with presynaptic terminals that contained large clusters of synaptic vesicles and well-defined active zones with docked vesicles. The use of transfected COS cells thus allowed a morphological definition of the artificial synapses induced by neuroligin 1 at a higher resolution than possible with HEK 293 cells, that is normally employed.

Furthermore, neuroligins 1, 2, and 3 were active in this suggesting that artificial synapse induction is a general property of neuroligins. The synapse-inducing activity of neuroligin 3 (FIG. 22) supports a neuronal function. In addition to mutations that were designed to test the role of β-neurexin binding of neuroligins in synapse formation, the autism-related mutation of neuroligin-3 results in intracellular retention of neuroligins when the protein is expressed in full-length form, suggesting that the newly introduced Cys may act as an endoplasmic reticulum retention signal. However, a small percentage of transfected neuroligins carrying the 'autism mutation' reached the cell surface. This small percentage was sufficient to induce significant synapse formation, demonstrating that the autistic neuroligin mutation is not deleterious because it causes a generalized loss of synapse formation activity. Instead, it appears likely that this mutation is harmful because it induces alterations in the surface expression of the affected neuroligin, or may cause changes in the rank ordering of neurexin-neuroligin pairs.

It is striking that the autism point mutation appears to impair surface expression more than the loop exchange mutants as judged by the fact that the surface transport of the autism mutants is severely hindered. The autism mutants, however, still bind to neurexin 1β, and still actively induce synapse formation (FIG. 22), arguing for a role of neurexin 1β as an essential component of synapse formation.

What is claimed is:

1. A method of promoting delivery of an antioxidant agent to a cell expressing neuroligin, comprising
   (i) linking the antioxidant agent to a molecule comprising a soluble neurexin domain that interacts with a binding domain of neuroligin to generate a fusion molecule and
   (ii) contacting a cell with the fusion molecule wherein the fusion molecule binds a neuroligin on the cell and delivers the antioxidant agent to the cell expressing the neuroligin.

2. The method of claim 1, wherein the agent is a small molecule.

3. The method of claim 1, wherein the antioxidant is a sulfur-containing antioxidant is selected from the group consisting of 2-mercaptoethanol, dithiothreitol, glutathione, S-adenosylmethionine, dithiocarbamate, dimethylsulfoxide, cysteine, methionine, cysteamine, oxo-thiazolidine-carboxylate, timonacic acid, WR-2721, malotilate, 1,2-dithiol 3-thione, 1,3-dithiol 2-thione, lipoamide, sulfarlem, and oltipraz.

4. The method of claim 1, wherein the cell is in vivo.

5. The method of claim 1, wherein the cell is in vitro.

6. The method of claim 1, wherein the cell is contacted targeted in vivo, comprising contacting a cell by administration of the fusion molecule systemically, orally, intravenously, intraperitoneally, intracerebrally, epidurally, or locally.

7. The method of claim 1, wherein the cell expresses a neuroligin-1.

8. The method of claim 1, wherein the cell comprises a mutated neuroligin-3 having at least 95% identity to SEQ ID NO:2 or SEQ ID NO:4, wherein the mutant neuroligin-3 has a cysteine at position 451 or 471, respectively.

9. The method of claim 1, wherein the soluble neurexin domain that binds to a neuroligin comprises the sequence as set forth in SEQ ID NO:8 from amino acid 198 to 219.

* * * * *